United States Patent [19]
Champagne et al.

[11] Patent Number: 5,980,708
[45] Date of Patent: Nov. 9, 1999

[54] HIGH SENSITIVITY MULTIPLE WAVEFORM VOLTAMMETRIC INSTRUMENT

[76] Inventors: Gilles Y. Champagne, 1527 des Muguets, Ste-Julie, Quebec, Canada, J3E 1J2; Jean Chevalet, 42, boul. de la Tour Manbourg, 75007 Paris, France

[21] Appl. No.: 08/798,016

[22] Filed: Feb. 12, 1997

[51] Int. Cl.$^6$ .................................................. G01N 27/26
[52] U.S. Cl. .................... 204/406; 204/400; 204/412; 204/434; 205/775; 324/71.1; 324/425; 324/614
[58] Field of Search .................................... 204/409, 406, 204/412, 434; 324/71.1, 425, 614

[56] References Cited

U.S. PATENT DOCUMENTS

| | | | |
|---|---|---|---|
| 3,420,764 | 1/1969 | Schlein | 204/406 |
| 4,058,446 | 11/1977 | Zirino et al. | 204/195 R |
| 4,059,406 | 11/1977 | Fleet | 23/230 R |
| 4,083,754 | 4/1978 | Outsuka et al. | 204/434 |
| 4,123,335 | 10/1978 | Seyl | 204/1 T |
| 4,302,314 | 11/1981 | Golimowski et al. | 204/195 R |
| 4,556,472 | 12/1985 | Langdon | 204/406 |
| 4,628,463 | 12/1986 | Sturrock et al. | 364/497 |
| 4,767,994 | 8/1988 | Hopkins et al. | 324/438 |
| 4,805,624 | 2/1989 | Yao et al. | 128/635 |
| 4,897,162 | 1/1990 | Lewandowski et al. | 204/406 |
| 4,917,774 | 4/1990 | Fisher | 204/153.1 |
| 5,104,809 | 4/1992 | Moulton | 436/96 |
| 5,169,510 | 12/1992 | Lunte et al. | 204/299 R |
| 5,180,968 | 1/1993 | Bruckenstein et al. | 324/71.1 |
| 5,186,798 | 2/1993 | Sakai et al. | 204/153.1 |
| 5,192,403 | 3/1993 | Chang et al. | 204/153.1 |
| 5,198,771 | 3/1993 | Fidler et al. | 204/406 |
| 5,217,112 | 6/1993 | Almon | 204/153.1 |
| 5,382,336 | 1/1995 | Bard et al. | 204/153.1 |
| 5,466,356 | 11/1995 | Schneider et al. | 204/406 |

FOREIGN PATENT DOCUMENTS

| | | |
|---|---|---|
| 1227244 | 9/1987 | Canada . |
| 0343702 | 5/1989 | European Pat. Off. . |
| 0 594 010 | 4/1994 | European Pat. Off. . |
| 2451659 | 5/1975 | Germany . |

OTHER PUBLICATIONS

Chevalet et al., "Studies of the Polarographic Wave with Superimposed Potential Perturbations" XP 002047895 *J. Electroanal. Chem.* 197:17–28 (1986) month unavailable.

Fatouros et al., "Theory of Multiple Square Wave Voltammetries" XP 002047896 *J. Electroanal. Chem.* 213:1–16 (1986) month unavailable.

Hermes et al., "An Amperometric Microsensor Array with 1024 Individually Addressable Elements for Two–Dimensional Concentration Mapping" XP 000479669 *Sensors and Actuators, B Chemical* 21:33–37 date unavailable.

Shabrang et al., "Comparison of Ohmic Potentioal Interactions Occurring at Ring–Disk Electrodes" XP 002047897 *J. Electrochem. Soc.* 122:1305–1311 (1975) month unavailable.

(List continued on next page.)

*Primary Examiner*—T. Tung
*Attorney, Agent, or Firm*—Foley & Lardner

[57] ABSTRACT

A high sensitivity multiple waveform voltammetric method and instrument are provided for use in electrochemical and other applications. The method consists of applying one or several variable potential excitation signals between electrodes of an electrochemical cell to produce an electrochemical reaction in the solution. The excitation signals include a DC bias potential increasing cyclically by a potential step to form a potential staircase signal sweeping across a potential domain, and a number of pulse trains either of opposite polarity or shifted in potential per potential step. An electric current derived from a diffusion flux of ions through the solution is measured as a result of the applied excitation signal. The instrument is adapted to perform the method, and is provided with an accurate and low noise signal generator circuit, a circuit for reducing a double layer capacitive effect in the cell, a potentiostat having a virtual mass counter electrode, a feedback circuit for compensating an ohmic drop in the cell, and an integrator circuit for integrating the current signal produced by the cell.

36 Claims, 34 Drawing Sheets

OTHER PUBLICATIONS

Ramaley, "Digital Waveform Generator and Potentiostat Controller for Pulse Electrochemical Techniques" XP 002047898 *Analytical Instrumentation* 15:101–125 (1986) month unavailable.

Goldsworthy et al., "Bipolar Digipotentiograter for Electroanalytical Uses" XP 002047899 *Analytical Chemistry* 44:1360–1366 (1972) month unavailable.

Goldsworthy et al., "A Digital Potentiostat" XP 002047900 *Analytical Chemistry* 43:1718–1720 (1971) month unavailable.

Vassos, "Averaging Polarograph with Digital Output" *Analytical Chemistry* 45:1292–1295 (1973) month unavailable.

Electrochemical Mercury Detection, Iva Turyan et al., Nature, vol. 362, Apr. 22, 1993, pp. 703 & 704.

Multiple Square Wave Voltammetry: Experimental Verification of the Theory, D. Krulic et al, J. Electroanal. Chem., 287 (1990) 215–227.

Double Differential Pulse Voltammetry, A. Molina et al., Journal of Electroanalytical Chemistry, 305 (1994) 97–105.

General Analytical Solution for a Reversible i–t Response to a Triple Potential Step at an SMDE in the Absence/Presence of Amalgamation, A. Molina et al., J.E.Chem. 408 (1996) 33–45.

Triple–Pulse Voltammetry and Polarography, Carmen Serna et al., Anal. Chem. 1993, 215–222.

Nanoband Electrodes for Electrochemical Stripping Measurements Down to the Attomole Range, Joseph Wang et al., Analytica Chimica Acta 293 (1994) 43–48.

FIG. 2A
DE+△E

FIG. 2B
$\overline{SW}$

FIG. 2C
int(+)

FIG. 2D
int(−)

FIG. 2E
int(1)

FIG. 2F
int(2)

FIG. 2G
i

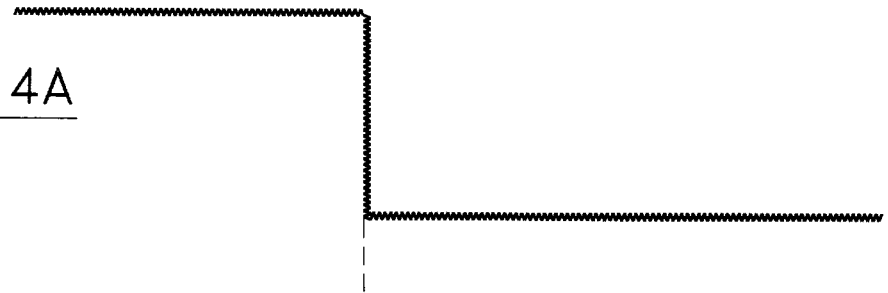
FIG. 4A
FIG. 4B
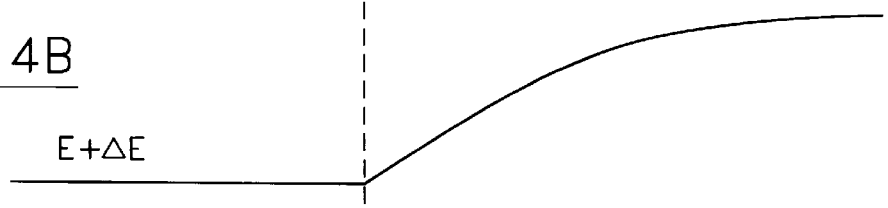
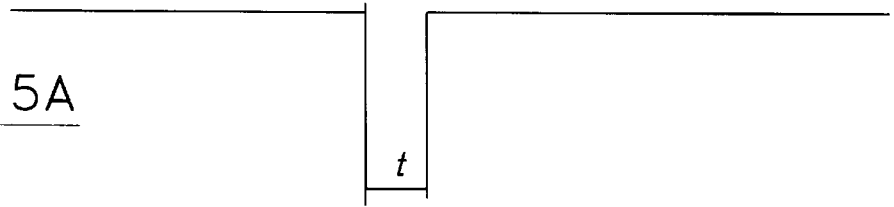
FIG. 5A
FIG. 5B

FIG. 8A $E + \Delta E$

$\tau$ $V_P$

$E + \Delta E + V_P$ $E + \Delta E$ $\overline{SW}$ $V_{i_M}$ $V_{iCAPACITIF}$ $V_{iFARADIC}$

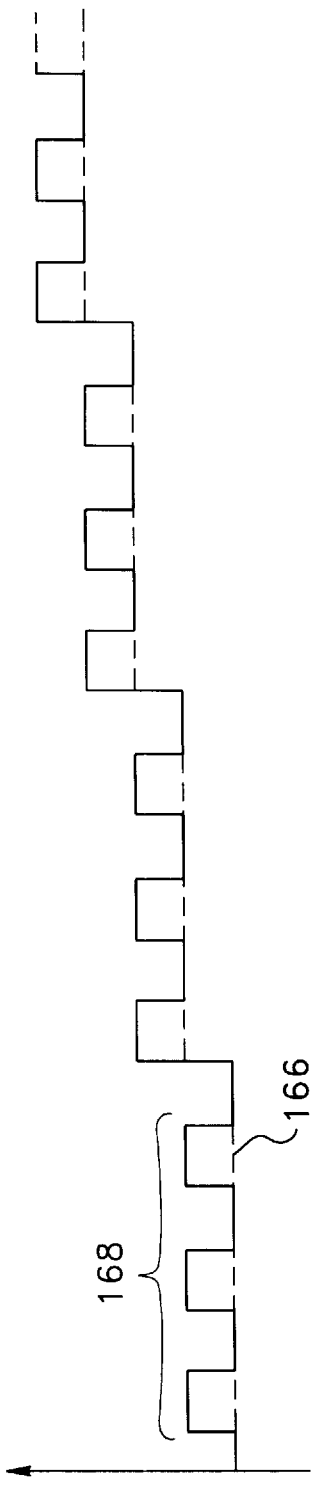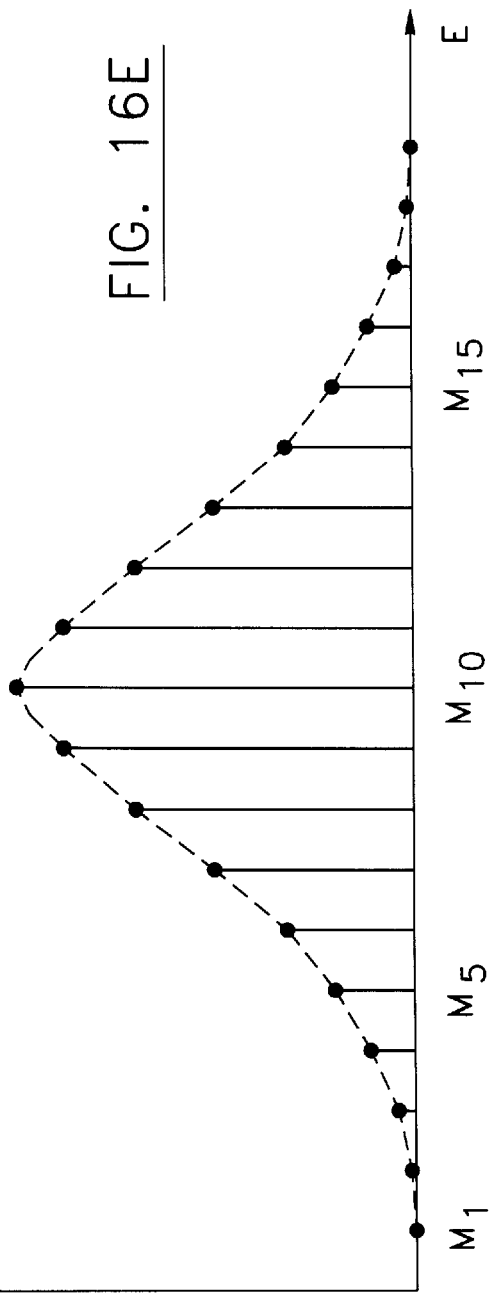

HIGH SENSITIVITY MULTIPLE WAVEFORM VOLTAMMETRIC INSTRUMENT

FIELD OF THE INVENTION

This invention relates in general to electrochemical methods and instruments, and more particularly to multiple waveform voltammetric method and instrument, for use in voltammetry and other domains where a regulated variable potential is needed.

BACKGROUND

Electroanalytical chemistry encompasses a group of quantitative analytical methods that are based upon the electrical properties of an electrolyte solution when it is made part of an electrochemical cell. Electrochemical methods make possible the determination of the concentration of each of the species in the electrolyte solution. Dynamic interfacial methods, in which currents in electrochemical cell play a vital part, are of several types. In controlled-potential methods, the potential of the cell is controlled while measurements of other variables are carried out. Generally, these methods are considered to be sensitive with respect to other methods in the electroanalytical domain, and have relatively wide theoretical ranges which typically does not go lower than 0.5 ppb. Furthermore, many of these procedures can be carried out with microliter volumes of sample. Thus, detection limits in the ppb range can be realized.

Voltammetry and polarography comprise a group of electroanalytical methods in which information about the analyte is derived from the measurement of current as a function of applied potential obtained under conditions that encourage polarization of an indicator, or working, electrode. Generally, working electrodes in voltammetry have a surface area of about a square millimeter, and in some applications, in order to enhance the limiting current, microelectrodes of a few square micrometers (and even less) are used individually or assembled in arrays. In voltammetry, a variable potential excitation signal is impressed by a potentiostat upon an electrochemical cell containing a working electrode. This excitation signal elicits a characteristic current response upon which the method is based. The waveforms of the most common excitation signals used in voltammetry are: the linear scan wave (in polarography hydrodynamic voltammetry), the differential pulse wave (in differential pulse voltammetry), the square wave (in square wave voltammetry), and the triangular wave (in cyclic voltammetry).

In each case, the electrochemical cell represents an electrical equivalent circuit defined in terms of RC components models according to the type of reaction taking place in the cell. The fundamental parameters are the applied potential E, the resulting current i, and the time t. E has a thermodynamic effect on the equilibriums or on the reactional speed, e.g. Nerst relation for the simple cases. The elementary action resides in the application of a step potential perturbation, after which the resulting current response is sampled. The various implemented methods, modes, variants are distinctive only in regard with the arrangements and protocols of imposition of these elementary perturbations repeated together with a change in the base potential. Historically, initial polarography had a sensitivity limit of approx. 1 ppm. Normal pulse polarography (NPP) pushed back the sensitivity limit to approx. 0.1 ppm. At its turn, differential pulse polarography (DPP) pushed back the sensitivity limit to approx. 10 ppb. Square wave voltammetry (SWV) further pushed back the sensitivity limit to approx. 1 ppb. A variation of the DPP method which uses both edges of the perturbation signal, improved the sensitivity by a factor of two, i.e. approx. to 0.5 ppb, whereas multiple square wave voltammetry (MSWV) and differential integrated multiple pulse polarography (DIMPP) achieved a sensitivity of approx. 0.1 ppb.

Known in the art is Canadian patent No. 1.227.244 (Eccles et al.), which describes a method and an apparatus for electroanalytic purposes based on DPP to identify the nature or concentration of species. U.S. Pat. No. 5,186,798 (Sakai et al.) describes a device and a method for performing electrolysis in multiple pulse mode, such as NPP, SWV, DPP and reverse pulse polarography (RPP).

The articles entitled: "Triple-Pulse Voltammetry and Polarography", Serna et al., Anal. Chem. 1993, 65, pp. 215–222; "Double Differential Pulse Voltammetry", Camacho et al., Journal of Electroanalytical Chemistry, 365 (1994), pp. 97–105; and "General Analytical Solution for a Reversible i-t Response to a Triple Potential Step at an SMDE in the Absence/Presence of Amalgamation", Molina et al., Journal of Electroanalytical Chemistry 408 (1996) pp. 33–45, describe theoretical and analytical aspects of a voltammetric method based on the use of a triple pulse of potentials.

Other devices and methods are described in U.S. Pat. No. 4,628,463 (Sturrock et al.), U.S. Pat. No. 5,192,403 (Chang et al.), U.S. Pat. No. 4,917,774 (Fisher), U.S. Pat. No. 5,104,809 (Moulton), U.S. Pat. No. 5,169,510 (Lunte et al.), U.S. Pat. No. 5,217,112 (Almon), U.S. Pat. No. 4,302,314 (Golimowski et al.), U.S. Pat. No. 4,805,624 (Yao et al.), U.S. Pat. No. 5,196,096 (Chang et al.), U.S. Pat. No. 4,767,994 (Hopkins et al.), U.S. Pat. No. 4,058,446 (Zirino et al.), U.S. Pat. No. 4,059,406 (Fleet), European patent application published under No. 0.343.702 (Guerriero et al.) on 29.11.89, German patent application published under No. 2.451.659 (Bednarski et al.) on 28.5.75, and the articles entitled "Theory of multiple square wave voltammeters", Fatouros et al., *J. Electroanal. Chem.,* 213 (1986), pp. 1–16, "Multiple square wave voltammetry: experimental verification of the theory", Krulic et al., *J. Electroanal. Chem.,* 287 (1990), pp. 215–227, and "Electrochemical mercury detection", Turyan et al., Nature, Vol. 362, Apr. 22, 1993, pp. 703–704. However, these devices and methods have sensitivity limits lower than 0.1 ppb or, like in the case of the method reported by Turyan et al. in the above cited article, involve electrochemical regeneration of the electrodes after each experiment and are highly selective (detection specialized for a single species) and thus not flexible. This last case is exemplary of the desirability of a flexible, efficient and reliable method and an instrument which can detect the concentration levels of the traces and ultra-traces of species in the environment, i.e. 1–10 ppt.

Many factors can influence the validity and accuracy of the results. Since the measurements derive from an excitation signal producing a potential difference in the electrochemical cell, the cleaner the excitation signal, the better the results. The command signal that controls the potentiostat applying the excitation signal to the electrodes of the cell must have a high accuracy and be noise free to not alter the electrochemical measurement of the faradic current. However, the prior art devices and methods lack for signal generators producing high accuracy and noise free command signals.

The imposition of a potential step to the electrodes in an electrochemical cell produces a current flow between these electrodes. This current, which is the current to be measured, has essentially two main components: a capacitive component and a faradic component. The capacitive current corresponds to the current required to charge the electric double layer at the interface of the working electrode and the solution (voltammetry is in the group of interfacial methods). The electric double layer is inherent to interfacial electrochemical phenomena and acts in terms of electronic components like an electric capacitor. This capacitance is important (in the order of 10 $\mu F/cm^2$) because of its small dielectric thickness. The faradic current corresponds to the current produced by the electrochemical reactions of oxido-reduction that occur at the working electrode. This faradic current is generally governed by the diffusion of electroactive species inside the gradient of concentration caused by the applied potential at the working electrode. The faradic current is very small, up to many orders of magnitude smaller than the capacitive current, when the concentration of the species in solution to be measured is at the level of traces or ultra-traces. The equivalent electronic component is an electric resistor whose value is a function of the concentration of the species to be measured. The equivalent electric circuit that represents the arrangement of these two components is a circuit where the capacitor and the resistor are connected in parallel. After the imposition of the potential step, the decreasing of the capacitive current is fast and is produced as a function of $\exp^{(-t/RC)}$ whereas the decreasing of the faradic current is slow and is produced as a function of $t^{(-\frac{1}{2})}$ which denotes the diffusion control. The main interest resides in the evaluation of the concentration of the species in solution, which is carried out by measuring the faradic current. The prior art methods consist in allowing a sufficiently long delay to elapse so that the capacitive current becomes small, before proceeding to the measurement of the faradic current. This delay however slows down the process.

Three electrodes apply a potential and measure the resulting current. They are in contact with the solution to be studied in the electrochemical cell. These electrodes are the working, reference and counter (or auxiliary) electrodes. The potential applied on the working electrode is the potential that the electrode/solution interface takes with respect to the environing solution. This applied potential refers to the potential of the reference electrode whose value must remain stable and fixed with respect to the solution, under some thermodynamic equilibrium. The applied potential must therefore be constrained to follow the value of the imposed potential, which amounts to a potential regulation. In the prior art apparatuses, the current measurement is carried out by the use of a current to voltage converter said to be at virtual ground, in the circuit of the working electrode. As a consequence, this has the effect of producing alterations and instabilities of the potential impressed on the working electrode during the current measurements.

To develop a current in an electrochemical cell, a driving force in the form of a potential is required to activate the reaction of ions at the interface of the solution and the working electrode. Just as in metallic conduction, this force follows Ohm's law and is equal to the product of the current in amperes and the local resistance of the solution in ohms. The force is generally referred to as the ohmic potential or the IR drop. In practice, the reference electrode refers to the potential of the bulk of the solution and not to the real potential at the interface where the reaction takes place. The net effect of the IR drop is to increase the potential required to operate an electrolytic cell. The effective potential of the electrode may drop dramatically in the presence of a current, and thus require correction to accelerate the charge of the double layer at the interface of the working electrode and the solution. This correction contributes to a correct double layer charging since the interface capacitance must be adjusted at the right potential and the corresponding component in the overall current is very important at short times. Presently, the correction is calculated according to theory, and may prove inadequate.

The current resulting from the electrodes under imposition of a potential step contains noise derived from various sources, for example the power supply of the instrument. It is therefore desirable to suppress as much as possible this noise, operation that the prior art devices and methods often fail to achieve properly.

SUMMARY

It is therefore an object of the present invention to provide flexible, efficient and reliable method and instrument that have a very high sensitivity corresponding to a detection level in the order of 1 ppt (ng.l$^{-1}$) or less.

It is a subsidiary object of the invention to provide an accurate and low noise signal generator circuit for a potentiostat in a voltammetric instrument, to overcome the aforesaid drawbacks of the prior art.

It is a subsidiary object of the invention to provide a circuit and a method for reducing a double layer capacitive effect in an electrochemical cell, to overcome the aforesaid drawbacks of the prior art.

It is a subsidiary object of the invention to provide a potentiostat and a method thereof for use with an electrochemical cell, so that the manner or the device achieving the current measurement does not affect the potential applied to the electrodes.

It is a subsidiary object of the invention to provide a feedback circuit and a method for compensating an ohmic drop in an electrochemical cell in a more efficient manner than in the prior art.

It is a subsidiary object of the invention to provide a circuit arrangement and a method to suppress the noise in the measured current in a more efficient manner than in the prior art.

In accordance with one aspect of the invention, there is provided a multiple waveform voltammetric instrument comprising:

a signal generator means for generating a command signal including pulses superimposed on a DC bias potential, the generator means including means for selectively inverting the pulses, and means for selecting a DC level of the DC bias potential;

a potentiostat having an input for receiving the command signal, first, second and third instrument terminals, and regulating means for applying, between the first and second instrument terminals, a potential difference corresponding substantially to the command signal;

means for grounding the third instrument terminal and producing an output signal indicative of a current flowing through the third instrument terminal;

an integrator means for integrating the output signal to produce an integrated response signal, the integrator means including means for selectively inverting the output signal prior to integration, and means for resetting the integrated response signal; and control means for time-controlling generation and inversion of the pulses, the DC level of the DC bias potential, inversion and integration of the output signal and resetting of the integrated response signal, according to a selected voltammetric mode of operation.

In accordance with another aspect of the invention, there is provided an accurate and low noise signal generator circuit for a potentiostat in a voltammetric instrument, the signal generator circuit comprising:

a pulse generator means for generating a command signal including pulses;

an active low pass filter connected to the pulse generator, the low pass filter including an amplifier combined with a resistor-capacitor feedback circuit to give the low pass filter a long time constant to filter noise and stabilize the command signal for transmission to the potentiostat; and means for injecting a correcting charge in the capacitor of the low pass filter during pulse transitions in the command signal, to compensate an effect of the time constant of the low pass filter on rise and fall times of the pulses in the command signal.

In accordance with another aspect of the invention, there is provided a circuit for reducing a double layer capacitive effect in an electrochemical cell having a pair of electrodes subjected to a potential difference produced by a potentiostat in response to a command signal including pulses corresponding to the potential difference to be produced, the circuit comprising:

a summing circuit having a first input for receiving the command signal, a second input for receiving impulses, and an output for superimposing the impulses onto the command signal;

an amplifier having an input connected to the input of the summing circuit, and an output;

an adjustable differentiator having an input connected to the output of the amplifier, and an output; and an adjustable attenuator having an input connected to the output of the differentiator, and an output to produce the impulses.

In accordance with another aspect of the invention, there is provided a potentiostat for use with an electrochemical cell having reference, working and counter electrodes, the potentiostat comprising:

an input for receiving a command signal corresponding to a potential difference to be applied between the working and reference electrodes, first, second and third instrument terminals for respective connection with the reference, working and counter electrodes;

regulating means for applying the potential difference between the working and reference electrodes, the regulating means having a first input connected to the input of the potentiostat to receive the command signal, a second input connected to the first instrument terminal to receive a reference potential of the reference electrode, and an output connected to the second instrument terminal to apply an excitation potential on the working electrode, the excitation potential resulting from an addition of the reference potential with the command signal, thereby producing the potential difference between the working and reference electrodes; and means for grounding the third instrument terminal and producing an output signal indicative of a current flowing through the third instrument terminal.

In accordance with another aspect of the invention, there is provided a feedback circuit for compensating an ohmic drop in an electrochemical cell having a pair of electrodes subjected to a pulsed potential difference, and a grounded electrode in which current flows in response to the pulsed potential difference, the feedback circuit comprising:

a current to voltage converter having an input connected to the grounded electrode, and an output to produce a voltage signal as a function of the current;

a switch responsive to a switch signal, the switch having an input connected to the output of the current to voltage converter, and an output to transmit the voltage signal depending on the switch signal;

control means for producing the switch signal to close the switch for a predetermined time period during transitions of the pulsed potential difference, and to open the switch outside the time period;

a summing circuit for adding the voltage signal transmitted by the switch to the pulsed potential difference applied between the pair of electrodes.

In accordance with another aspect of the invention, there is provided a digital integrator arrangement for integrating a current signal produced by an electrochemical cell subjected to a pulsed potential difference, comprising:

a current to voltage converter having an input for receiving the current signal, and an output to produce a voltage signal indicative of the current signal;

a digital integrator having:
an input connected to the output of the current to voltage converter;

a voltage to frequency converter having an input connected to the input of the integrator, and an output to produce a pulsed signal having a frequency indicative of a voltage value of the voltage signal;

an UP/DOWN counter means for counting pulses in the pulsed signal to produce an output count signal, the counter means having an UP/DOWN input to receive an UP/DOWN control signal affecting a counting direction of the pulses in the pulsed signal, and a reset input to receive a reset signal causing the counter means to the reset the output count signal;

comparator means for comparing the voltage signal with a reference signal selected to determine a polarity of the voltage signal, and producing a signal indicative of the polarity; and logic circuit means for producing the UP/DOWN control signal depending on the polarity of the voltage signal as determined by the comparator means; and control means having output to produce the reset signal at predetermined times according to a selected voltammetric mode of operation.

In accordance with another aspect of the invention, there is provided a multiple waveform voltammetric method for electrochemical analysis of species in an electrolyte solution contained in an electrochemical cell having a system of electrodes in contact with the electrolyte solution, comprising the steps of:

(a) applying a variable potential excitation signal between two of the electrodes to produce an electrochemical reaction in the electrolyte solution, the excitation signal including a DC bias potential increasing cyclically by a potential step to form a potential staircase signal sweeping across a predetermined potential domain, and at least one pair of successive pulse trains of opposite polarity per potential step, the pulse trains being superimposed on the DC bias potential; and (b) measuring an electric current derived from a diffusion flux of ions through the electrolyte solution towards one of the two electrodes as a result of the excitation signal applied in step (a);

whereby the electric current measured in step (b) is characteristic of the species in the electrolyte solution, thereby providing for electrochemical analysis thereof.

In accordance with another aspect of the invention, there is provided a multiple waveform voltammetric method for electrochemical analysis of species in an electrolyte solution contained in an electrochemical cell having a system of electrodes in contact with the electrolyte solution, comprising the steps of:

(a) applying two variable potential excitation signals between two respective pairs of the electrodes to produce an electrochemical reaction in the electrolyte solution, each one of the excitation signals including a DC bias potential increasing cyclically by a potential step to form a potential staircase signal sweeping across a predetermined potential domain, and a pulse train per potential step, the pulse train being superimposed on the DC bias potential, both excitation signals varying inside adjacent potential ranges; and (b) measuring an electric current derived from a diffusion flux of ions through the electrolyte solution towards one of the electrodes of each pair as a result of the excitation signals applied in step (a);

whereby the electric current measured in step (b) is characteristic of the species in the electrolyte, thereby providing for electrochemical analysis thereof.

In accordance with another aspect of the invention, there is provided a method of reducing a double layer capacitive effect in an electrochemical cell having a pair of electrodes subjected to a variable potential excitation signal including pulses having sharp rising and falling edges, comprising the step of:

superimposing an impulse to each pulse at a beginning thereof, the impulse having an adjustable amplitude less than approximately three times an amplitude of the pulses, and an adjustable duration less than a pulse width.

In accordance with another aspect of the invention, there is provided a method of compensating an ohmic drop in an electrochemical cell having a pair of electrodes in contact with an electrolyte solution, the electrodes being subjected to a variable potential excitation signal including sudden potential variations occurring at predetermined time intervals and having predetermined durations, comprising the steps of:

(a) measuring an electric current derived from a diffusion flux of ions through the electrolyte solution towards one of the electrodes as a result of the excitation signal;

(b) converting the current measured in step (a) into a voltage signal having a value proportional to a value of the current;

(c) adding the voltage signal to the excitation signal applied to the electrodes during the durations of the potential variations.

In accordance with another aspect of the invention, there is provided a method of improving the S/N ratio in a measurement of a physical phenomenon responsive to a predetermined type of perturbation, comprising the steps of:

producing a sequence of multiple perturbations of said type to affect the physical phenomenon;

measuring the physical phenomenon affected by the perturbations, to produce response signals relative to the perturbations respectively;

time-integrating the response signals to produce integrated response signals; and performing, in time, addition or subtraction operations on the integrated response signals;

whereby repetition of the perturbations and integration of the response signals improves the S/N ratio.

In accordance with another aspect of the invention, there is provided a method of improving the S/N ratio while reducing offset and drift in a measurement of a physical phenomenon responsive to predetermined types of perturbations, comprising the steps of:

producing a first perturbation of one of said types to produce an effect upon the physical phenomenon;

producing either a second perturbation of a same type but opposite to the first perturbation to produce a distinct effect upon the physical phenomenon relative to the effect produced by the first perturbation, or a second perturbation comparable to the first perturbation but of a different one of said types with a shift in a variable affecting the phenomenon;

measuring the physical phenomenon affected by the perturbations, to produce response signals relative to the perturbations respectively;

time-integrating the response signals to produce integrated response signals; and performing, in time, addition or subtraction operations on the integrated response signals;

whereby the integrated response signals provide a derivative type of response as a result of the first and second perturbations, thereby reducing offset and drift while improving the S/N ratio.

BRIEF DESCRIPTION OF THE DRAWINGS

A detailed description of the preferred embodiment(s) is provided herein below with reference to the following drawings, in which like numbers refer to like elements. In the drawings:

FIGS. 2A to 2G are timing diagrams of control signals used for synchronization purposes and a graph of current in the multiple waveform voltammetric instrument according to the invention;

FIGS. 4A and 4B are graphs showing exaggerated views of the input and output signals for a conventional command signal generator;

FIGS. 5A and 5B are graphs showing exaggerated views of the control and output signals for the command signal generator shown in FIG. 3;

FIGS. 8A to 8C are graphs showing the input, impulse and output signals for the impulse superimposing circuit shown in FIG. 7;

FIGS. 16A to 16E are graphs showing a part of the command signal, the corresponding current signal, the corresponding integrated response signal, the command signal sweeping across a predetermined potential domain, and the full scan signal in MSWV, according to the invention;

DETAILED DESCRIPTION OF THE PREFERRED EMBODIMENTS

Figure 1:
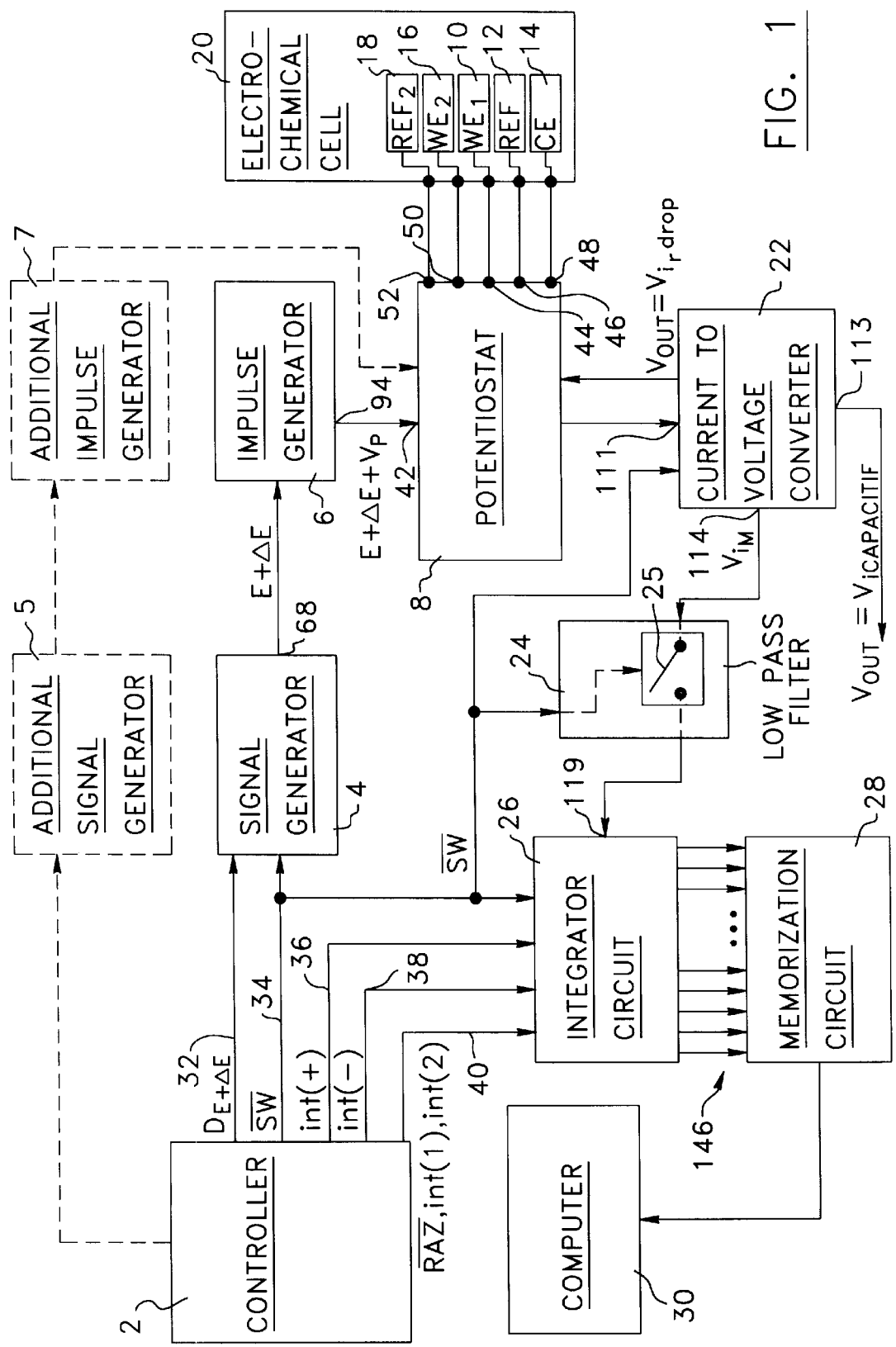
FIG. 1 is a block diagram showing a multiple waveform voltammetric instrument according to the invention.

Referring to FIG. 1, there is illustrated a multiple waveform voltammetric instrument in accordance with a preferred embodiment of the present invention, in the context of electroanalytical chemistry. It should be pointed out that this context is not limitative of the uses that can be made of the instrument, as it will be exemplified hereinafter.

The instrument comprises a first group of circuits 4, 6, 8 devised to form an electrical signal to be impressed onto a selected pair of electrodes 10, 12, 14 (and optionally 16, 18) in an electrochemical cell 20 in order to produce a potential difference therein, and a second group of circuits 8, 22, 24, 26 devised to measure and process a current signal derived from the electrical signal, for analysis with a computer 30. The modes of operation of the instrument are hinged on various control (or synchronization) lines 32, 34, 36, 38, 40, controlled by a controller 2.

The basic circuits involved to form the electrical signal are more particularly a signal generator 4 and a potentiostat 8. The signal generator 4 is used to generate a command signal E+ΔE in response to a control signal $D_{E+\Delta E}$ provided by the controller 2 on the control line 32. E and ΔE represent DC and variable potential components of the command signal respectively. The variable potential component ΔE may consist of pulses that are superimposed on a DC bias potential forming the DC component E. The DC level of the DC bias potential may be controlled via the control line 32 connected to the controller 2. The potentiostat 8 has an input 42 for receiving the command signal, first, second and third instrument terminals 44, 46, 48 for connection with the electrochemical cell 20 (and optionally forth and fifth instrument terminals 50, 52), and a regulator circuit (as formed by circuits 102, 104, 106, 108 in FIG. 9) for applying, between the first and second instrument terminals 44, 46 (or possibly another selected terminal pair), a potential difference corresponding substantially to the command signal E +ΔE. The purpose of the potentiostat 8 is to reproduce the command signal as exactly as possible between the working and reference electrodes 10, 12 to form an accurate potential difference in the cell 20 whichever the potential of the electrode used as a reference, which in the present case is the electrode 12. According to an aspect of the invention, the signal generator 4 can produce pulses inverted or not over the DC bias potential.

The basic circuits involved to measure and process the current signal are more particularly the potentiostat 8, a current measuring circuit like the one formed by the current to voltage converter 22, and an integrator circuit 26. The potentiostat 8 provides a connection with the appropriate electrode in the cell 20 (in the present case, the counter electrode 14) for measurement of the current signal. The current measuring circuit grounds the third instrument terminal 48 and produces an output signal indicative of a current flowing through the third instrument terminal 48. Greater details of how this is achieved will be given hereinafter. The integrator circuit 26 integrates the output signal to produce an integrated response signal in response to control signals provided by the controller 2 on the control lines 34, 36, 38 and 40. According to an aspect of the invention, the integrator circuit is provided with functions for selectively inverting the output signal prior integration in response to a control signal provided by the controller 2 on the control lines 36, 38, and for resetting the integrated response signal in response to a control signal provided by the controller 2 on the control line 40.

The controller 2 can thus time-control the various circuits of the instrument, according to a selected voltammetric mode of operation.

Referring to FIGS. 2A to 2G, there are shown timing diagrams of typical control signals produced by the controller 2 for these synchronization lines 32, 34, 36, 38, 40 (FIGS. 2A to 2F respectively), together with a typical current signal as measured by the instrument (FIG. 2G). The controller 2 can be conveniently embodied by any set of circuits capable to produce accurately and in real time the various required control signals, e.g. a set of accurate and looped timers (monostable) or preferably a quartz clock and a set of counters, or a microcontroller or a processor provided with real time counters/timers to generate the required signal sequences. Preferably, the components should exhibit a relative stability of about $10^{-5}$ $\Delta F/F$, with no jitters. For usual electrochemical applications, the duration of $\Delta E$ (half period) is approx. 5–100 ms, the duration of the integral is approx. 2–100 ms, the delay between a transition of $\Delta E$ and the beginning of the integral is approx. 0.5–10 ms, and the duration of the control signal $\overline{SW}$ is approx. 0.2–10 ms.

The command signal $E+\Delta E$ that drives the potentiostat 8 impressing a potential to the working electrode 10 must be very accurate and devoid of noise in order to not alter the electrochemical measurement of $i_{faradic}$, since any fluctuation in the applied potential during the measurement generates a capacitive current component much greater than $i_{faradic}$.

Figure 3:
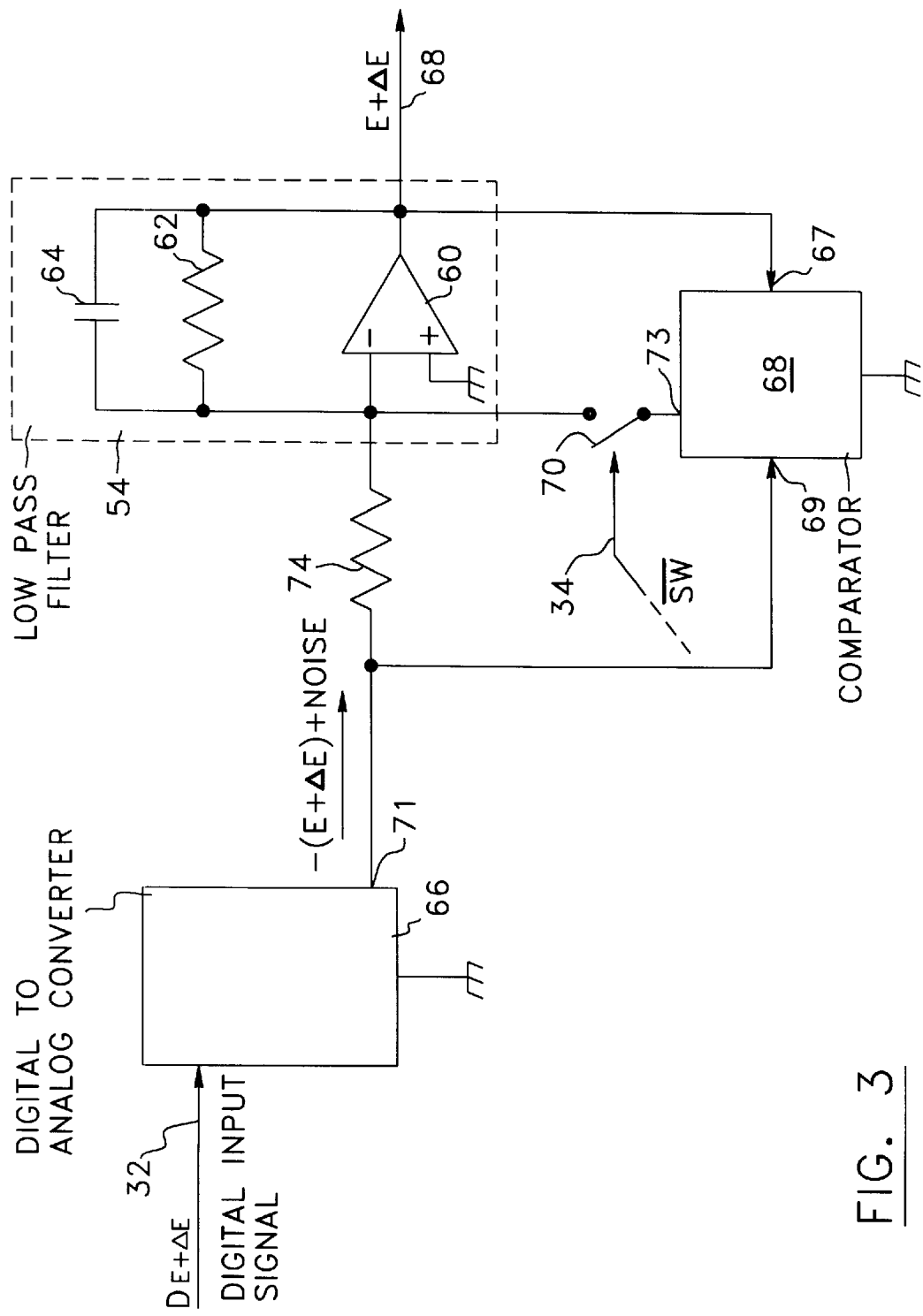
FIG. 3 is a schematic diagram of a command signal generator according to the invention.
Figure 6:
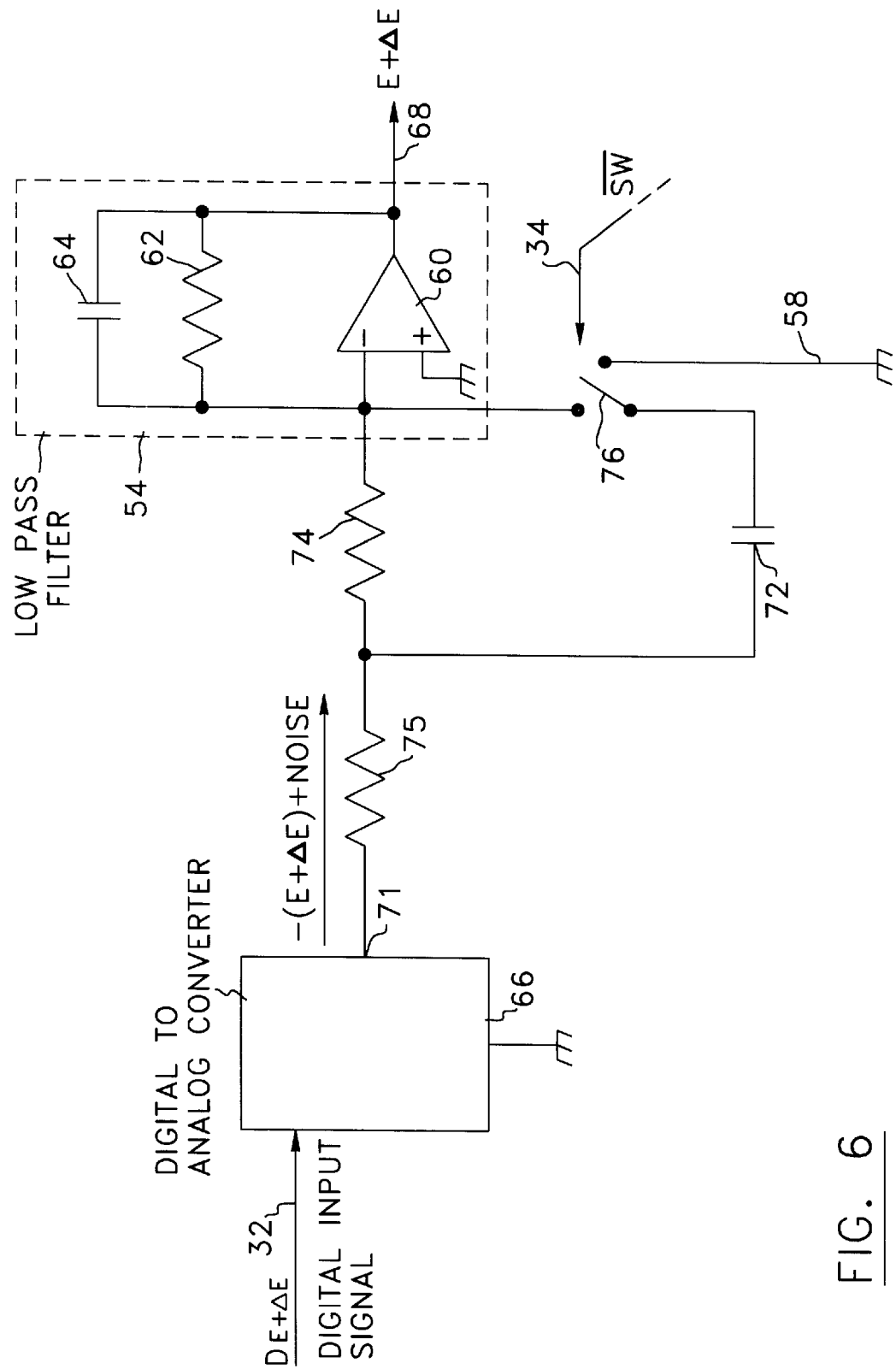
FIG. 6 is a schematic diagram of another embodiment of a command signal generator according to the invention.

Referring to FIGS. 3 and 6, there are shown examples of two possible electronic circuits to form the signal generator 4 (shown in FIG. 1), permitting long time constant filtering and stabilization of the command signal $E+\Delta E$. It should be understood that these circuits can take various other forms without departing from the invention. Long time constant filtering alone would result in an increase of the rise and fall times of the command signal should the present circuits not reduce them to an acceptable level for electrochemical applications. The circuits shown in FIGS. 3 and 6 thus permit to correct the rise and fall times of the command signal $E+\Delta E$, while eliminating as much noise as possible because any fluctuation in the command signal produces a capacitive current in the cell 20. For example, for a usual application, 1 $\mu V$ of noise will generate in the cell 20 a capacitive current of $10^{-10}$ A. The currents corresponding to low ionic concentrations to be measured are of the same order of magnitude. Therefore, the level of noise (over the time spectrum of approx. 1–100 ms) must preferably be lower than 1 $\mu V$.

Referring to FIG. 3, the command signal $E+\Delta E$ is produced by means of a digital-to-analog converter 66 receiving a digital input signal $D_{E+\Delta E}$ from the control line 32 connected to the controller 2 (shown in FIG. 1). Although an analog to digital converter is used in the present embodiment, it should be understood that any suitable controllable signal generator can be used. The command signal $E+\Delta E$ produced by the digital-to-analog converter 66 is however impaired by noise, as shown in FIG. 4A. It is passed into an active low-pass filter 54 including an amplifier 60 combined with a resistor-capacitor feedback circuit 62, 64 whose values are selected to give the filter 54 a long time constant to filter noise and stabilize the command signal. The filter 54 has an output 68 where the noise is attenuated (in the order of $\mu V$), but the rise and fall times of the command signal would be too long (in the order of 100 ms) should nothing else would be done, as shown in FIG. 4B. In order to reduce them, an adjustable gain comparator 68 is used to inject a correcting charge in the filtering capacitor 64 during pulse transitions in the command signal, to compensate an effect of the time constant of the filter 54 on the rise and fall times of the pulses in the command signal, and to restore the value at the output 68 of the filter 54, thus forcing the setting time of the filter 54. This temporary action is obtained by closing a switch 70 only during a time t of a control signal $\overline{SW}$, as shown in FIGS. 5A and 5 B. To this effect, the switch 70 is controlled by the signal $\overline{SW}$ provided by the controller 2 (shown in FIG. 1) on line 34, which is in synchronicity with transitions in the command signal. The comparator 68 has first and second comparator inputs 67, 69 connected to the output 68 of the filter 54 and the output 71 of the analog to digital converter 66 respectively, and a comparator output 73 for producing a signal forming the correcting charge as a function of a difference between absolute values of the signals at the first and second comparator inputs 67, 69. Thus, the comparator 68 takes account of the polarities of the signals and therefore performs an addition when the signals have a same polarity or a subtraction when they have opposite polarities. After the time t, the signal $\overline{SW}$ causes the switch 70 to open, so the filter 54 then regains its initial role.

Referring to FIG. 6, the principle of filtering by a long time constant RC remains the same as in the circuit shown in FIG. 3, except that the circuit to inject the correcting charge is different. The circuit is formed by a capacitor 72 that can be brought in parallel with the resistor 74 upon action of a two-way switch 76 controlled by the signal $\overline{SW}$ provided by the controller 2 (shown in FIG. 1) on line 34. With balanced time constants between the RC circuit 74, 72 and the RC circuit 62, 64 of the filter 54, the effect of the filter 54 vanishes to the profit of a short rise (or fall) time of the signal at the output 68 of the filter 54, so that it reaches the value $E+\Delta E$ very quickly. After the time t of the signal $\overline{SW}$, the switch 76 disconnects the capacitor 72 from the resistor 74 and connects it to ground 58. A resistor 75 having a much smaller resistance value than the resistor 74 is placed at the output 71 of the digital to analog converter 66 to insure stability while connected to the ground 58 by the capacitor 72. The filtering and stabilization effects of the filter 54 are then restored.

Referring to FIGS. 8A to 8C, to limit the double layer capacitive effect during application of the command signal onto the working electrode 10 (as shown in FIG. 1), an impulse 78 (shown in FIG. 8B) can be added to the command signal (shown in FIG. 8A) to charge more quickly the electric capacitance associated to the double layer and thus to limit the delay relative to the decrease of the capacitive current. FIG. 8C shows the resulting command signal 80.

Figure 7:
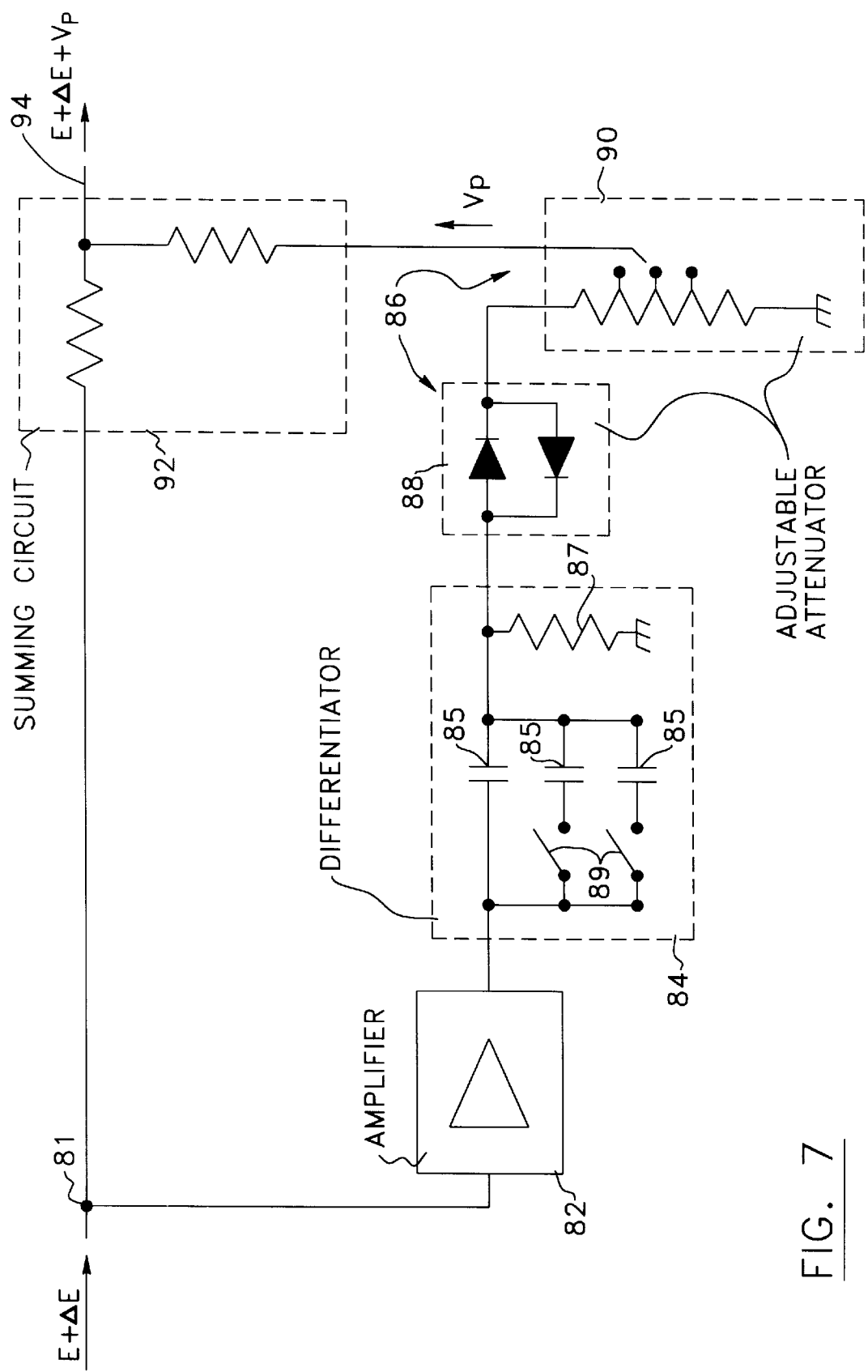
FIG. 7 is a schematic diagram of an impulse superimposing circuit according to the invention.

Referring to FIG. 7, there is shown an example of a circuit for generating an impulse of a short duration (having an amplitude around three times the value of $\Delta E$ and an approximative duration of 0.05 to 1 ms) from the command signal $E+\Delta E$, in synchronicity therewith, and for adding it to the command signal E +ΔE. The circuit in question has an input 81 for receiving the command signal E+ΔE from the signal generator 4 (shown in FIG. 1). The command signal is transmitted to an amplifier 82, and then derived by means of a differentiator 84. At this stage, the obtained impulse has a high amplitude compared to ΔE. Only the upper part of the high amplitude impulse is kept to minimize the noise generated by the amplifier 82. This is achieved by means of an adjustable attenuator 86 including a set of diodes 88 and a variable resistor 90 permitting adjustment of an amplitude of the effective impulse $V_p$. The conjunction of the amplifier 82 with the attenuator 86 permit to minimize the threshold effect of the diodes 88. The signal $V_p$ produced by the attenuator 90 is added to the command signal E+ΔE by means of a summing circuit 92 to produce the signal E+ΔE+$V_p$ at an output 94 of the impulse generator 6 (as shown in FIG. 1), where the impulse $V_p$ gets superimposed to a leading edge of each pulse in the command signal E+ΔE. The differentiator 84 may include a set of selectable capacitors 85 (and/or resistors 87) having different values (properties) to adjust the time constant τ (equal to RC) of the differentiator 84 and thus the duration of the impulse, depending on the desired effect as shown in FIG. 8B. This can be easily achieved with switches 89 arranged to select the capacitors 85 in circuit. It should be understood that any other suitable impulse generating circuit could be used rather than the above described embodiment.

Figure 9:
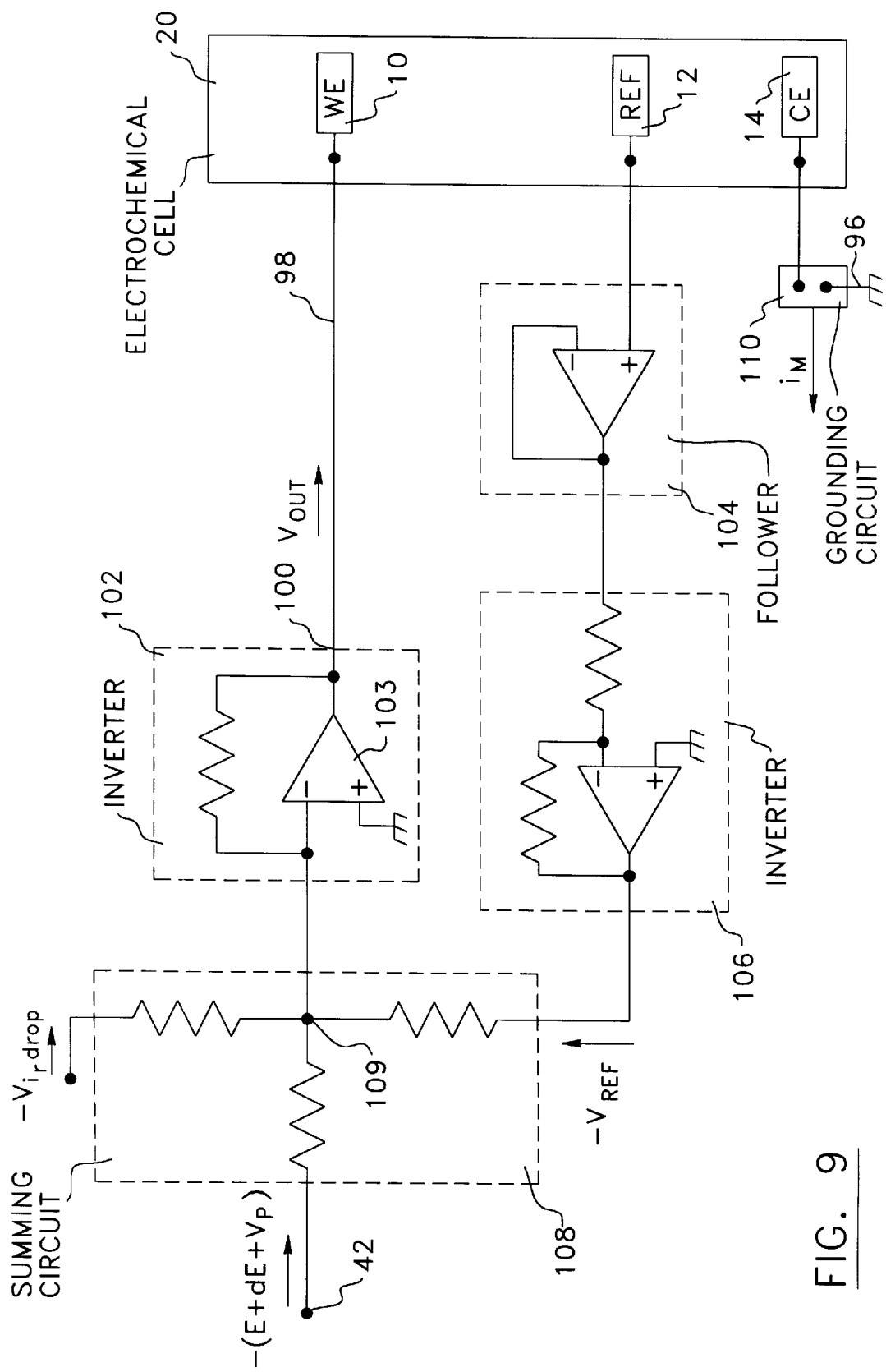
FIG. 9 is a schematic diagram of a potentiostat for an electrochemical cell having one working electrode, according to the invention.
Figure 10:
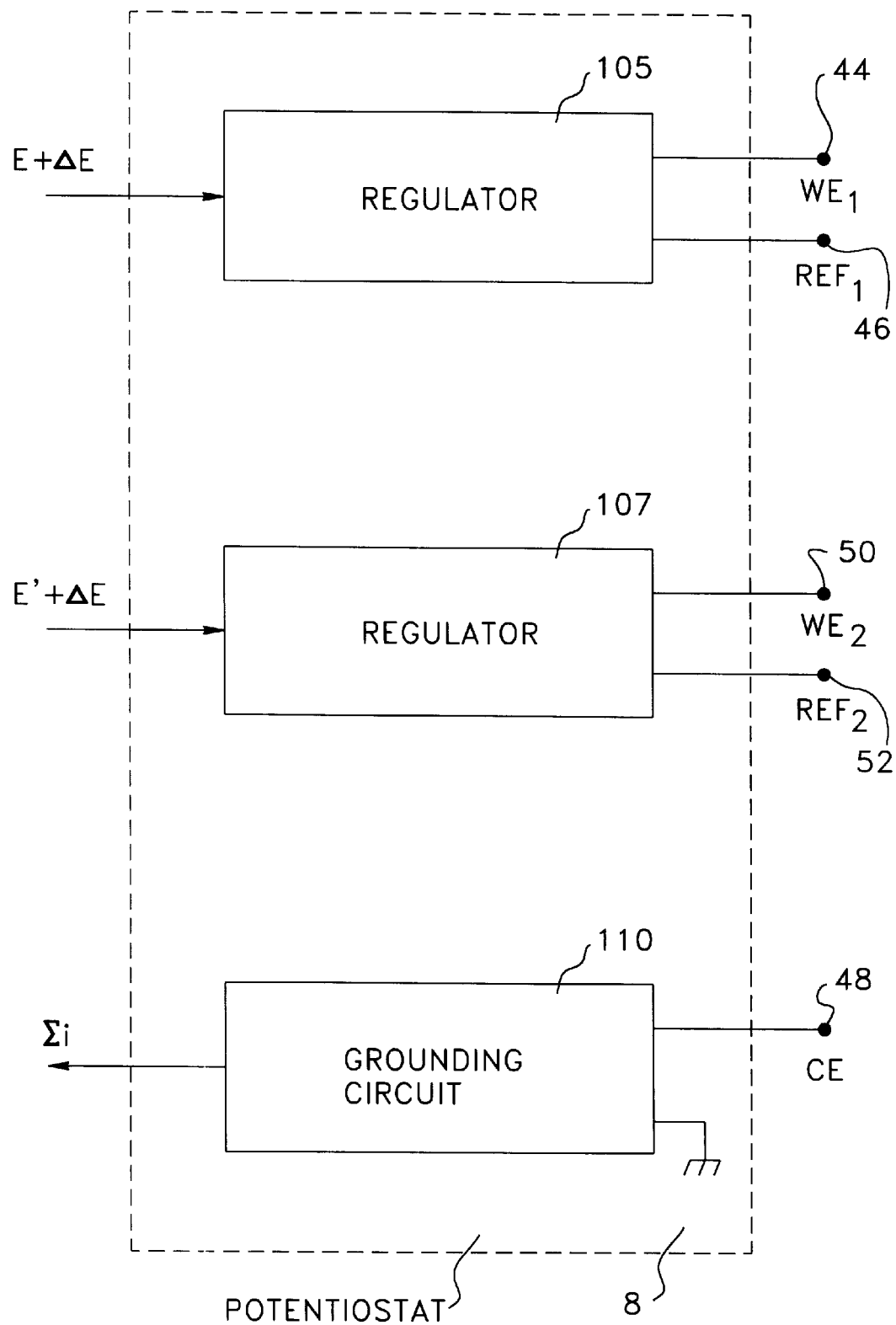
FIGS. 10 and 11 are schematic diagrams of potentiostats for an electrochemical cell having two working electrodes, according to the invention.
Figure 11:
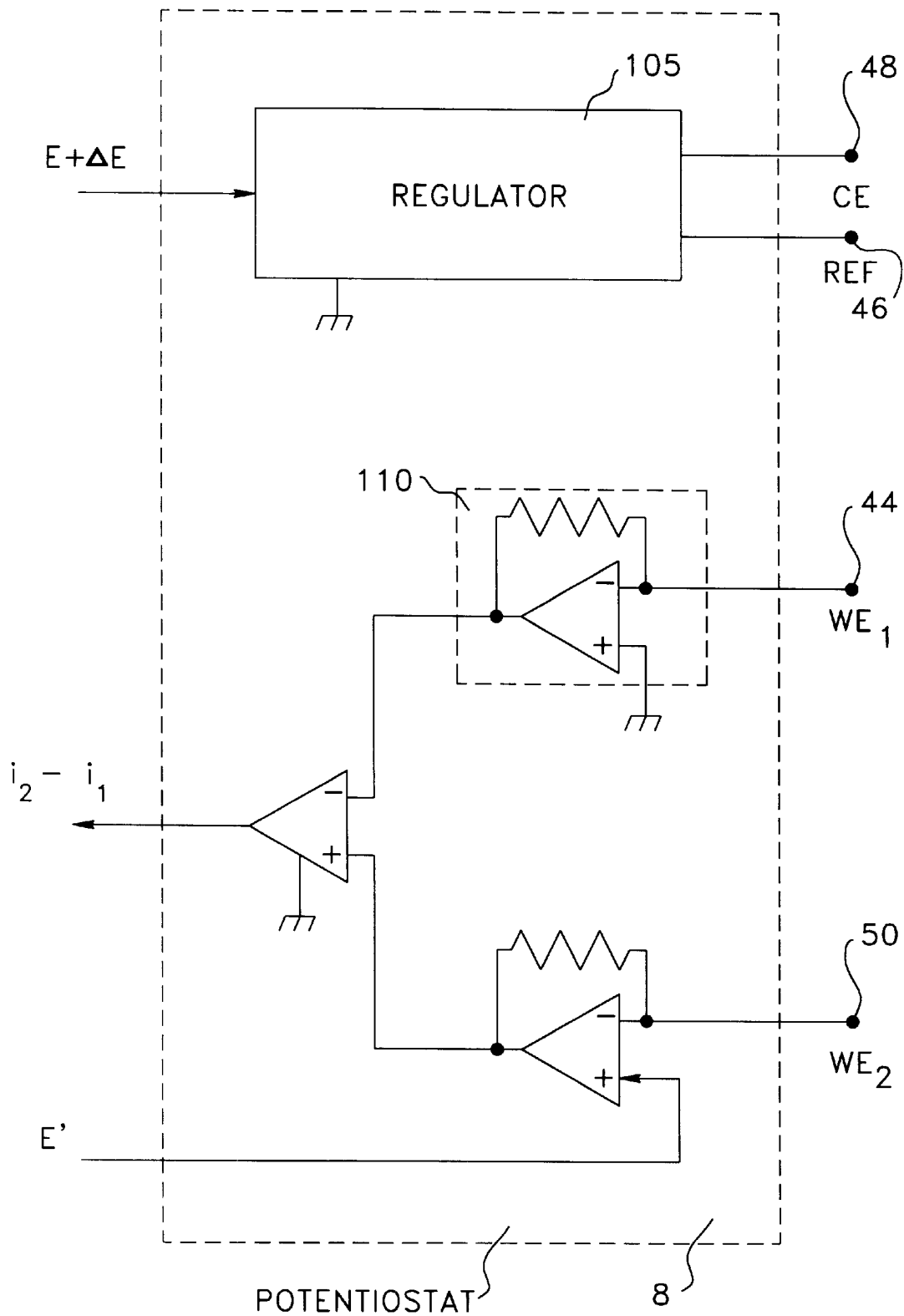

Referring to FIG. 9, three electrodes 10, 12, 14 permit to impose a potential and to measure a resulting current. They are in contact with the solution to be analyzed in the electrochemical cell 20. These electrodes are: the working electrode (WE) 10 (e.g. drop of mercury, solid electrode covered with mercury or not or a film having selective properties, microelectrodes, etc.), the reference electrode (REF) 12, and the auxiliary or counter electrode (CE) 14 (e.g. generally an inert surface of platinum). The potential applied onto the working electrode 10 is the potential that the electrode/solution interface receives with respect to the surrounding solution. This applied potential refers to the potential of the reference electrode 12 whose value remains steady and fixed. The applied potential $E_{WE}$31 $E_{REF}$ must therefore be forced to follow the value of the imposed potential (E+ΔE+$V_p$), which amounts to carry out a potential regulation. In the present system of electrodes, the counter electrode 14 is only used for current flow. According to an aspect of the invention, the counter electrode 14 is connected to ground 96, which provides a shielding effect in the electrochemical cell 20. The current measurement is achieved in the ground return of the counter electrode 14 and thus presents the advantages of a virtual ground without affecting the part of the regulating circuit of the working electrode 10, which thus provides a good stability. The inverted structure of the potential imposition and regulation circuit which is herein presented is not more complex than those found in the prior art. However, it provides many advantages, considering that the working electrode 10 is the sensible point because this is the potential imposed at this point that determines the whole of the electrochemical events which are produced between the electrodes 10, 12, 14 and the species in solution. Generally, the working electrode 10 is sensible to capacitive effects in the (shielded) linking cable 98 that connects the potentiostat 8 to the electrode 10 in the electrochemical cell 20. This linking cable 98 may have a length exceeding 1 meter. It introduces inevitably parasitic capacities. The presently described circuit causes the parasitic capacities derived from the cable 98 to have less disruptive effect because they are produced at the output 100 of the operational amplifier 103 driving the working electrode 10 in comparison with the prior art systems where they are introduced on the virtual ground formed by the working electrode. Another advantage of the present circuit resides in that the counter electrode 14 virtually connected to ground 96 is used as a shield and thus prevents electric originating noise which would affect the working electrode 10. This advantage becomes very important when considering that in practice, the counter electrode has an important metallic mass with respect to the working electrode which is much smaller. Furthermore, due to its important contact with the solution which is conductive, the shielding effect is increased. Another advantage of the present circuit with respect to the prior art concerns the current measurement $i_M$ carried out between the counter electrode 14 and the ground 96. In the present case, this measure can be achieved using any suitable circuit adapted for this purpose. This measure cannot in any case affect the potential imposing circuit. Indeed, if a perturbation is introduced by a current measuring circuit, it will affect the value $V_{ref}$, i.e. the floating potential of the reference electrode 12. This perturbation is taken into account by the proposed regulating circuit where the value $V_{ref}$ is added at point (A). Thus, the perturbation does not affect the difference between the value $V_{ref}$ and the value E +ΔE +$V_p$+$V_{ref}$ imposed on the working electrode 10. This provides a new method with respect to the prior art associated to electroanalytical measurements. Indeed, the present circuit permits the operation of a system of electrodes consisting of several working electrodes WE, by means of a number of regulating circuits 105, 107, with a single common counter electrode as shown in FIGS. 10 and 11.

The regulation consists of adding the floating potential $E_{REF}$ of the reference electrode (REF) 12 to the input potential E+ΔE+$V_p$. The resulting potential is imposed to the working electrode (WE) 10. To this effect, the potentiostat 8 has an input 42 for receiving the command signal −(E+ΔE+$V_p$) derived from the impulse generator 6 (shown in FIG. 1). The input 42 is connected to a summing circuit 108 for adding the signal −$V_{REF}$ (and optionally the signal −$V_{ir\ drop}$ returned by the current to voltage converter 22 shown in FIG. 1) to the incoming command signal at point 109 of the summing circuit 108. The resulting signal at point 109 is inputted into an inverter 102 and then imposed onto the working electrode (WE) 10. The signal $V_{REF}$ provided by the reference electrode (REF) 12 is adapted in impedance by the follower 104 and then inverted by the inverter 106 to provide −$V_{REF}$ to be added to the other signals at the point 109 by means of the summing circuit 108. The current measurement ($I_M$) is carried out between the counter electrode (CE) 14 and the ground 96, by means of a grounding circuit 110 devised for this purpose.

Referring to FIGS. 12A to 12E, the current $i_M$ flowing from the counter electrode 14 in response to the potential step ΔE combined with the impulse $V_p$, consists of a combination of capacitive current $i_C$ and a faradic current $i_f$ to be measured. The purpose of the current to voltage converter 22 (shown in FIG. 1) is to amplify the faradic current $i_f$ with a maximum of sensibility. The validation signal $\overline{SW}$ is used to distinguish two parts of the current flowing from the counter electrode 14. The first part is of a capacitive nature. Since it is influenced by the impulse $V_p$ combined with the potential step ΔE, the value of this current is high and requires little amplification. The second part of the current is of a principally faradic nature and is clearly lower than the previous one. Its measurement requires a high amplification because it is the most significant part that will be processed later. Furthermore, this permits correction (compensation) of the ohmic drop $i_r$ (drop) during the validation $\overline{SW}$ and will be used to accelerate the double layer charge. To achieve this, $v_{i_{r\,drop}}$ is added at the level of the potentiostat 8 to the command signal E+ΔE combined with the impulse $V_p$.

Figure 12A:
FIGS. 12A to 12E are graphs showing the command, control, output, capacitive component and faradic component signals for a current to voltage converter according to the invention.
Figure 12B:
Figure 12C:
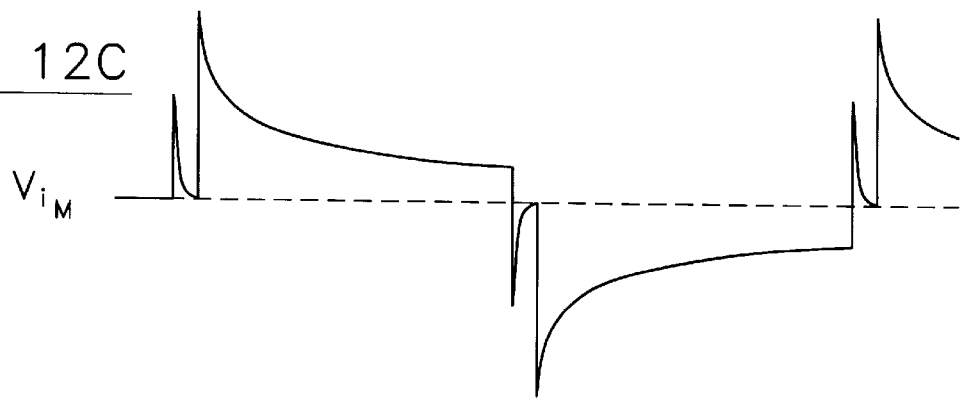
Figure 12D:
Figure 12E:
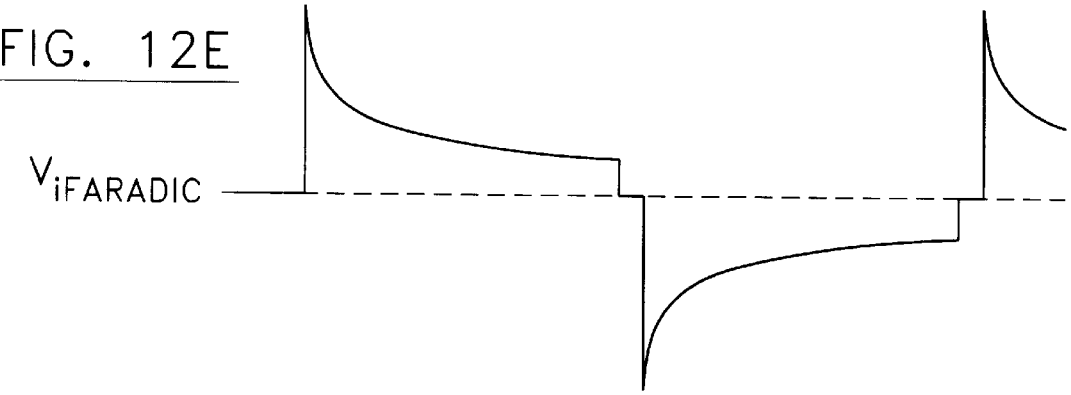
Figure 13:
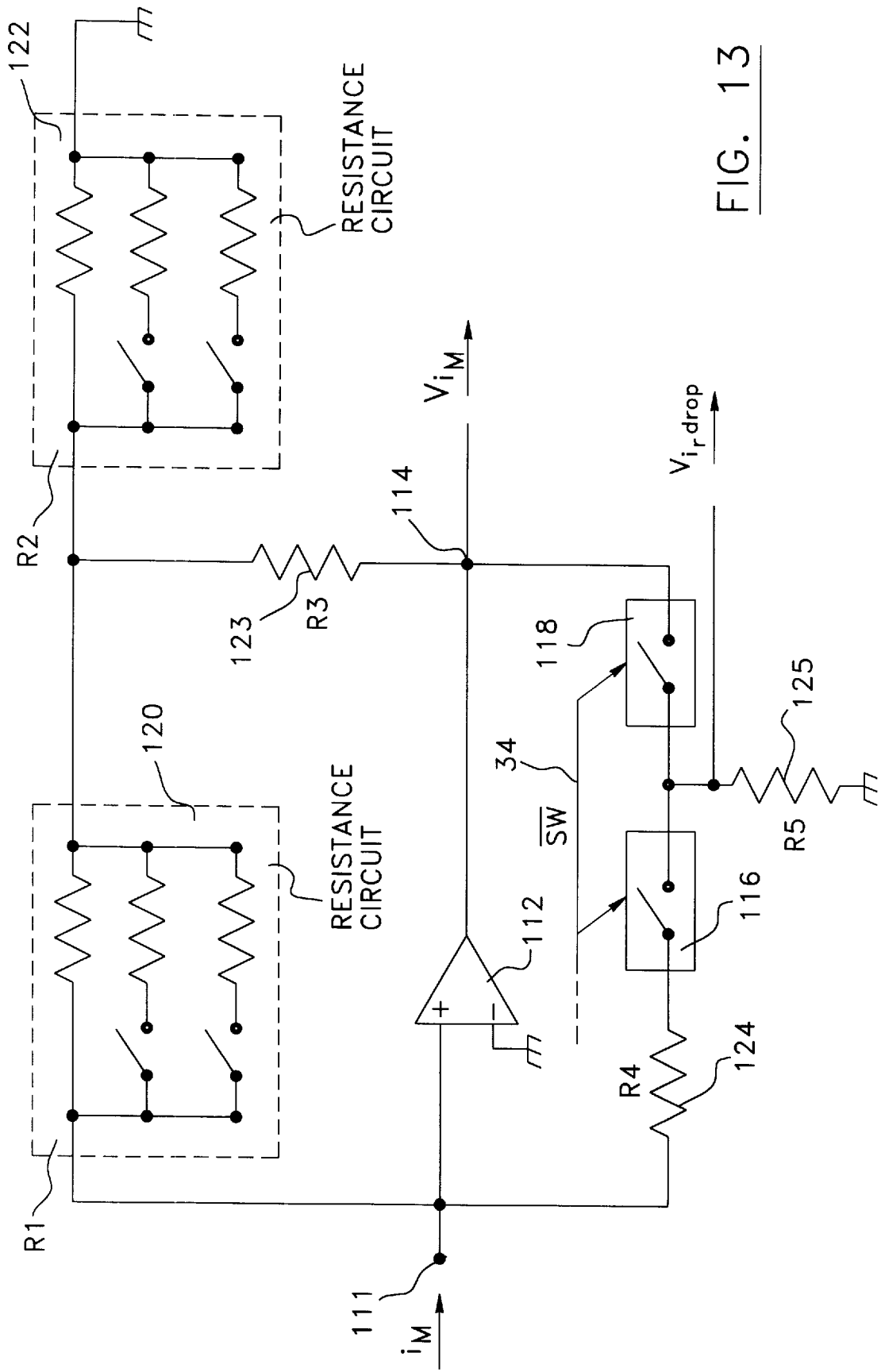
FIG. 13 is a schematic diagram of a current to voltage converter with capacitive control, according to the invention.

Referring to FIG. 13, there is shown an example of an electronic circuit to form the voltage to current converter 22 shown in FIG. 1, which also acts as the grounding circuit 110 shown in FIG. 9. The voltage to current converter 22 has an input 111 for receiving the current signal $i_M$ derived from the counter electrode 14 connected to the potentiostat 8. The input 111 is connected to a current to voltage converter formed by an operational amplifier 112 whose gain depends on the state of the control signal $\overline{SW}$ as shown in FIG. 12B. The operational amplifier 112 has an output 114 for producing a voltage signal $V_{im}$ as shown in FIG. 12C. Two circuit branches are connected in parallel with the operational amplifier 112, one branch including the sets of resistors 120, 122 (R1, R2) and resistor 123 (R3), the other branch including resistor 124 (R4) and switches 116, 118 responsive to the control signal $\overline{SW}$ provided on the control line 34 connected to the controller 2 as shown in FIG. 1. When the control signal $\overline{SW}$ causes the switches 116, 118 to be opened (during most of the time when $\overline{SW}$ is high, as shown in FIG. 12B), the amplifier 112 has a high gain, determined by the resistance values of the two sets of resistors 120, 122 (R1, R2) provided for gain adjustment purposes. The set of resistors 120 (R1) controls the principal amplification gain range whereas the set of resistors 122 (R2) controls the intermediary amplification gain range. It is in that case that the current to voltage converter 22 has maximum sensitivity to convert the faradic current $i_f$ to be measured. $V_{im}$ is given by:

$$V_{I_M} = -(R1 \times i_M) \times \left( \frac{R2 + R3}{R4} \right)$$

The voltage $v_{i_r\,drop}$ on the side o the resistor 125 (R5) connected between the switches 116, 118 is null when they are opened.

When the control signal $\overline{SW}$ is low, the switches 116, 118 are closed and $i_M$ passes essentially across the resistor 124 (R4) to the detriment of the set of resistors 120 (R1) because the resistor 124 (R4) has a much smaller value than the set of resistors 120 (R1). The amplification gain is low and depends on the resistor 124 (R4). This time, the voltage to current converter 22 has a low sensitivity to convert the portion of the current that represents the capacitive current ($I_C$) and which is used as a compensating element $V_{ir\,drop}$ which is fed back to the potentiostat 8 that adds the signal $V_{ir\,drop}$ to the command signal E+ΔE+$V_p$ for a predetermined time period (depending on $\overline{SW}$) at each transition of the pulses ΔE. In this case, $v_{i_M}$ is given by:

$$V_{i_M} = -(i_M \times R4) = V_{i_r\,drop}$$

Referring to FIG. 1, a low pass filter 24 can be added between the current-to-voltage converter 22 and the integrator circuit 26. The filter 24 may conveniently be arranged with a switch 25 responsive to the control signal $\overline{SW}$ provided on the control line 34, to temporarily maintain the signal $V_{i_M}$ during transitions of the pulses ΔE to prevent the filter 24 from being affected by fast and important transitions occurring during $\overline{SW}$ that would impose too long a recovery time to the filter 24. Preferably, the filter 24 is of a second or fourth order and eliminates possible noise in the 1 ms time scale or less.

Figure 14:
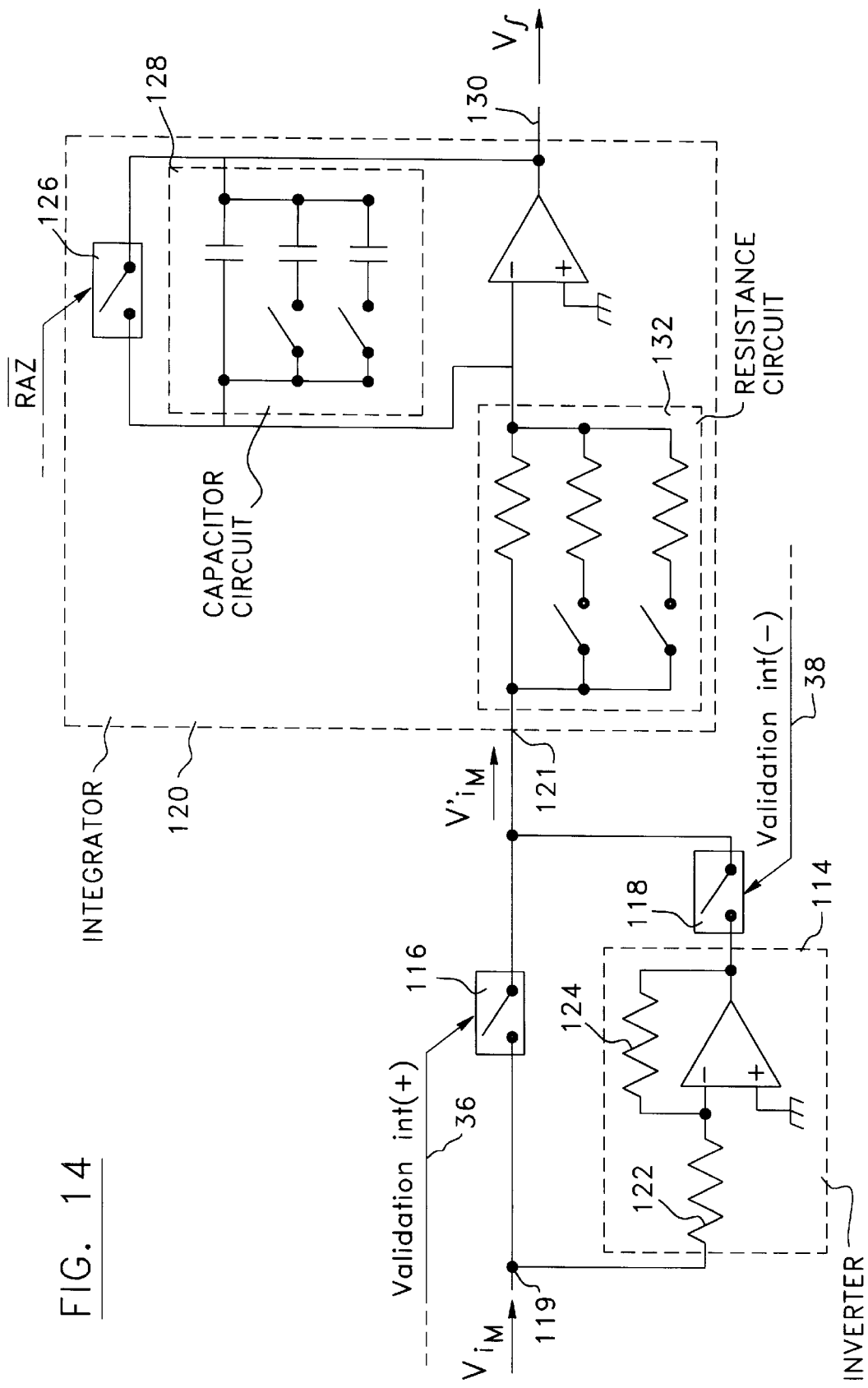
FIG. 14 is a schematic diagram of an analog integrator circuit arrangement according to the invention.
Figure 15:
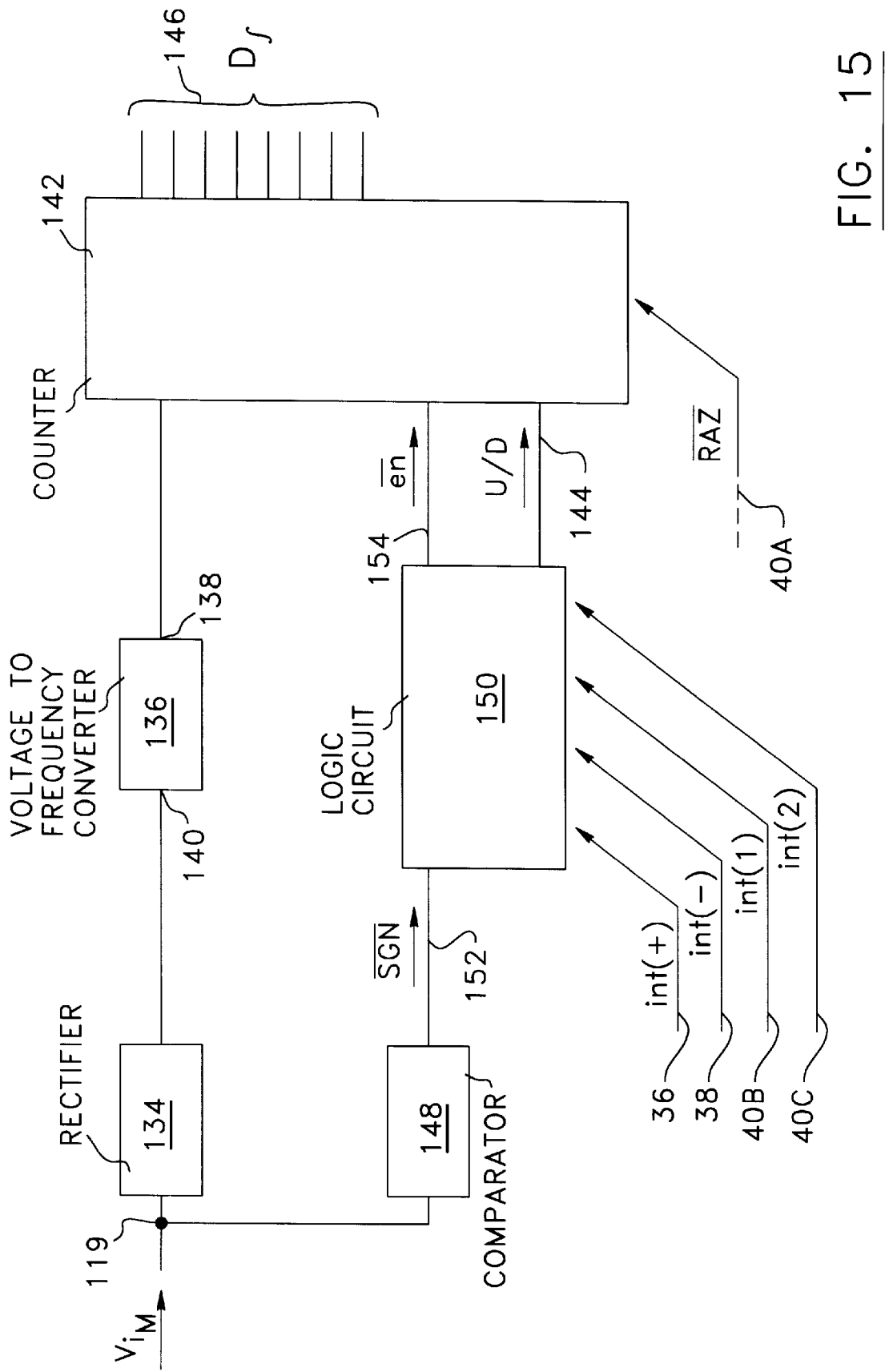
FIG. 15 is a schematic diagram of a digital integrator circuit arrangement according to the invention.

Referring to FIGS. 14 and 15, the current derived from the electrodes $i_M$ in response to the potential step ΔE after being processed by the current to voltage converter 22 is integrated to attenuate the noise and to facilitate electronic algebraic operations. In this respect, the integrator circuit 26 (shown in FIG. 1) takes advantage of the particularity relative to the operation of integration that has an effect of smoothing the result. The most notable effect is the rejection of harmonic interferences having a period that is a multiple of the integration step. The latter is preferably chosen so that the interferences originating from the grid supply are eliminated. Furthermore, the polarity of the period to integrate will be taken into account during this operation depending on the selected mode of integration. The integration can be carried out numerically or analogically.

Despite the relative simplicity of an analog integrator, the flaws of this type of integrator are serious. They are principally the drift of the output signal due to current leakage that provokes a discharge of the integrator's capacity, and the low dynamic of the output signal which is limited to the maximum supported by the operational amplifier of the integrator circuit. Numeric integration allows to overcome these drawbacks and to expand the application limits. However, it should be understood that an analog integrator may still suit the need and be used instead of a numeric integrator.

Referring to FIG. 14, there is shown an example of an electronic circuit to form an analog integrator circuit. The integrator circuit has an input 119 for receiving the signal $V_{i_M}$ derived from the current to voltage converter 22 (shown in FIG. 1). The signal $V_{i_M}$ is transmitted to a unitary gain inverter 114 (resistors 122, 124 are equal) depending on whether the switch 116 or the switch 118 is closed. The switches 116, 118 are controlled respectively by the control signals int(+) and int(−) provided on control lines 36, 38. These control signals are not applied simultaneously, so the switches 116, 118 cannot be closed at the same time. When the switch 116 is closed, the switch 118 is opened and the signal $V_{i_M}$ is transmitted directly to the input 121 of the integrator 120 ($V'_{i_M}=V_{i_M}$). When the switch 118 is closed, the switch 116 is opened and the signal $V_{i_M}$ is transmitted to the inverter 114, and then to the input of the integrator 120 ($V'_{i_M}=-V_{i_M}$). This simple circuit permits to carry out an addition or a substraction of the electrochemical response $V_{i_M}$ within the integrator 120.

The integrator 120 has a switch 126 responsive to the $\overline{RAZ}$ signal provided on control line 40 from the controller 2. The closing of the switch 126 causes the resetting of $V_{17}$ at an output 130 of the integrator 120 and the discharge of the capacitors in the capacitor circuit 128. The reset should be carried out immediately after the sampling of the integrated response (by the memorization circuit 28 shown in FIG. 1). When the switch 126 is opened, the integrator 120 integrates the signal $V'_{i_M}$ that provides $V_f$ at the output 130 according to:

$$V_f = \frac{1}{RC} \int V'_{I_M} dt$$

during the period where $\overline{RAZ}$ leaves the switch 126 opened. The integrating capacity is adjusted by the selection of the resistors in the resistance circuit 132 and the capacitors in the capacitor circuit 128 of the integrator circuit 120. The components should be selected for precision, stability, low noise, etc. (e.g. metal ribbon resistors with a 1% tolerance).

Referring to FIG. 15, there is shown an example of an electric circuit to form a digital integrator circuit. The integrator circuit has an input 119 for receiving the signal $V_{i_M}$ from the current-to-voltage converter 22. The signal $V_{i_M}$ is transmitted to a rectifier 134 that transforms it into its own absolute value. The resulting absolute signal is transmitted to the input 140 of a voltage-to-frequency converter 136 producing at its output 138 a frequency signal having a frequency proportional to the voltage of the signal at its input 140. This frequency signal is then transmitted to a counter 142 that counts up or down the pulses in the frequency signal depending on the logic signal U/D on control line 144, and produces at its output 146 a value $D_f$ which represents the integrated value of the signal $V_{i_M}$ under a numeric form. The signal $\overline{RAZ}$ provided on control line 40A from the controller 2 (shown in FIG. 1) permits to reset the output value $D_f$.

The signal $V_{i_M}$ at the input 119 of the integrator circuit is also transmitted to an analog comparator 148 to determine its polarity with respect to a reference signal (e.g. zero reference) selected to this effect. The analog comparator 148 produces a logic signal $\overline{SGN}$ indicative of the polarity of the signal $V_{i_M}$, which is transmitted to a logic circuit 150 via line 152. The logic circuit 150 comprises a set of logic functions that permit to control the counter 142 with respect to the control signals int(+), int(-) on control lines 36, 38, the signal $\overline{SGN}$ and optional additional control signals int(1) and int(2) on lines 40B, 40C. The two latter control signals int(1) and int(2) may be used depending on the selected integration mode. The logic circuit 150 transmits to the counter 142 the logic signals U/D and $\overline{en}$ on lines 144 and 154 respectively. The signal $\overline{en}$ activates or blocks the counting function of the counter 142. The signal U/D activates the up or down counting of the pulses, which amounts to carrying out an addition or a substraction of the electrochemical response $V_{i_M}$ within the integrator circuit.

The principle of the numeric integration thus consists of converting the input voltage $V_{i_M}$ into a proportional frequency signal and then counting the pulses during a given time. The signal $D_f$ at the output 146 of the counter 142 represents the integrated value of the input signal $V_{i_M}$. However, this alone would not allow the processing of a negative input signal because the voltage-to-frequency converter cannot generate negative frequencies.

The astuteness consists of adapting the counting process as follows: (i) the input signal $V_{i_M}$ is beforehand converted into an absolute value prior to its transmission to the voltage to frequency converter 136, and (ii) the determination of the polarity of the input signal $V_{i_M}$ permits to configure the counter in up or down counting mode. This thus provides a numeric integration that considers the polarity of the input signal $V_{i_M}$.

Figure 17A:
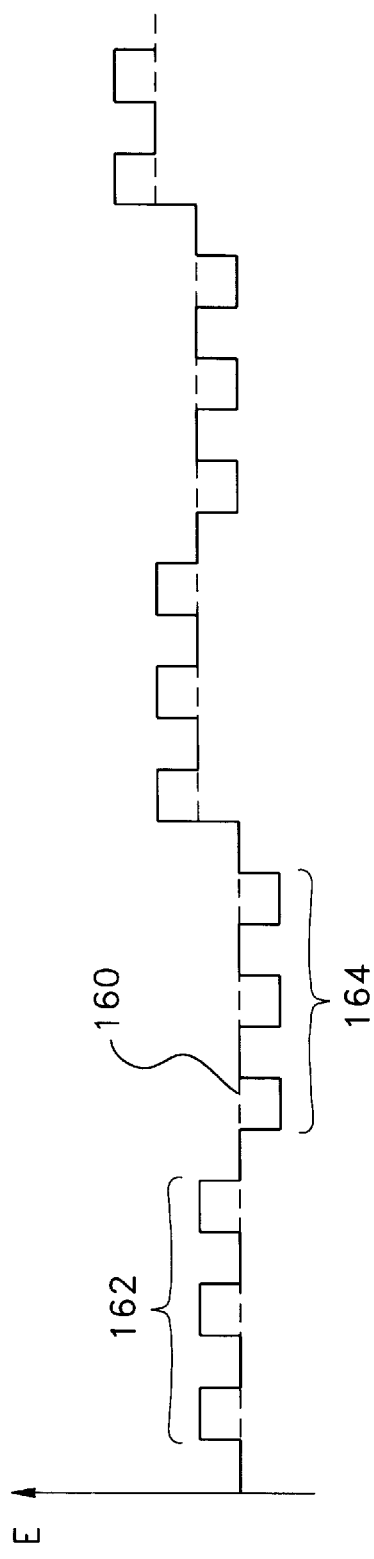
FIGS. 17A to 17C are graphs showing the command, integrated response and full scan signals in MSWV-DD, according to the invention.

Referring to FIG. 1, according to an aspect of the invention, there is provided a multiple waveform voltammetric method that can be carried out with the above described instrument. The method is for electrochemical analysis of species in an electrolyte solution contained in an electrochemical cell 20 having a system of electrodes 10, 12, 14 (and optionally 16, 18) in contact with the electrolyte solution. The first step of the method consists of applying a variable potential excitation signal between two of the electrodes (e.g. electrodes 10, 12) to produce an electrochemical reaction in the electrolyte solution. As shown in FIG. 17A, the excitation signal includes a DC bias potential 160 increasing cyclically by a potential step to form a potential staircase signal sweeping across a predetermined potential domain, and at least one pair of successive pulse trains 162, 164 of opposite polarity per potential step, the pulse trains 162, 164 being superimposed on the DC bias potential 160. The second step of the method consists of measuring an electric current derived from a diffusion flux of ions through the electrolyte solution towards one of the electrodes (e.g. the working electrode 10) as a result of the excitation signal applied in the first step. The electric current measured in the second step is characteristic of the species in the electrolyte solution, thereby providing for electrochemical analysis thereof. It has been found that the succession of pulse trains having opposite polarity improves the precision of the electrochemical measurement.

Figure 17B:
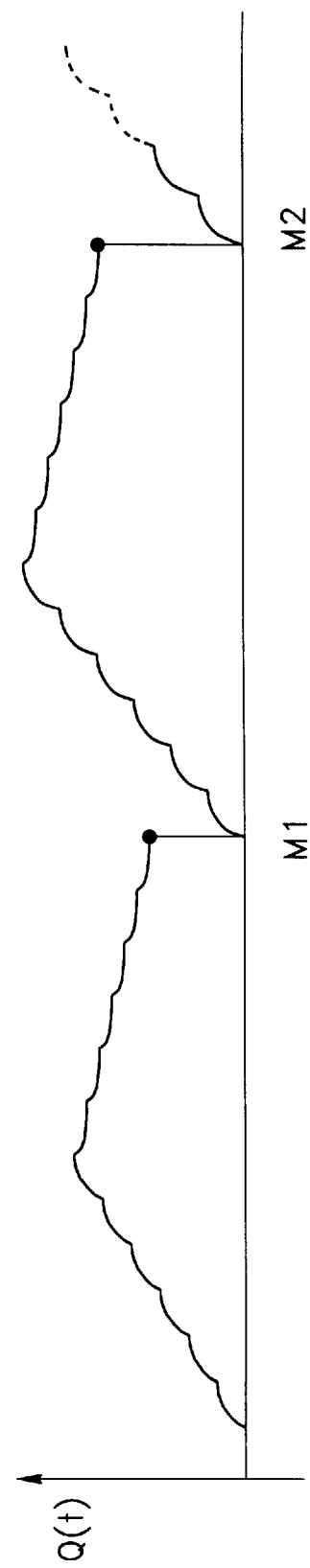
Figure 17C:
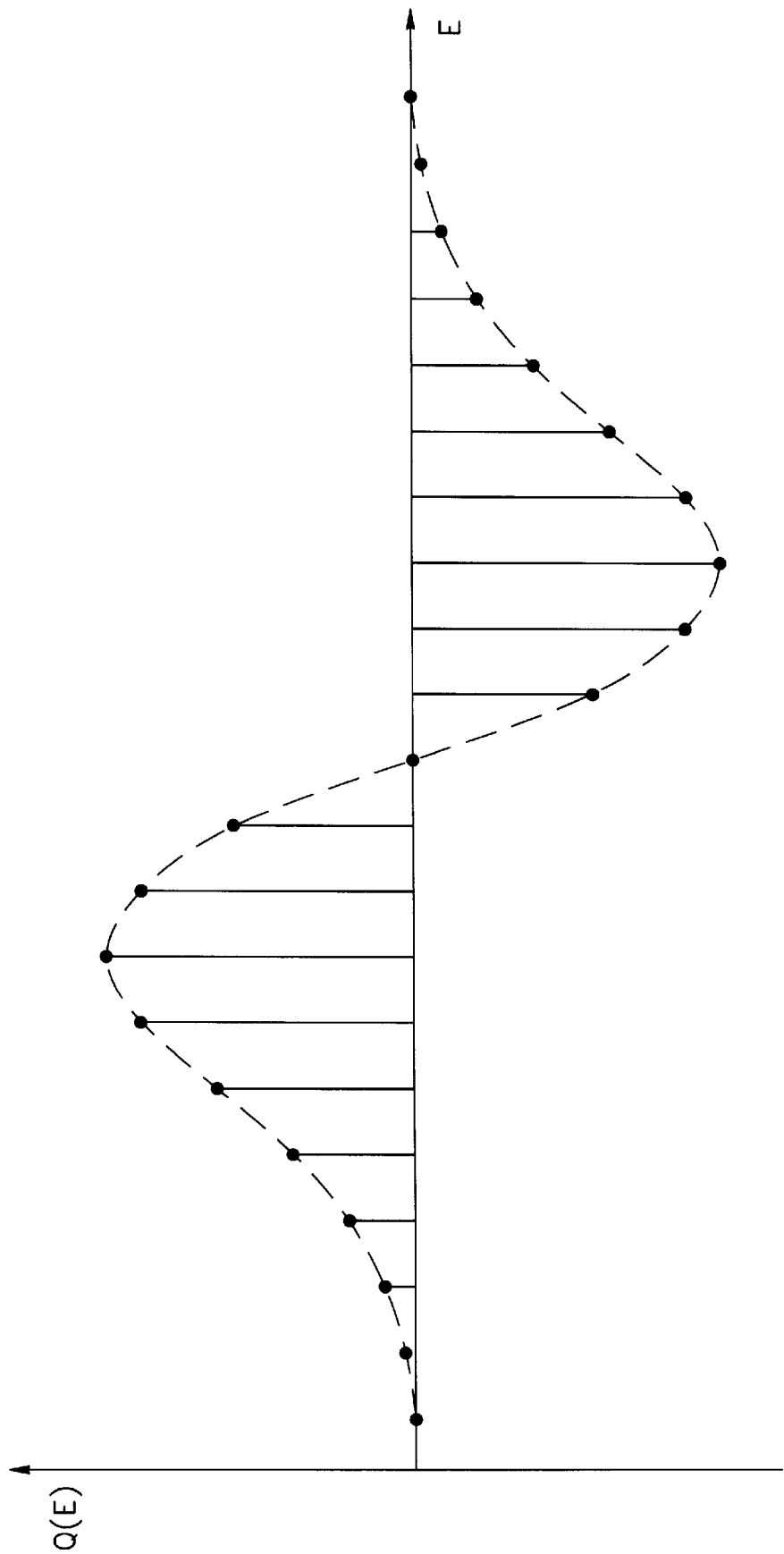

The precision of the measurement can be further improved with the additional steps consisting of time-integrating the electric current to produce an integrated current response as shown in FIG. 17B, where addition and subtraction operations are performed, in time, on the integrated current response to reduce noise effects in the electric current. FIG. 17C shows the whole integrated response formed by taking samples $M_1$, $M_2$, etc. from the integrated current response shown in FIG. 17B. The method can be applied using any type of potentiostat (e.g. for three electrodes or two). The polarity of the measured signal must be considered in the integration step.

The same results can be obtained by replacing the above mentioned first step by the step consisting of applying two variable potential excitation signals between two respective pairs of the electrodes (e.g. electrodes pairs 10, 12 and 16, 18) to produce an electrochemical reaction in the electrolyte solution. In that case, as shown in FIG. 16D, each one of the excitation signals includes a DC bias potential 166 increasing cyclically by a potential step to form a potential staircase signal sweeping across a predetermined potential domain, and a pulse train 168 per potential step, the pulse train 168 being superimposed on the DC bias potential 166. For this purpose, the instrument may be provided with additional signal and impulse generators 5, 7, as shown in FIG. 1. Both excitation signals vary inside adjacent potential ranges. To achieve this, the DC bias potentials 166 of the excitation signals may have DC levels showing a potential difference corresponding substantially to an amplitude of the pulse train 168. Or the DC bias potentials 166 of the excitation signals may have substantially similar DC level while their pulse trains 168 have opposite polarity. This method can be applied using a potentiostat as shown in FIG. 10, with a double regulator system 105, 107 and a current measurement in the common counter electrode 14 (thus necessarily the sum of the currents ($\Sigma i$) in response to the excitation signals E+$\Delta$E and E'+$\Delta$E with E-E'=$\Delta$E). This configuration is the most complex one and provides more extension possibilities especially if the currents are measured independently in the regulators 105, 107. Instead of using DC bias potentials E and E' having different values, they can be set equal provided that the perturbations $\Delta$E in the regulators 105, 107 have opposite polarity, e.g. $\Delta$E for the regulator 105 and -$\Delta$E for the regulator 107.

FIG. 11 shows an example of a grounding circuit 110, using the inherent characteristic of an operational amplifier in a noninverting configuration, thus working to keep the input voltages equal so that the cell current $i_M$ is supplied by the operational amplifier to maintain this condition.

The method can also be applied using a potentiostat as shown in FIG. 11, with a single regulator 105 (for two or three electrodes) and two electrodes 14, 16 maintained at distinct potentials E and E-E'. In this case, the perturbation $\Delta$E is identical and it is therefore necessary to measure a difference of the currents ($i_2-i_1$) of each electrode 14, 16.

The above two methods (with one and two working electrodes respectively) can be used combined together. In all these cases, the measurement is carried out after N×k perturbations ΔE (N being the number of pulses in a pulse train 162, 164, 168, k being the number of pulse trains 162, 164, 168 per potential step) by memorization of the last cumulative value on the integral just before its reset and the increment of E (step function) for the next measurement. This action must be achieved during the last fraction of the last N×k periods. The memorization can be carried out by means of a memorization circuit 28 as shown in FIG. 1, formed for example of a sample and hold circuit connected to the output 146 of the integrator circuit 26.

With the present instrument, three different integration modes can be used to sample the signal $V_{i_M}$. These modes influence the functioning of the numeric integrator circuit 26 (detailed in FIG. 15) by means of the control signals int(+), int(−), int(1) and int(2). The following description explains the various modes with respect to the processing of the electrochemical signal. Int(+) is a control signal in the numeric integrator circuit. It represents also the integration period of the current $i_M$ in an electrochemical point of view.

The integration modes herein proposed lie within the scope of the passage between the sampling of a current point as done by the prior art and the manner to sample made possible with the present circuits of electronic nature.

Figure 16A:
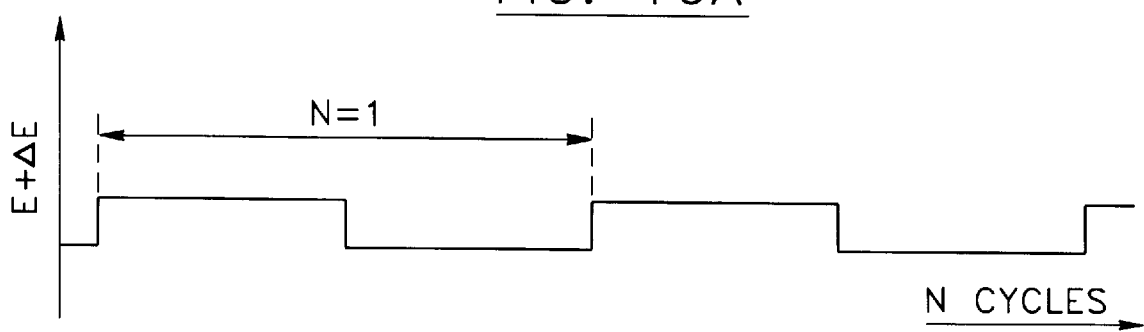
Figure 16B:
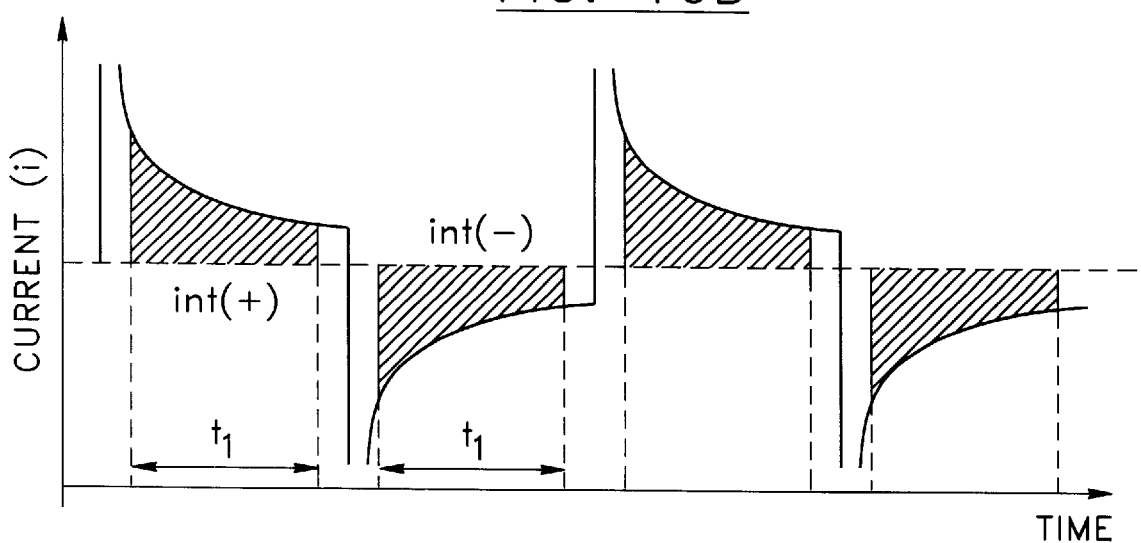
Figure 16C:
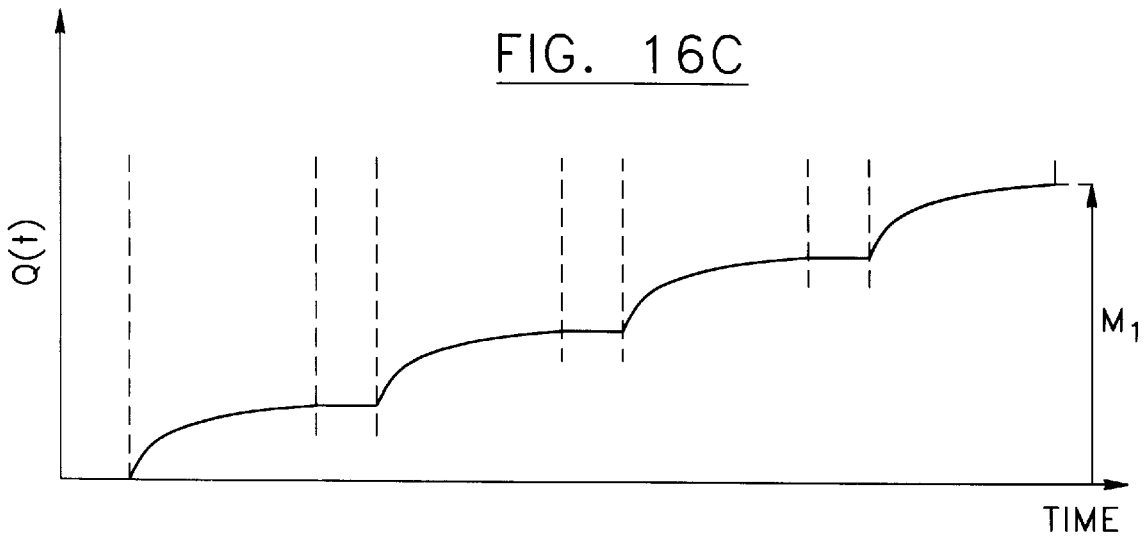

Referring to FIGS. 16A and 16B, the first integration mode, called "simple sampling" (SS), consists of integrating the voltage signal $V_{i_M}$ during a predetermined discrete time period $t_1$ between transitions of the pulses, taking into account the polarity of the current $i_M$. FIG. 16A shows the command signal E+ΔE as a function of the period duration of the cycles, and FIG. 16B shows the variation of the current derived from the electrochemical cell as a function of time for the SS integration mode. The time $t_1$, during which the integration is carried out, and the integrating areas int(+) and int(−) correspond to the following operations:

$$int(+) = \int_{t_1} i_{(E+\Delta E)} dt$$

$$int(-) = \int_{t_1} i_{(E)} dt$$

and the measurement in integration mode SS is the result of the following operation:

$$\text{Measurement} = \sum_N [int(+) - int(-)]$$

as shown in FIG. 16C. FIG. 16E shows the whole response (full scan) obtained by sampling the integrated response after each potential step of the staircase (as shown in FIG. 16D), to provide samples $M_1$, $M_2$, etc. The overall response results from the summing action of the integrator circuit 26 (shown in FIG. 1): making sums at each potential step of the individual responses corresponding to +ΔE perturbations and −ΔE perturbations respectively.

Figure 18A:
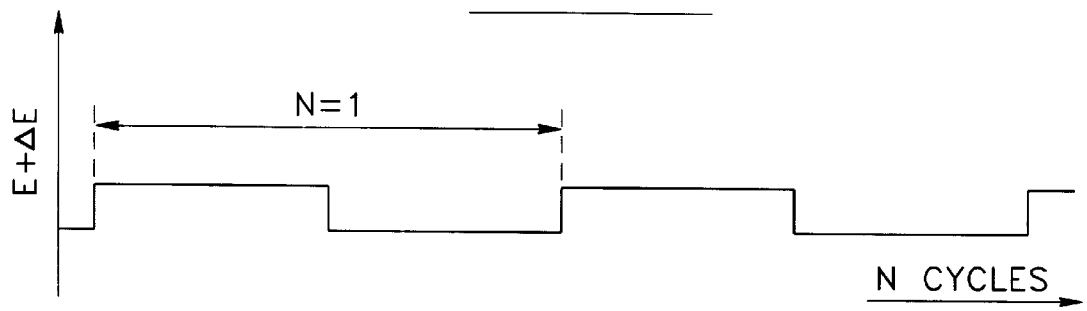
FIGS. 18A to 18D are graphs showing the command signal, the double sampling and interlaced modes of integration, and a corresponding integrated response signal according to the invention.
Figure 18B:
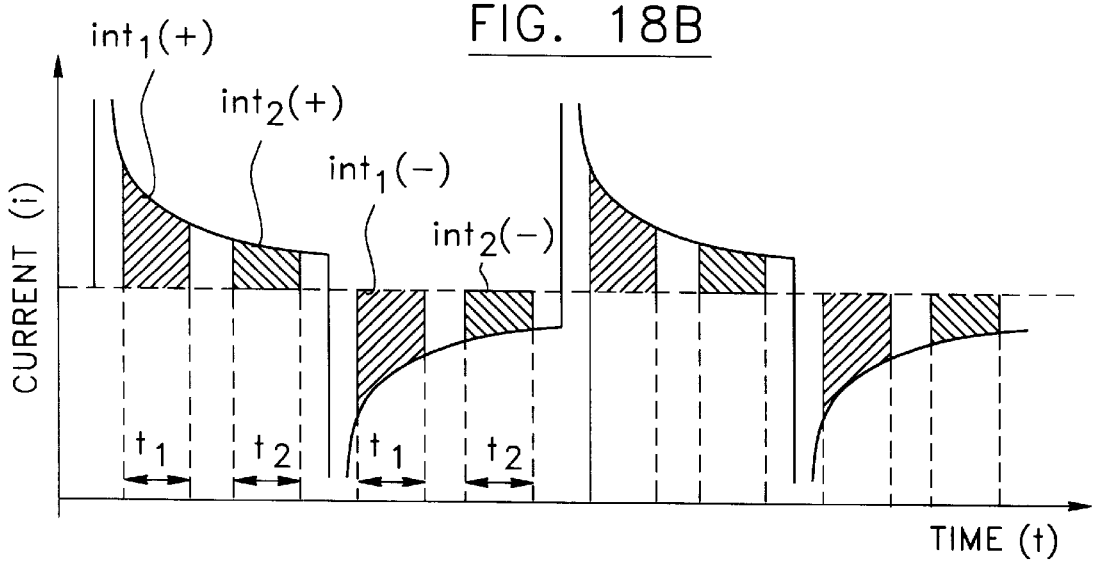
Figure 18C:
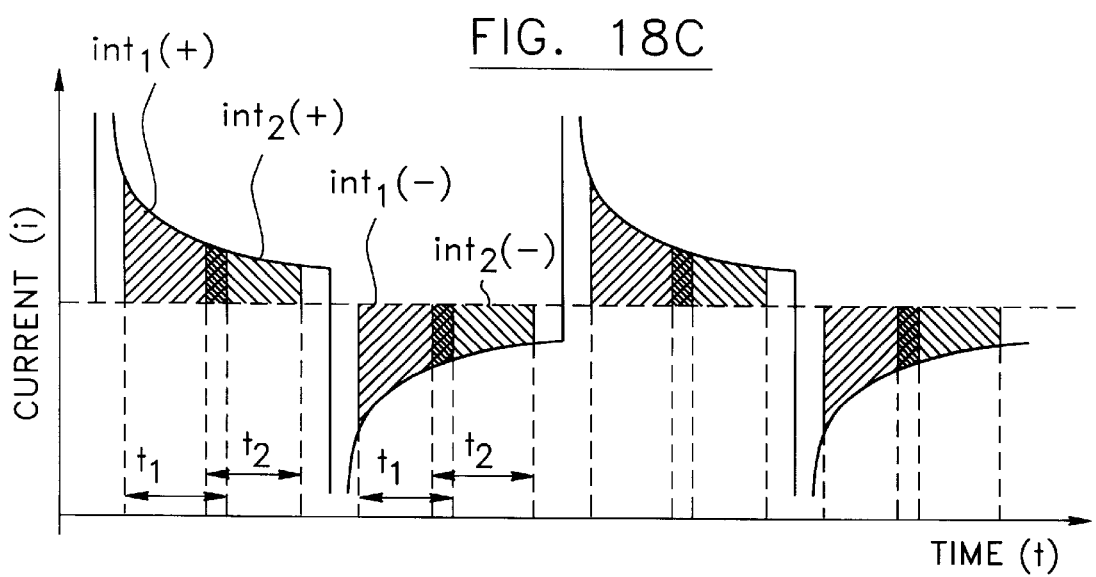

Referring to FIGS. 18A, 18B, the second integration mode, called "double sampling" (DS), consists of integrating the voltage signal $V_{i_M}$ during two predetermined discrete time periods $t_1$, $t_2$ between transitions of the pulses. The DS integration mode is different from the SS mode because during the integrable period of the signal $V_{i_M}$ between pulse transitions, several integrations are carried out instead of a single one. The purpose of the second or last integration is to subtract the residual currents (adsorption or constant components that do not decrease as a function of $1/\sqrt{t}$) and to act so that the sampling is principally the sampling of the faradic current $i_f$. A variant of the DS mode of integration is shown in FIG. 18C, where the integration periods $t_1$, $t_2$ intertwine.

Figure 18D:
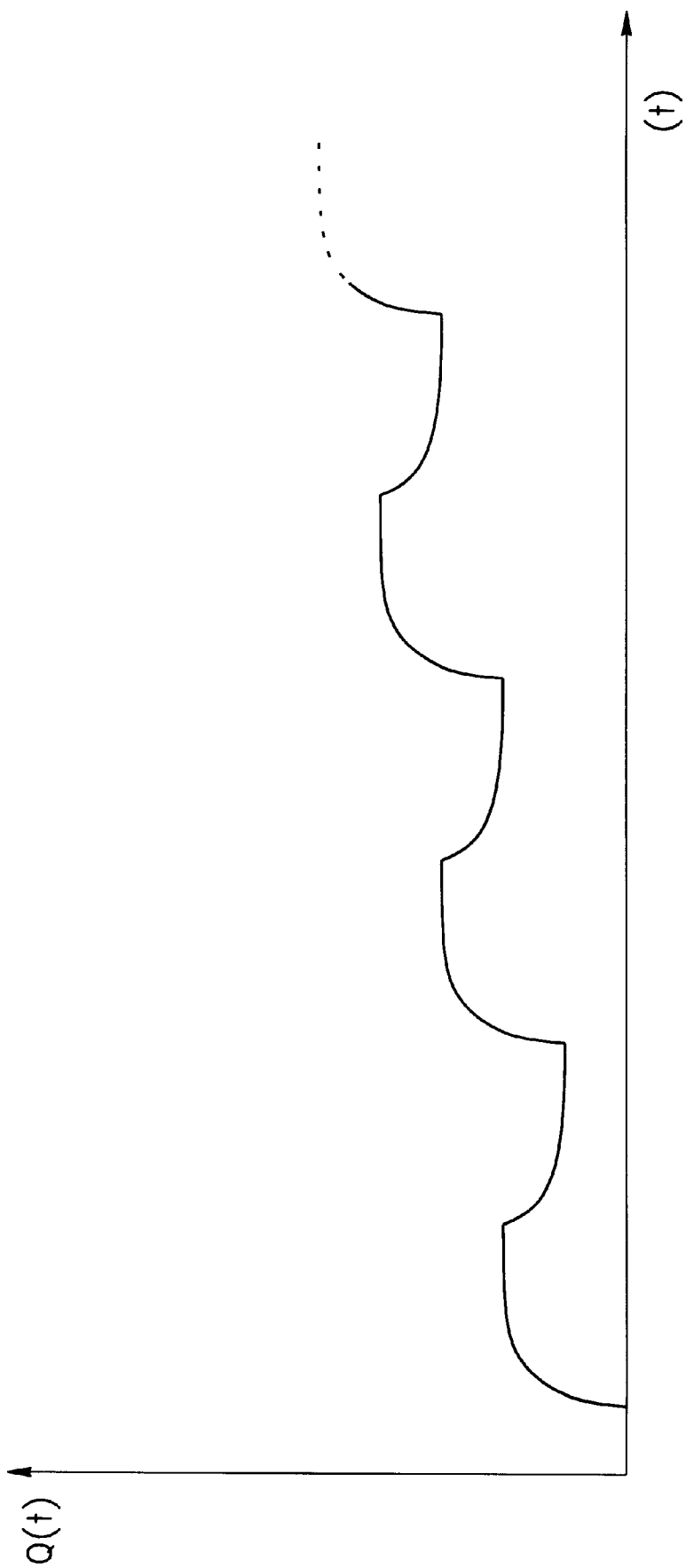

As in the case of the SS integration mode, $t_1$ corresponds to the duration of the period of the control signal int(1) during which the integrations int(+) and int(−) are carried out. $t_2$ corresponds to the duration of the validation signal int(2) during which the integrations int(+) and int(−) are also carried out. In the DS integration mode, the durations $t_1$ and $t_2$ of the validation signals int(1) and int(2) are equal. The DS integration mode permits that the integration periods $t_1$ and $t_2$ be superimposed, as shown in FIG. 18C. In any case (with or without superimposition), the integration periods correspond to the following operations:

$$int_1(+) = \int_{t_1} i_{(E+\Delta E)} dt$$

$$int_2(+) = \int_{t_2} i_{(E+\Delta E)} dt$$

$$int_1(-) = \int_{t_1} i_{(E)} dt$$

$$int_2(-) = \int_{t_2} i_{(E)} dt$$

and the measurement in DS mode is the result of the following operation:

$$\text{Measurement} = \sum_N [int_1(+) - int_2(-) - int_1(-) + int_2(-)]$$

as shown in FIG. 18D. The manipulation of the integrals is simple and efficient in terms of signal/noise ratio.

Figure 19A:
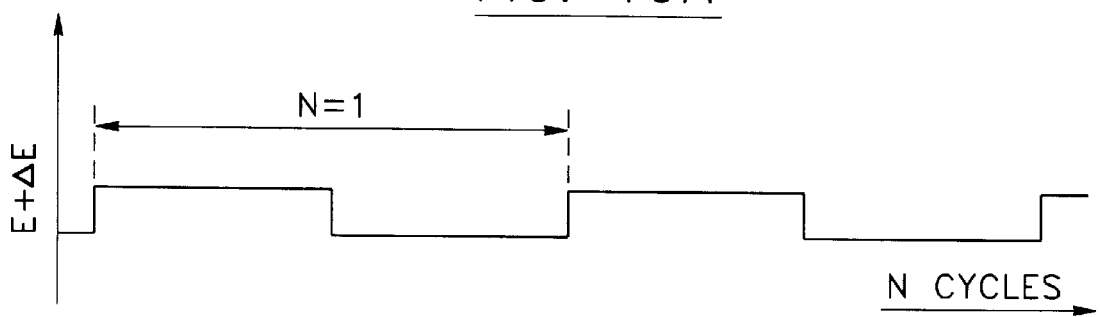
FIGS. 19A to 19C are graphs showing the command signal, the double double sampling modes of integration according to the invention.
Figure 19B:
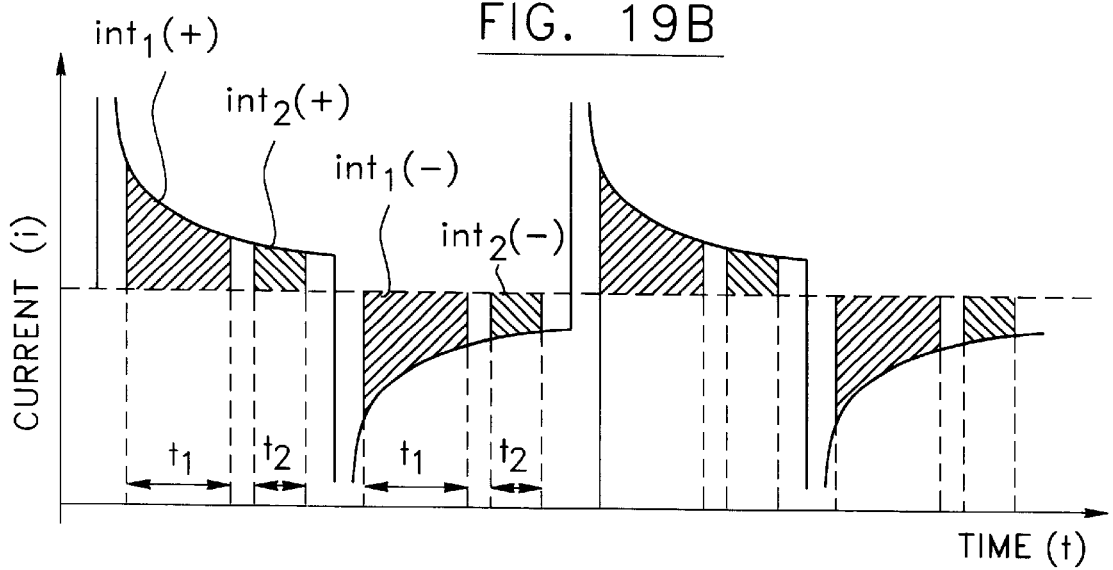
Figure 19C:
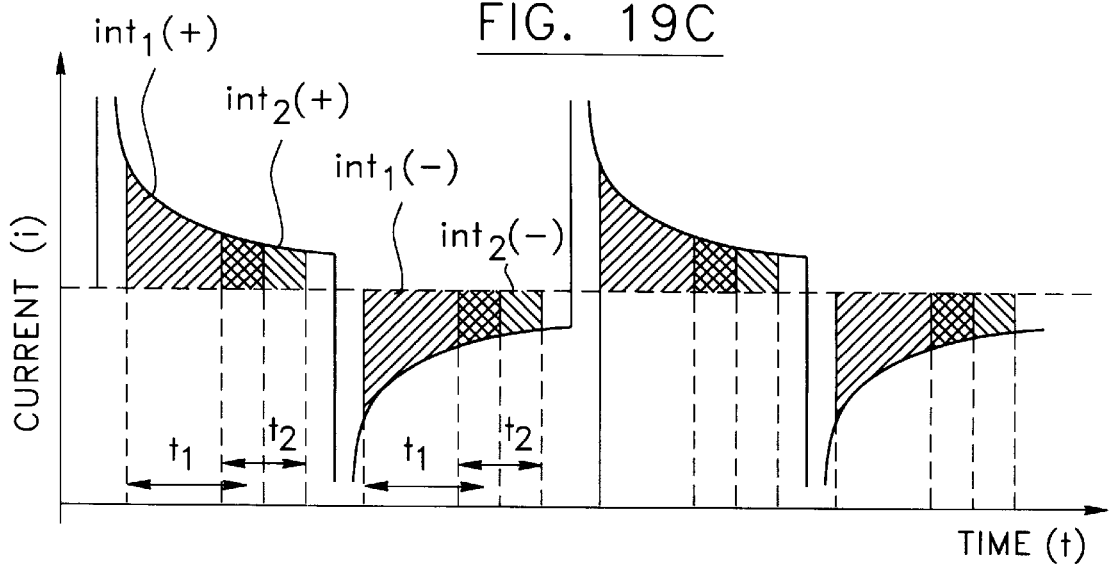

Referring to FIGS. 19A to 19C, there are shown variants of the DS integration mode referred to hereinafter as the DS2 integration mode. The DS2 integration mode is very similar to the DS mode except that durations $t_1$ and $t_2$ are not equal, $t_1$ being longer than $t_2$. To achieve a faster operation, $t_2$ can be for instance the half of $t_1$. The corresponding integrals are then weighted. Thus the measurement in DS2 mode is different as it is the result of the following operation:

$$\text{Measurement} = \sum_N [int_1(+) - int_1(-) - 2[int_2(+) - int_2(-)]]$$

In DS mode, the reset of the integrator's output 130, 146 (as shown in FIGS. 14, 15) must be carried out immediately after the sampling of the integrated response ($V_f$ or $D_f$) by the memorization circuit 28 (as shown in FIG. 1), at the end of the Nth cycle of a potential step, thus between the end of the int(−) control signal and the beginning of the control signal $\overline{SW}$ or next ΔE. The reset operation must be finished as quickly as possible before the beginning of the next integration. The same applies for the DS2 mode, except that the time to consider is the Nth cycle×kth inversion of ΔE, just before the next potential step.

The following description relates to various experimental results selected to show the advantages of the present invention.

Figure 20:
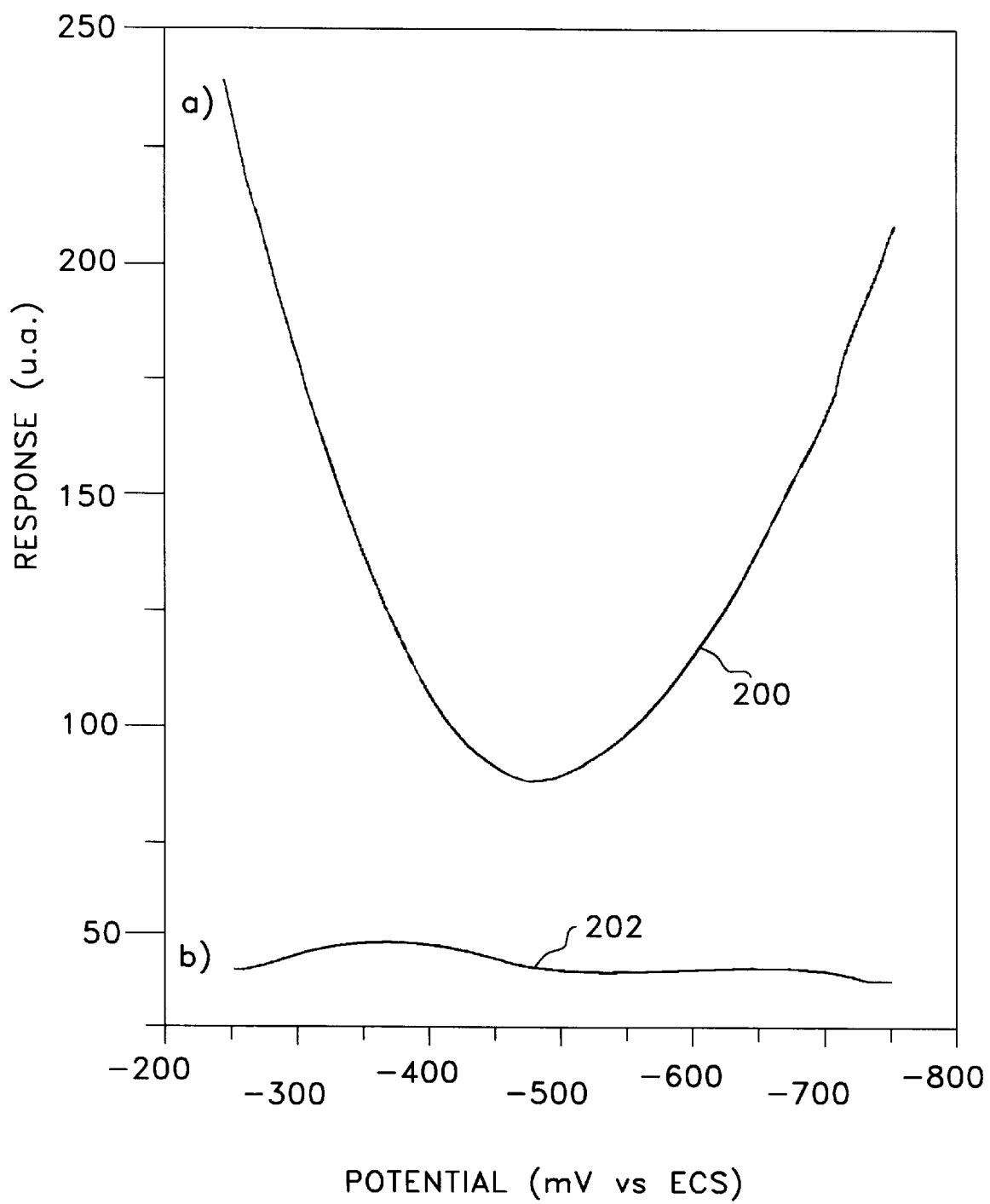
FIG. 20 is a graph showing voltammetric curves of an electrolyte solution obtained in MSWV (a) and MSWV-DD (b) according to the invention.
Figure 21:
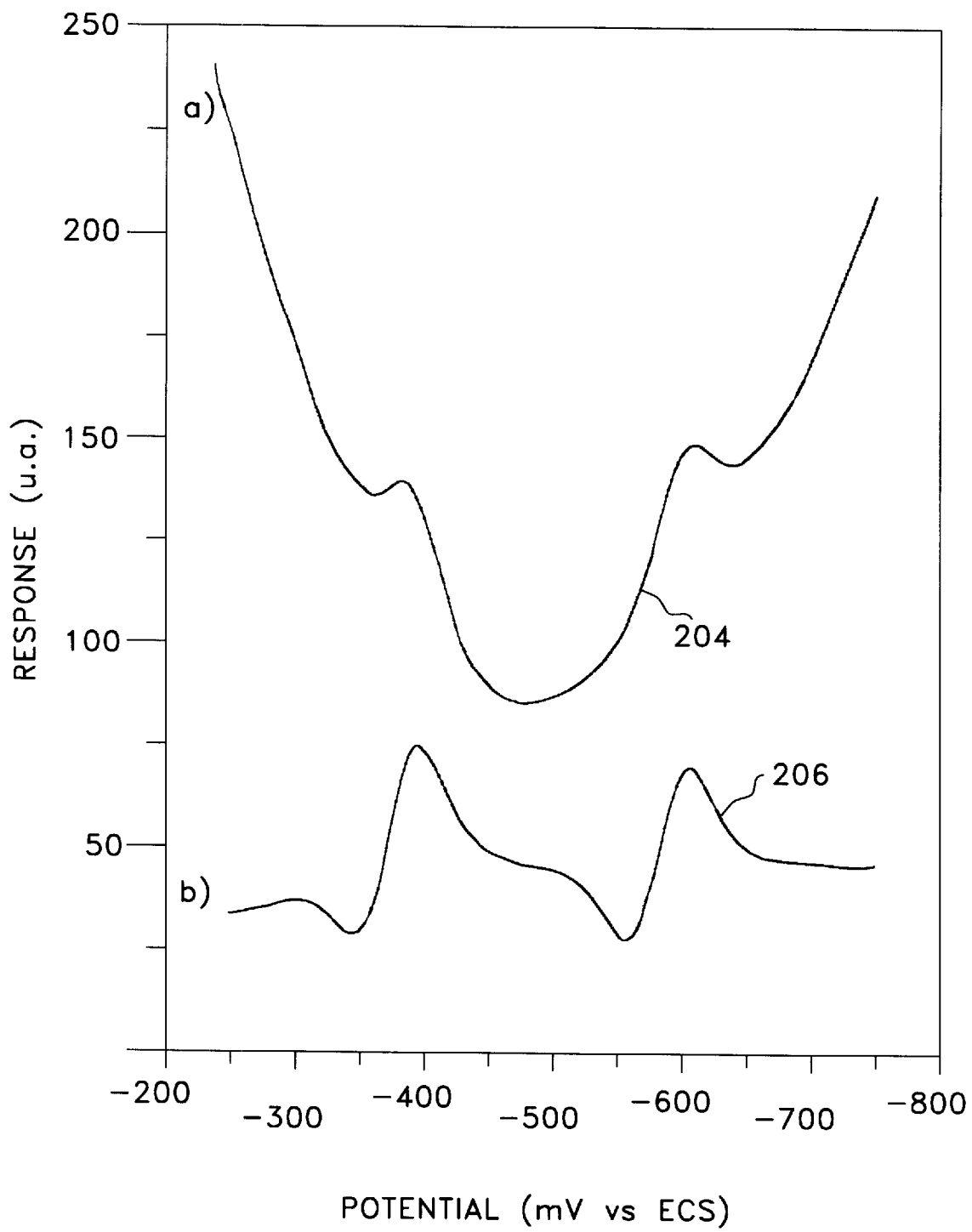
FIG. 21 is a graph showing voltammetric curves of an electrolyte solution containing 5 ppb of lead ($Pb^{2+}$) and cadmium ($Cd^{2+}$) obtained in MSWV (a) and MSWV-DD (b) according to the invention.
Figure 22:
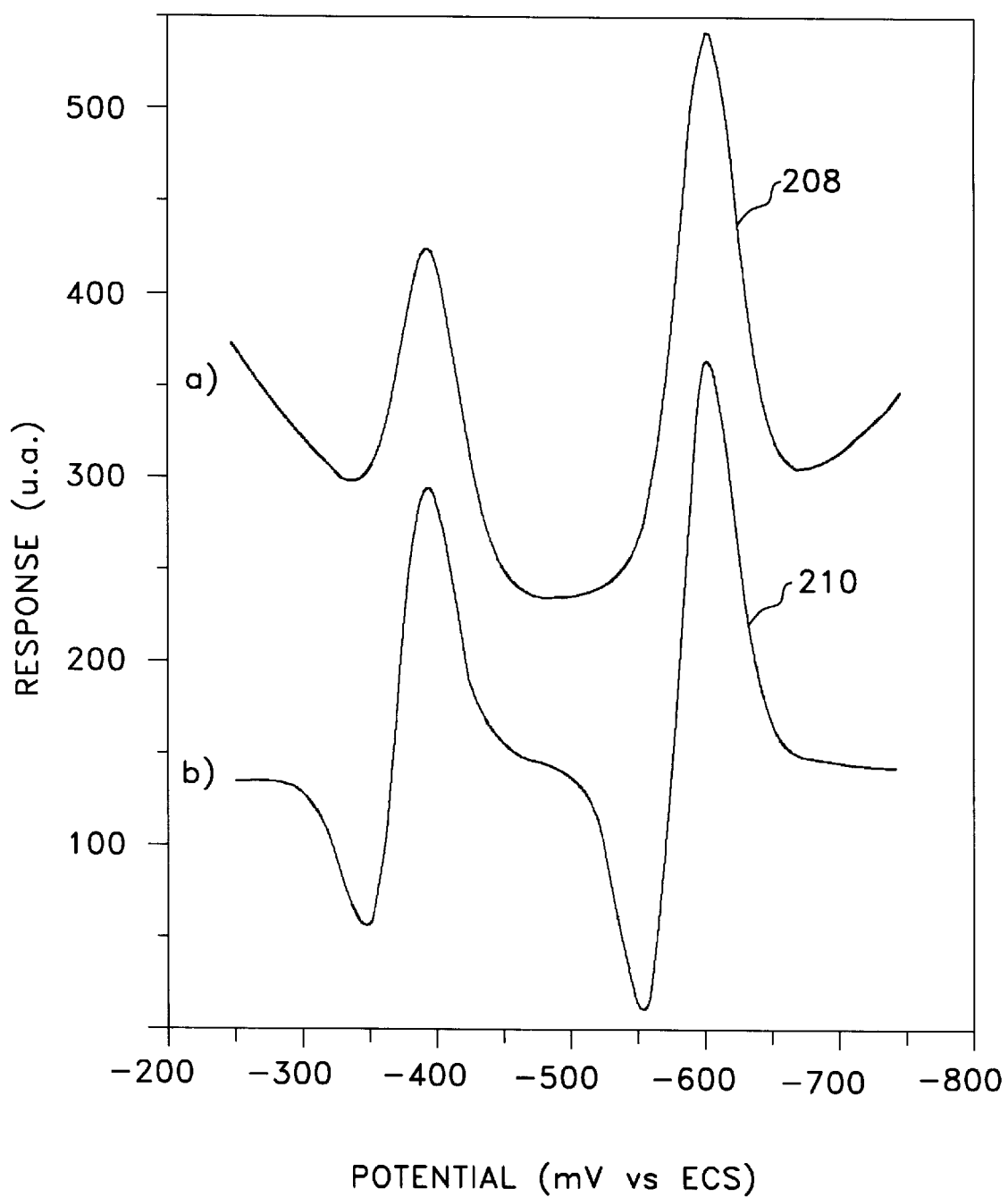
FIG. 22 is a graph showing voltammetric curves of an electrolyte solution containing 5 ppb of lead ($Pb^{2+}$) and cadmium ($Cd^{2+}$) obtained in MSWV (a) and MSWV-DD (b), after a 60 s. accumulation, according to the invention.

Referring to FIGS. 20 to 22, there are graphs showing voltammetric curves for comparisons of the electrochemical methods MSWV and MSWV-DD for doses in:

an electrolytic solution alone;
a solution of 5 ppb of lead ($Pb^{2+}$) and cadmium ($Cd^{2+}$); and FIG. 20 shows two curves, one obtained with the method MSWV as depicted by curve (a) 200, and the other one with MSWV-DD as depicted by curve (b) 202 of an electrolytic solution, in the absence of reducible or oxidizable species. The MSWV curve 200 has a parabolic shape characterized by increases of the response at the limits of the potential scale. The use of the MSWV-DD method permits to counter this increase effect that renders the identification and the quantification of the voltammetric peaks difficult to achieve. The curve 202 shows that the response is clearly improved. It is almost steady over the whole of the potential domain. This dynamic correction is attributable to the shape of the command signal imposed to the electrodes in the MSWV-DD method, i.e. a sequence of N pulses having an amplitude E+$\Delta$E, followed by a sequence of N pulses having an amplitude E−$\Delta$E. FIGS. 21 and 22 show the advantages of the MSWV-DD method applied to solutions containing reducible electroactive species at the electrode. The curves in FIG. 22 have been obtained in ASV (Anodic Stripping Voltammetry), i.e. after an accumulation period at a given potential.

The various experimental conditions associated with FIG. 20 (material, parameters) are as follows:

A) Electrochemical instrument: as hereinabove described
   Method: MSWV (curve 200); MSWV-DD (curve 202)
   Integration mode: SS
   Number of pulses N: 24
   Amplitude E: 30 mV
   Step E: 5 mV
   Impulse and $\tau$: 1/2
   Gain: 1+1/0.1
   Sensitivity/Gain: 4/4
   Initial potential: −750 mV
   Final potential: −250 mV
B) Electrodes
   Working (WE): Hanging drop of mercury, HMDE (EG&G PAR, model 303), medium size
   Auxiliary (CE): Platinum
   Reference (REF): Saturated calomel electrode (SCE)
C) Plotter
   X: 50 mV/cm
   Y: 200 mV/cm
D) Chemical conditions
   Solution: HCl 0.02M (HCl, Ultrapure quality (Seastar) in purified water).

The various experimental conditions associated with FIG. 21 (material, parameters) are as follows:

A) Electrochemical instrument: as hereinabove described
   Method: MSWV (curve 204); MSWV-DD (curve 206)
   Integration mode: SS
   Number of pulses N: 24
   Amplitude E: 30 mV
   Step E: 5 mV
   Impulse and $\tau$: 1/2
   Gain: 1+1/0.1
   Sensitivity/Gain: 4/4
   Initial potential: −750 mV
   Final potential: −250 mV
B) Electrodes
   Working (WE): Hanging drop of mercury, HMDE (EG&G PAR, model 303), medium size
   Auxiliary (CE): Platinum
   Reference (REF): Saturated calomel electrode (SCE)
C) Plotter
   X: 50 mV/cm
   Y: 200 mV/cm
D) Chemical conditions
   Solution: 5 ppb of $Pb^{2+}$ and $Cd^{2+}$ in HCl 0.02M (HCl, Ultrapure quality (Seastar) in purified water).

The various experimental conditions associated with FIG. 22 (material, parameters) are as follows:

A) Electrochemical instrument: as hereinabove described
   Method: MSWV (curve 208); MSWV-DD (curve 210)
   Integration mode: SS
   Number of pulses N: 24
   Amplitude E: 30 mV
   Step E: 5 mV
   Impulse and $\tau$: 1/2
   Gain: 1+1/0.1
   Sensitivity/Gain: 4/4
   Initial potential: −750 mV
   Final potential: −250 mV
   Accumulation time: 60 s
B) Electrodes
   Working (WE): Hanging drop of mercury, HMDE (EG&G PAR, model 303), medium size
   Auxiliary (CE): Platinum
   Reference (REF): Saturated calomel electrode (SCE)
C) Plotter
   X: 50 mV/cm
   Y: 200 mV/cm
D) Chemical conditions
   Solution: 5 ppb of $Pb^{2+}$ and $Cd^{2+}$ in HCl 0.02M (HCl, Ultrapure quality (Seastar) in purified water).

Figure 23:
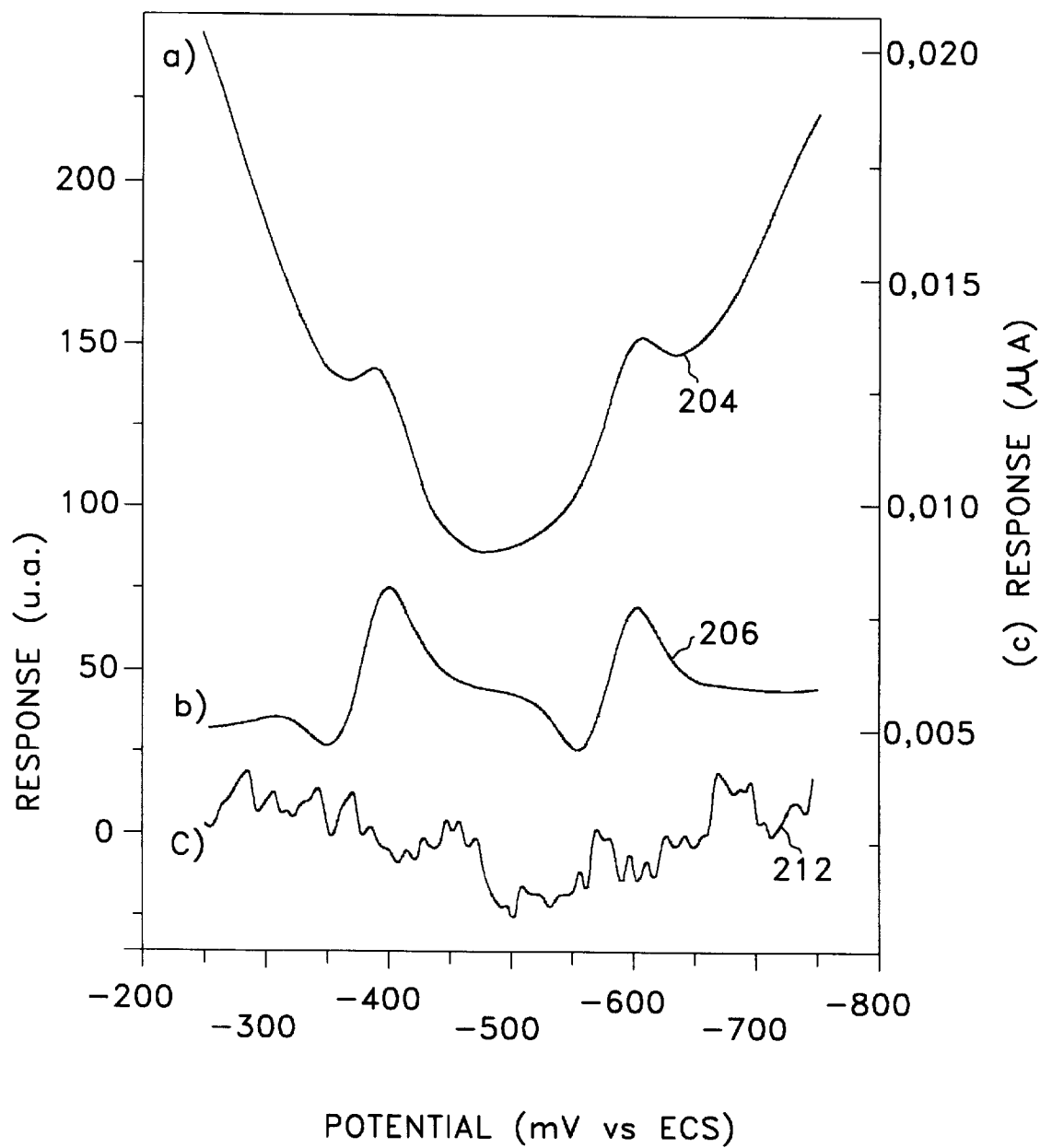
FIG. 23 is a graph showing voltammetric curves of an electrolyte solution containing 5 ppb of lead ($Pb^{2+}$) and cadmium ($Cd^{2+}$) obtained in MSWV (a), MSWV-DD (b), and DPV (c) according to the invention.
Figure 24:
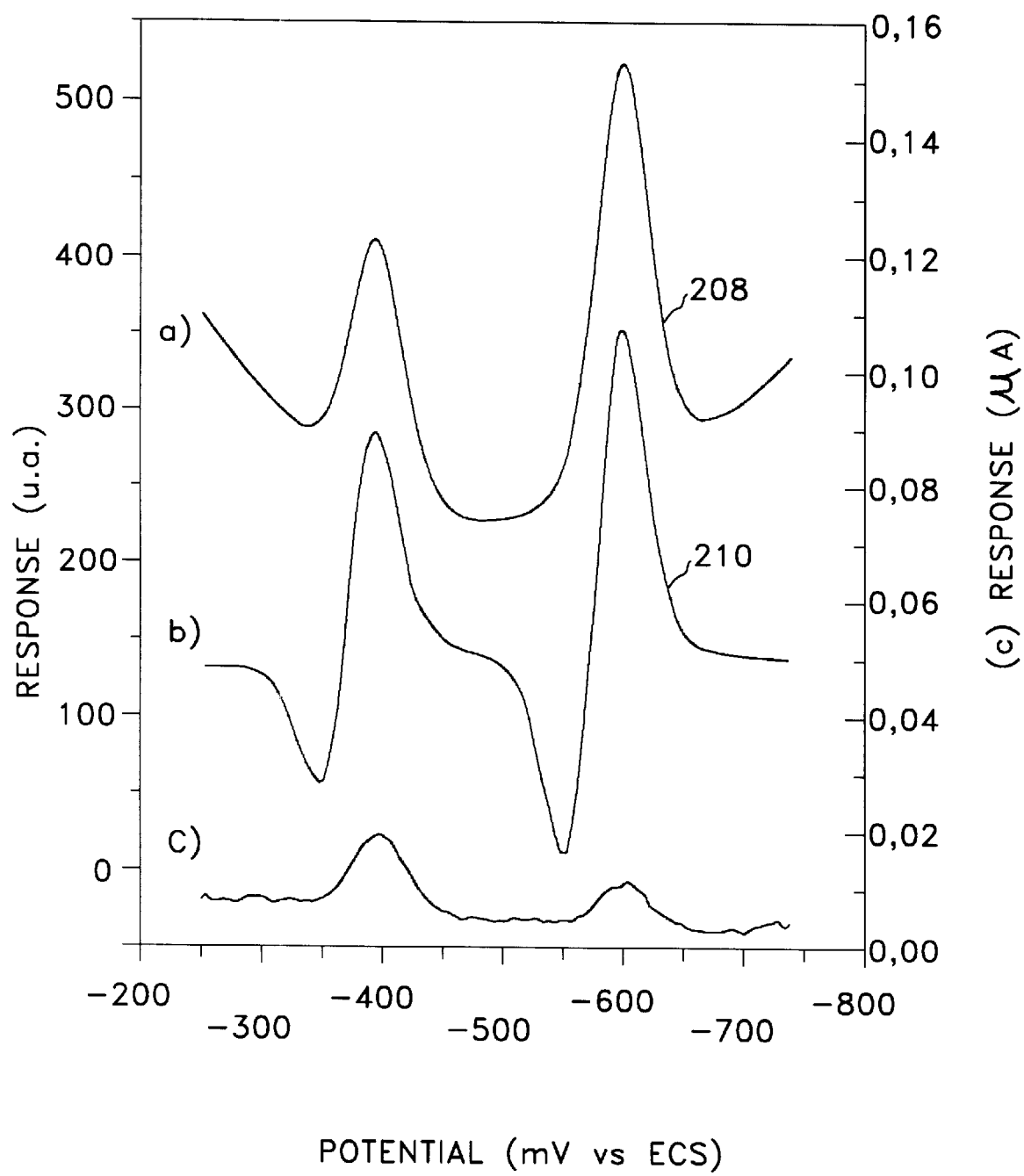
FIG. 24 is a graph showing voltammetric curves of an electrolyte solution containing 5 ppb of lead ($Pb^{2+}$) and cadmium ($Cd^{2+}$) obtained in MSWV (a), MSWV-DD (b), and DPV (c), after a 60 s. accumulation, according to the invention.

Referring to FIGS. 23 and 24, there are graphs showing voltammetric curves for comparisons of the electrochemical methods MSWV and MSWV-DD and DPV for doses in:
   a solution of 5 ppb of lead ($Pb^{2+}$) and cadmium ($Cd^{2+}$); and
   a solution of 5 ppb of lead ($Pb^{2+}$) and cadmium ($Cd^{2+}$) in ASV.

The Differential Pulse Voltammetry (DPV) is a well known method that has been commonly used in electrochemistry. FIGS. 22 and 23 show the advantages of MSWV pulse methods applied to solutions containing electroactive reducible species at the electrode. The curves 208, 210, 214 in FIG. 24 have been obtained in ASV.

The various experimental conditions associated to FIG. 23 (material, parameters) are the same as for FIG. 21, except for:

A) Instrument: Cypress (trademark), model CS-2Ra
   Method: DPV (curve 212 )
   Pulse height: 30 mV
   Step height: 5 mV
   Cycle period: 100 ms
   Pulse width: 40 ms
   Sample time: 35 ms
   Current range: 2 $\mu$A
   Noise filter: 2000 $\mu$s
   Initial potential: −750 mV
   Final potential: −250 mV The various experimental conditions associated to FIG. 24 are the same as for FIGS. 22 and 23. The accumulation period is 60 s.

Figure 25:
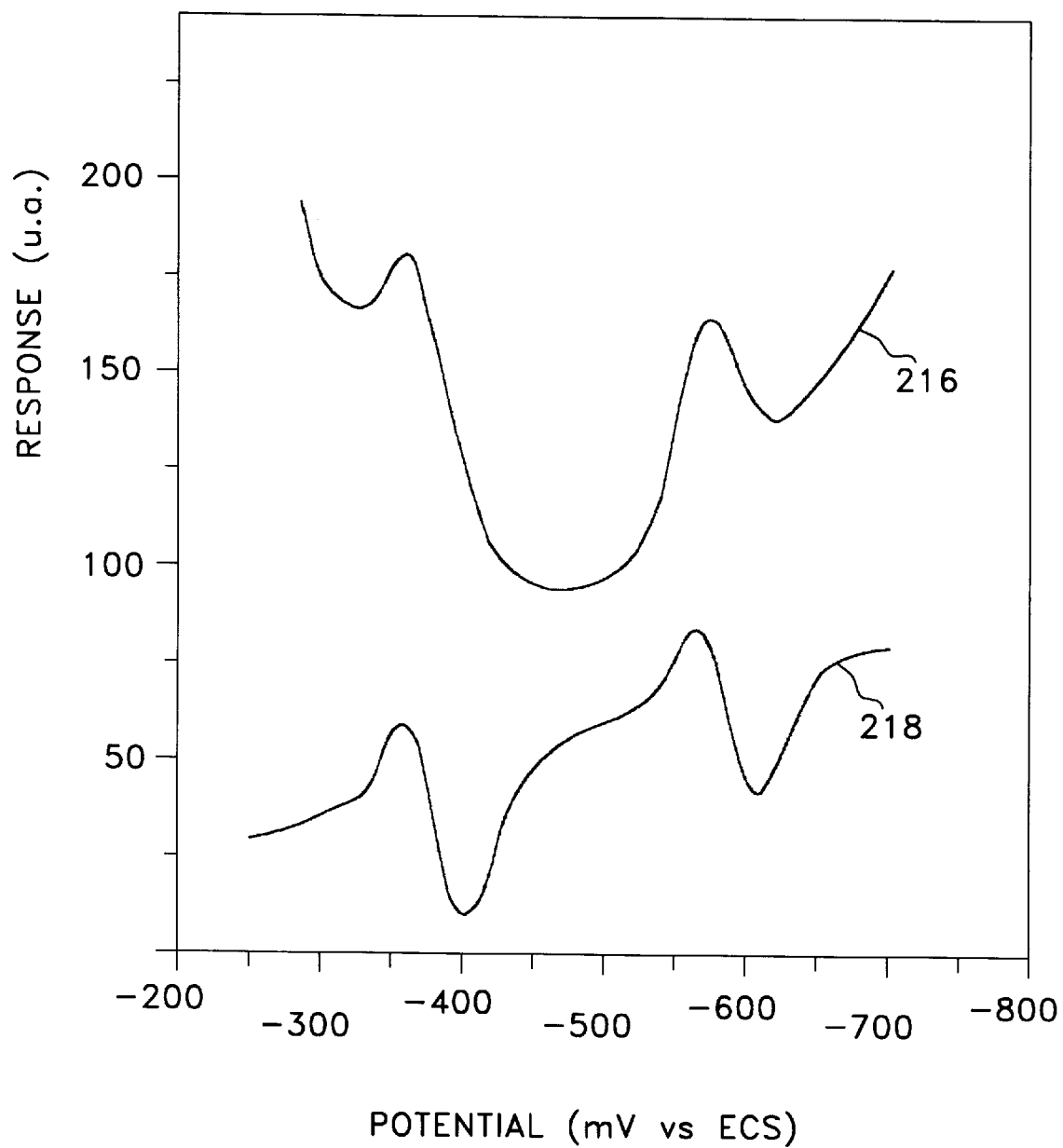
FIG. 25 is a graph showing voltammetric curves of an electrolyte solution containing 16 ppt of lead ($Pb^{2+}$) and cadmium ($Cd^{2+}$) obtained in MSWV (upper curve) and MSWV-DD (lower curve), after a 360 s. accumulation, according to the invention.
Figure 26:
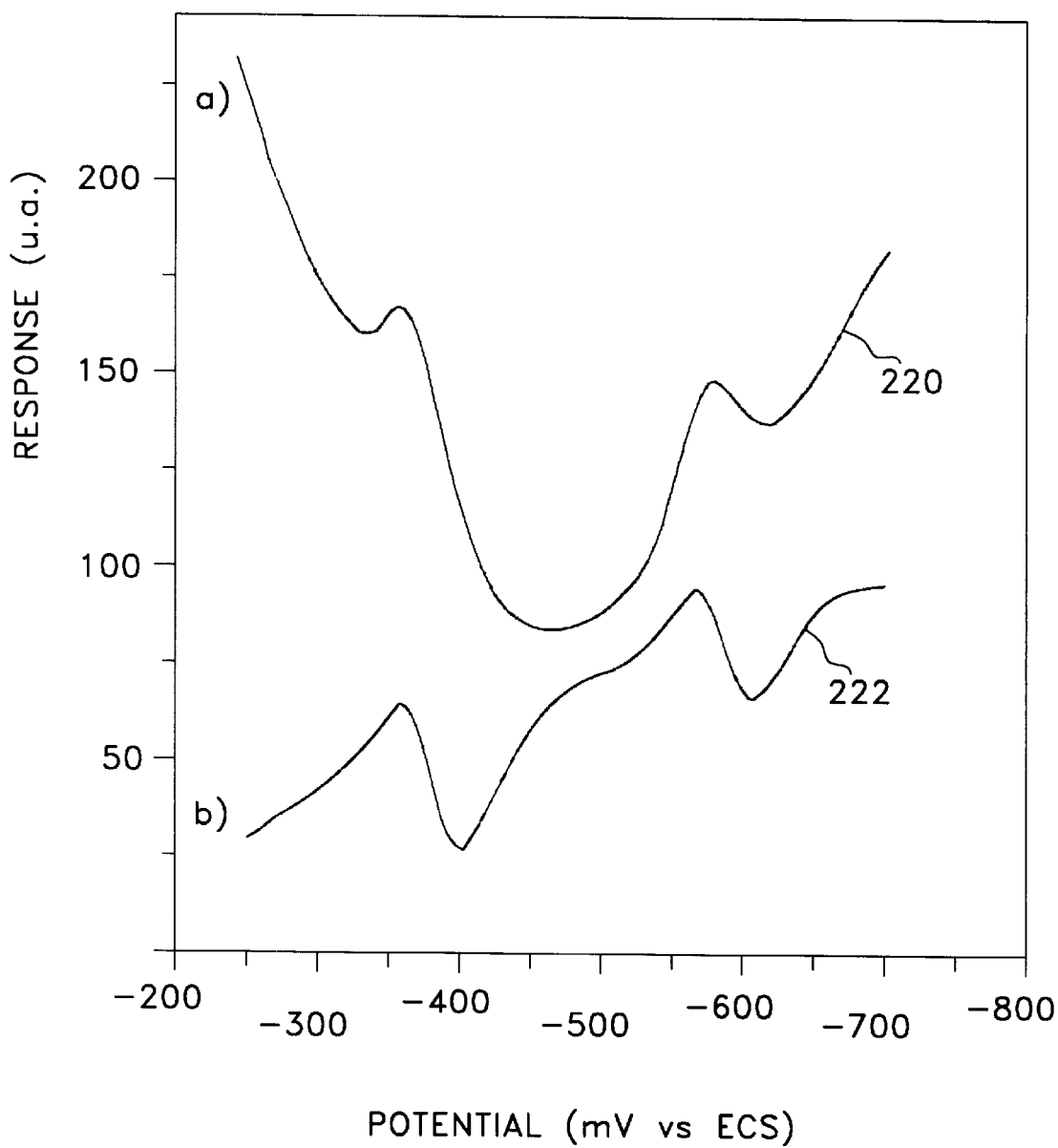
FIG. 26 is a graph showing voltammetric curves of an electrolyte solution containing 8 ppt of lead ($Pb^{2+}$) and cadmium ($Cd^{2+}$) obtained in MSWV (upper curve) and MSWV-DD (lower curve), after a 360 s. accumulation, according to the invention.

Referring to FIGS. 25 and 26, there are shown curves for doses at 16 and 8 ppt of Pb and Cd concentrations, obtained in MSWV (curve 216) and MSWV-DD (curve 218).

The various experimental conditions associated with FIGS. 25 and 26 (material, parameters) are as follows:
A) Electrochemical instrument: as hereinabove described
  Method: MSWV (curve 216); MSWV-DD (curve 218)
  Integration mode: SS
  Number of pulses N: 24
  Amplitude E: 30 mV
  Step E: 5 mV
  Impulse and τ: 1/2
  Gain: 1+1/1
  Sensitivity/Gain: 4/4
  Initial potential: −750 mV
  Final potential: −250 mV
  Accumulation potential: −750 mV
  Accumulation time: 360 s
B) Electrodes
  Working (WE): Hanging drop of mercury, HMDE (EG&G PAR, model 303), medium size
  Auxiliary (CE): Platinum
  Reference (REF): Saturated calomel electrode (SCE)
C) Plotter
  X: 50 mV/cm
  Y: 200 mV/cm
D) Chemical conditions
  Solution of FIG. 25: 16 ppt of $Pb^{2+}$ and $Cd^{2+}$ in HCl 0.05M (HCl, Ultrapure quality (Seastar) in purified water).
  Solution of FIG. 26: 8 ppt of $Pb^{2+}$ and $Cd^{2+}$ in HCl 0.05M (HCl, Ultrapure quality (Seastar) in purified water).

Figure 27:
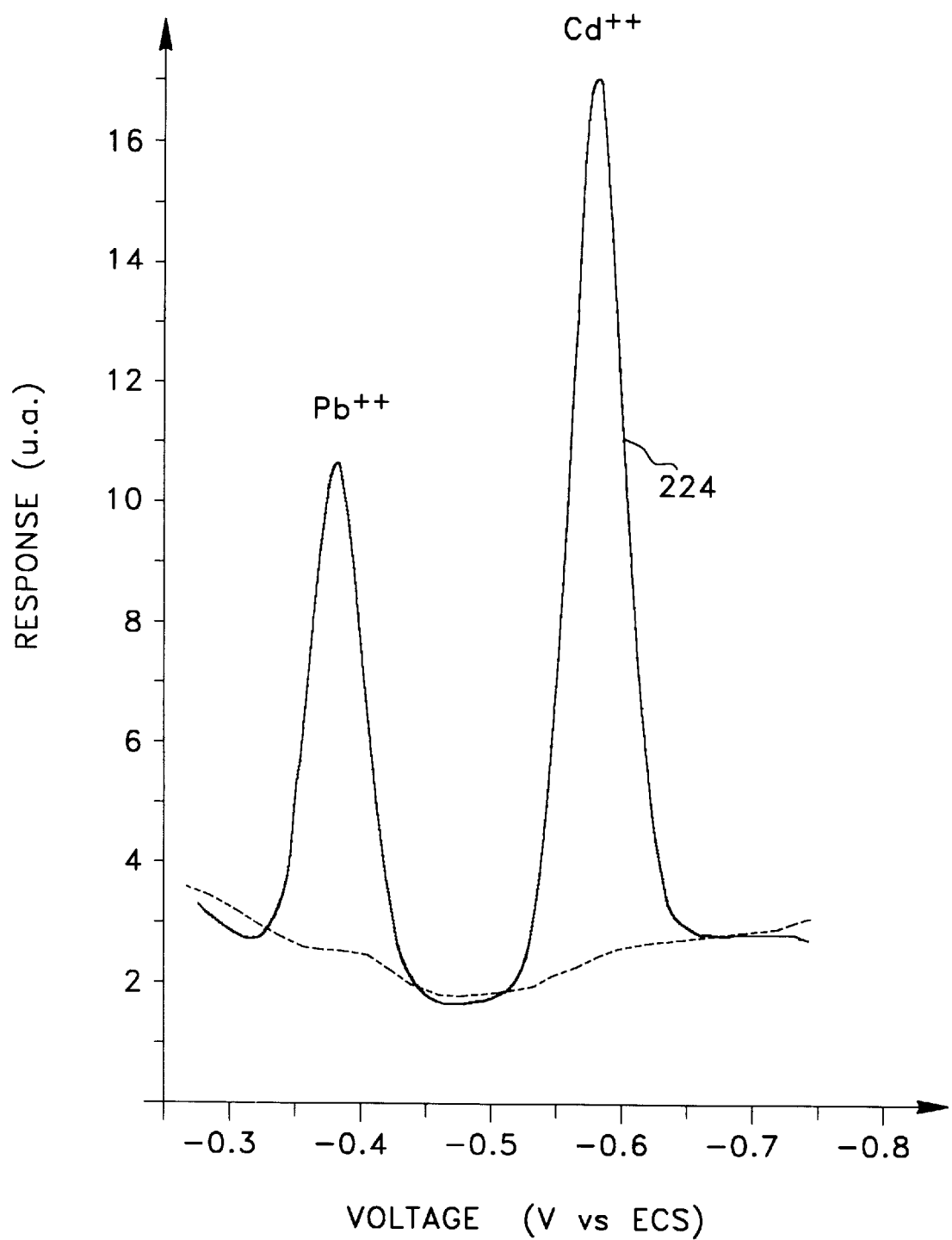
FIG. 27 is a graph showing a voltammetric curve of an electrolyte solution containing 5 ppb of lead ($Pb^{2+}$) and cadmium ($Cd^{2+}$) obtained in MSWV, after a 180 s. accumulation, according to the invention.
Figure 28:
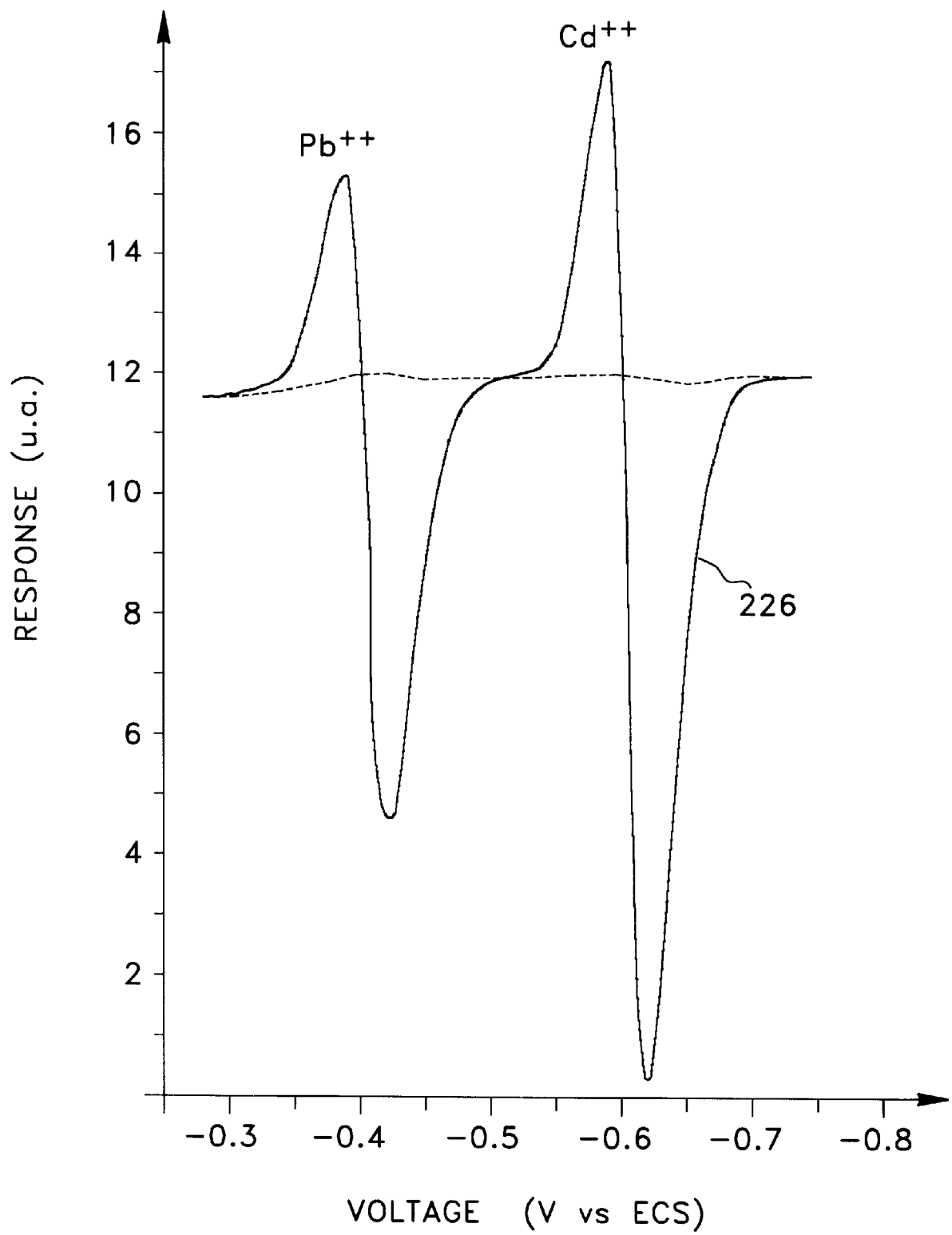
FIG. 28 is a graph showing a voltammetric curve of an electrolyte solution containing 5 ppb of lead ($Pb^{2+}$) and cadmium ($Cd^{2+}$) obtained in MSWV-DD, after a 180 s. accumulation, according to the invention.
Figure 29:
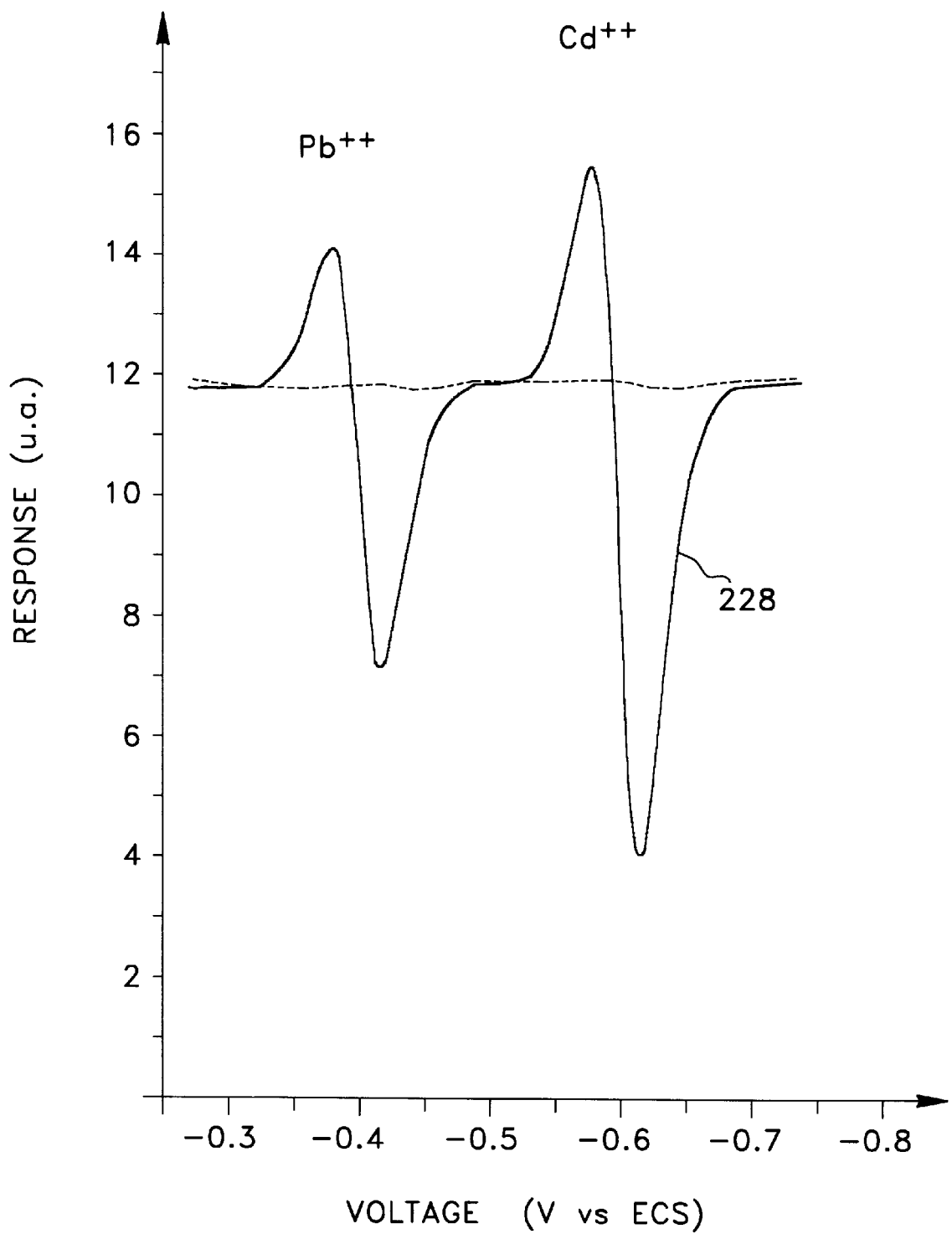
FIG. 29 is a graph showing a voltammetric curve of an electrolyte solution containing 5 ppb of lead ($Pb^{2+}$) and cadmium ($Cd^{2+}$) obtained in MSWV-DD in double sampling mode of integration, after a 180 s. accumulation, according to the invention.
Figure 30:
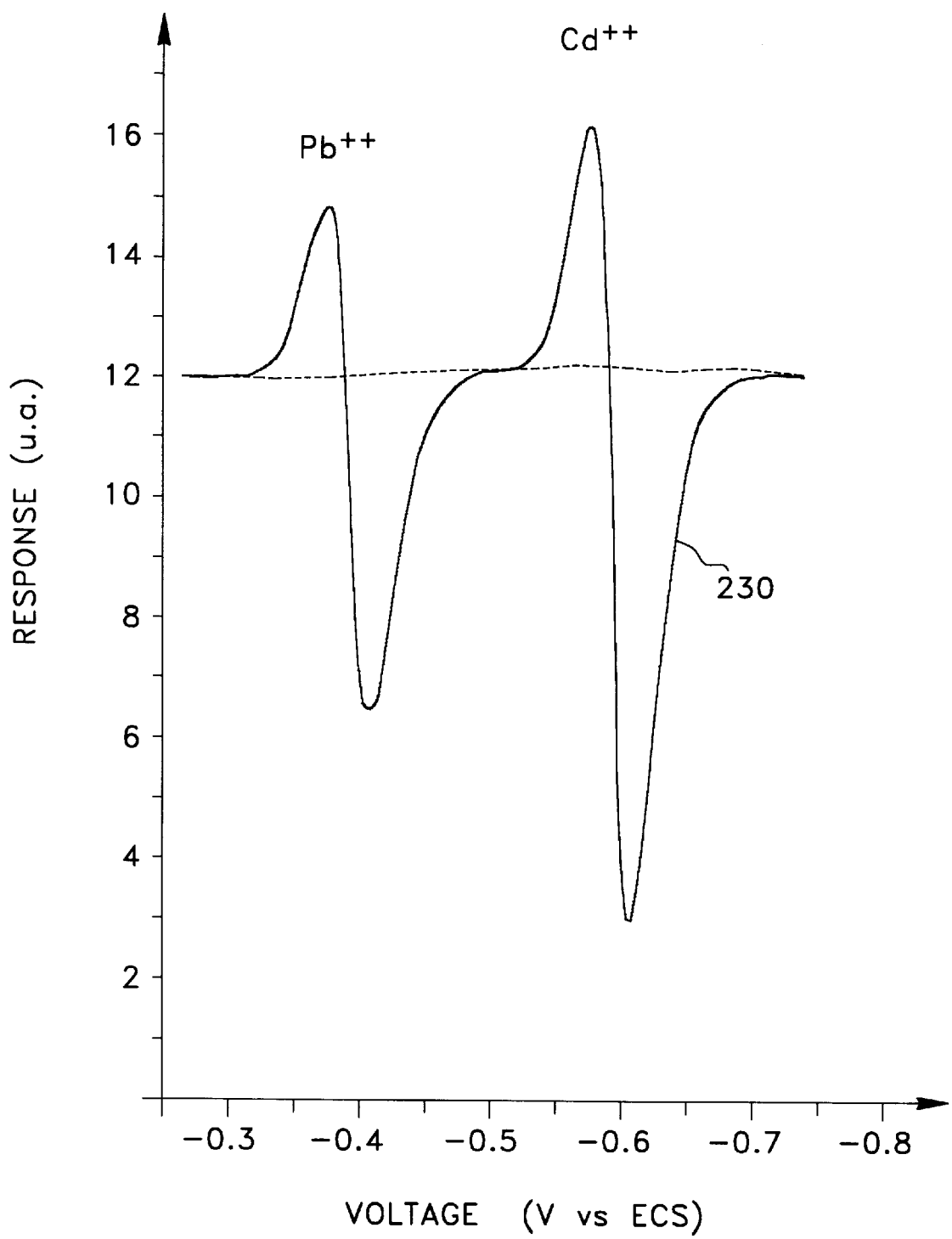
FIG. 30 is a graph showing a voltammetric curve of an electrolyte solution containing 5 ppb of lead ($Pb^{2+}$) and cadmium ($Cd^{2+}$) obtained in MSWV-DD in double double sampling mode, after a 180 s. accumulation, according to the invention.

Referring to FIGS. 27 to 30, there are shown graphs of voltammetric curves for comparisons between the integration modes SS, DS and DS2 used in conjunction with the dosing method MSWV-DD for a solution containing 5 ppb of Pb and Cd. FIG. 27 shows the same dose but with the method MSWV.

The various experimental conditions associated with FIGS. 27 to 30 (material, parameters) are as follows:
A) Electrochemical instrument: as hereinabove described
  Method: MSWV (curve 224 in FIG. 27); MSWV-DD (curves 226, 228, 230 in FIGS. 28 to 30)
  Integration mode: SS (FIGS. 27, 28)
    DS (FIG. 29)
    DS2 (FIG. 30)
  Number of pulses N: 24
  Amplitude E: 30 mV
  Step E: 5 mV
  Impulse and τ: 1/2
  Gain: 3+1/1
  Sensitivity/Gain: 4/4
  Initial potential: −750 mV
  Final potential: −250 mV
  Accumulation potential: −750 mV
  Accumulation time: 180 s
B) Electrodes
  Working (WE): Hanging drop of mercury, HMDE (EG&G PAR, model 303), medium size
  Auxiliary (CE): Platinum
  Reference (REF): Saturated calomel electrode (SCE)
C) Plotter
  X: 50 mV/cm
  Y: 200 mV/cm
D) Chemical conditions
  Solution of FIG. 25: 5 ppb of $Pb^{2+}$ and $Cd^{2+}$ in HCl 0.05M (HCl, Ultrapure quality (Seastar) in purified water).

In view of the above mentioned features of the instrument, many voltammetric modes (as hereinabove described or others known in the art) and combination thereof can be put into practice using the instrument.

Furthermore, the instrument according to the invention can be also used for other applications outside the electrochemical domain (polarographic or voltammetric methods).

Figure 31:
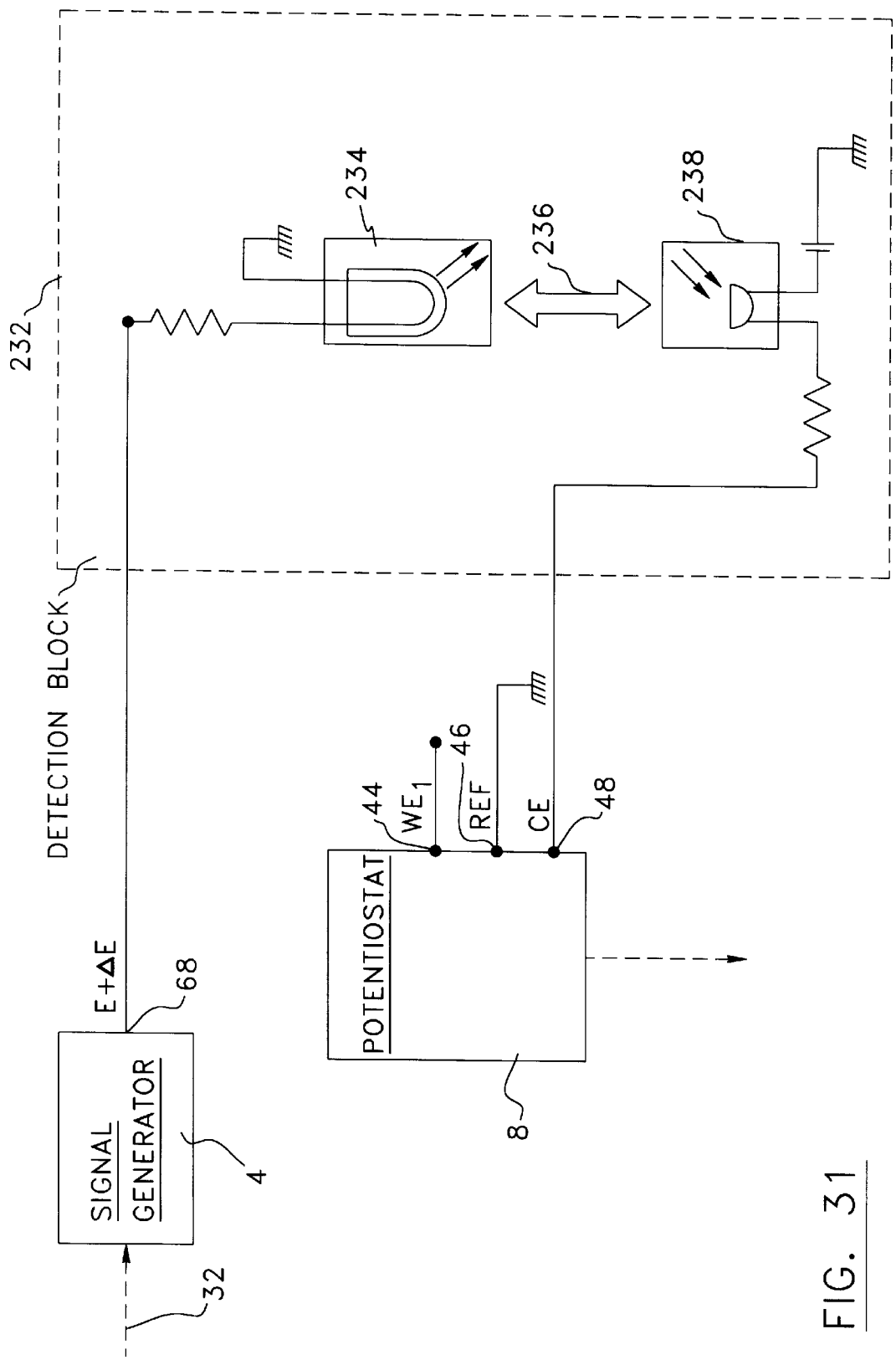
FIG. 31 is a partial block diagram showing the connections between an instrument according to the present invention and a light emitter/photodetector measurement device.

Referring to FIG. 31, there is shown an example of such other application, in which the electrochemical cell 20 as shown in FIG. 1 is replaced by a detection block 232 suitable to the nature of the phenomenon to be observed. In this case, the signal E+ΔE, produced by the signal generator 4, is directly used to modulate the emission of a light emitter 234 (e.g. infrared, ultraviolet, visible or laser) across an optical path 236 up to a photodetector 238 that is connected to the potentiostat 8 and more particularly to the instrument terminal 48, in replacement to a counter electrode (CE). This circuit is intended to permit the measurement of the variation of the light signal induced by the absorption of the matter (gas or liquid) located in the optical path 236 between the emitter 234 and the photodetector 238. In view of the type of phenomenon involved in this application, there is no need of an impulse as provided by the impulse generator 6 shown in FIG. 1. The instrument terminal 46 is grounded, and the instrument terminal 44 remains floating. The output 113 of the current to voltage converter 22 is no longer useful.

A generalization of the principles and the modes of combining the responses to improve the S/N ratio can be done. The applications concerned by this generalization do not always require the use of all the components of the instrument shown in FIG. 1. Sometimes, these applications even require to use additional components chosen specifically as a function of the phenomenon to be studied. The applications derived from the generalization can be classified into two types depending on whether they rely upon the various basic principles applied in relation with the instrument and the methods hereinabove described, or a combination thereof. The first type of generalized applications uses the response signals, resulting from the multiple perturbations, in a summation of integrals according to the MSWV methodology. The second type of generalized applications uses the response signals, produced by distinct perturbations according to the above-described method with the DD (double differential) mode.

The first type applications' goal is to improve the S/N ratio by the combined effects of the repetition and the integration of the individual responses. The functioning of the first type applications requires a perturbing parameter associated to the phenomenon to be measured, a sequence comprising multiple perturbations combined or not to one or more other parameters affecting the measurement, a detection system suited to the phenomenon, comprising for example an electronic detector and circuit, and a group of circuits for the measurement and then the integration of the response signals in synchronicity with the sequence of perturbations.

The method of improving the S/N ratio in a measurement of a physical phenomenon responsive to a predetermined type of perturbation, in accordance with the first type of applications, comprises the steps of producing a sequence of multiple perturbations of the aforementioned type to affect the physical phenomenon, measuring the physical phenomenon affected by the perturbations, to produce response signals relative to the perturbations respectively, time-integrating the response signals to produce integrated response signals, and performing, in time, addition or subtraction operations on the integrated response signals. The repetition of the perturbations and the integration of the response signals improve the S/N ratio.

The above example of FIG. 31 falls into the first type of applications.

The second type of generalized applications leads, in addition to the advantages of the first type applications, to derivative types of responses with respect to the first type applications, which permits to suppress offset and drift problems of the measurements. The functioning of the second type applications requires that the perturbations be defined either by perturbations of a same nature but of opposite polarity or intensity having distinct effects on the response signal, or by comparable perturbations but applied with a shift in one or more variables influencing the phenomenon, like time, potential, frequency, flow, wavelength, etc., or by a combination of perturbations of different natures and/or separately having effects on the response signal.

In the latter case, this definition of the type of perturbations usable in the second type applications, permits to generalize the use since it contains the notion of recursiveness which means "that has the property to define a new mode by resorting to its own definition". Indeed, if different types of perturbations are applicable, the extensions to superior levels are applicable as well. This is the mathematical equivalent to successive derivations. This can be illustrated in the following manner by taking an electrochemical example.

A MSWV-DD mode is formed using series of perturbations of opposite signs as hereinabove mentioned. If two of these modes are associated in a same execution but with a shift in potential between the first and the second MSWV-DD modes, the resulting combination produces a derivative response of a superior order with respect to the response of an individual mode.

The importance of the recursiveness notion can be understood considering that the double MSWV-DD mode can be applied to a system of two identical electrodes that are shifted in potential since the resulting combination leads to a response once again derived, i.e. which has the characteristics of a response derived at an order still superior to the first.

This composition of signals has an important practical interest since it permits to produce a plus signal having a lower noise than the noise that accompanies the individual signals. This is caused by what can be called the "subtraction" of the noise components that are correlated in the low-pass band of the observation. The off-band components stay because they are too fast but they will be later attenuated by an integration of the response whose purpose is also to reestablish a conventional morphology (peak form) as it is the case practised in MSWV.

The method of improving the S/N ratio while reducing offset and drift in a measurement of a physical phenomenon responsive to predetermined types of perturbations, in the second type of applications, comprises the steps of producing a first perturbation of one of the aforementioned types to produce an effect upon the physical phenomenon, producing either a second perturbation of a same type but opposite to the first perturbation to produce a distinct effect upon the physical phenomenon relative to the effect produced by the first perturbation, or a second perturbation comparable to the first perturbation but of a different one of said types with a shift in a variable affecting the phenomenon, measuring the physical phenomenon affected by the perturbations, to produce response signals relative to the perturbations respectively, time-integrating the response signals to produce integrated response signals, and performing, in time, addition or subtraction operations on the integrated response signals. The integrated response signals provide a derivative type of response as a result of the first and second perturbations, thereby reducing offset and drift while improving the S/N ratio. The second perturbation can be of the same type and have an opposite polarity or intensity relative to the first perturbation. The second perturbation can also be of the different one of the aforesaid types, the variable being time, potential, frequency, flow, wavelength or a similar physical parameter. The second perturbation can be with shifts in additional variables affecting the physical phenomenon. The method may comprise the additional step of repeating the steps of producing the first and second perturbations a predetermined number of times. In such a case, the method may comprise the additional step of combining, with the first and second perturbations, additional perturbations obtained as per the step of producing the second perturbation.

Figure 32:
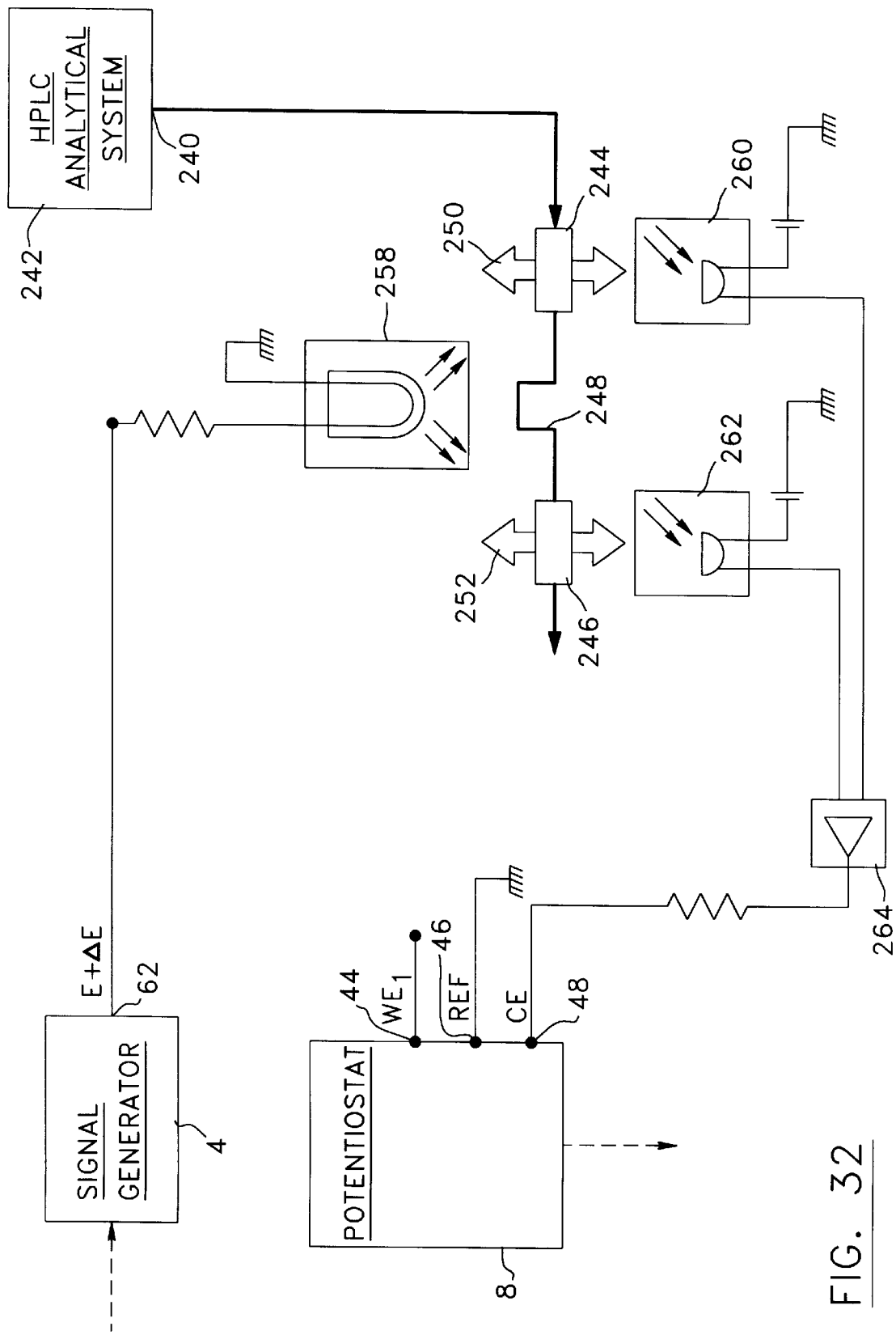
FIG. 32 is a partial block diagram showing the connections between an instrument according to the present invention and an optical detection measurement device.

Referring to FIG. 32, there is shown an example of an application of the second type, using the DD mode in a domain outside the electrochemical one. The application consists in an optical detection (ultraviolet, visible or infrared) at the output 240 of a high pressure liquid chromatography (HPLC) analytical system 242 from which a fluid or a liquid containing a certain quantity of a light absorbing substance is passed in two detection cells 244, 246 that are separated by a delay loop 248. The transportation of the substance to be detected is achieved by the fluid or liquid. The illustrated setup causes the substance in question to pass across the optical path 250, 252 in one cell 244 and then the other cell 246 at different moments.

The detection of the phenomenon is time-shifted by means of a lengthened path formed by the delay loop 248 located between the two detection cells 244, 246. The signal $E+\Delta E$ derived from the signal generator 4 controls an electronic device permitting to modulate a light emitter 258 directed toward the optical paths 250, 252 of the cells 244, 246. The subtraction of the signals generated by two photocells 260, 262 in response to light received from the cells 244, 246 is achieved by an amplifier circuit 264 that returns the resulting signal to the input (CE) 48 of the potentiostat 8 of an instrument like the one hereinabove described, for further processing.

While embodiments of this invention have been illustrated in the accompanying drawings and described above, it will be evident to those skilled in the art that changes and modifications may be made therein without departing from the essence of this invention. All such modifications or variations are believed to be within the sphere and scope of the invention as defined by the claims appended hereto.

What is claimed is:

1. A multiple waveform voltammetric instrument comprising:
   a signal generator means for generating a command signal including pulses superimposed on a DC bias potential, the generator means including means for selectively inverting the pulses, and means for selecting a DC level of the DC bias potential;
   a potentiostat having an input for receiving the command signal, first, second and third instrument terminals, and regulating means for applying, between the first and second instrument terminals, a potential difference corresponding substantially to the command signal;

means for grounding the third instrument terminal and producing an output signal indicative of a current flowing through the third instrument terminal;

an integrator means for integrating the output signal to produce an integrated response signal, the integrator means including means for selectively inverting the output signal prior to integration, and means for resetting the integrated response signal; and control means for time-controlling generation and inversion of the pulses, the DC level of the DC bias potential, inversion and integration of the output signal and resetting of the integrated response signal, according to a selected voltammetric mode of operation.

2. An instrument according to claim 1, wherein the control means are provided with a mode of control causing the means for selecting to cyclically increase the DC bias potential by a potential step to form a potential staircase signal sweeping across a predetermined potential domain.

3. An instrument according to claim 2, wherein the control means are provided with a mode of control causing the means for selectively inverting the pulses to operate so that the command signal includes at least one sequence of two successive pulse trains for each potential step, with one of the pulse trains being inverted, each one of the pulse trains being formed of at least one of the pulses.

4. An instrument according to claim 2, further comprising a memorization means for storing cumulative values of the integrated response signal at an end of each potential step.

5. An instrument according to claim 1, further comprising:

an additional signal generator means for generating an additional command signal;

and wherein:

the potentiostat has a second input for receiving the additional command signal, fourth and fifth instrument terminals, and additional regulating means for applying, between the fourth and fifth instrument terminals, an additional potential difference corresponding substantially to the additional command signal.

6. An instrument according to claim 5, wherein:

the additional command signal includes pulses superimposed on a DC bias potential;

the additional signal generator means includes means for selecting a DC level of the DC bias potential in the additional command signal; and the control means are configured to control the DC level of the DC bias potential in the additional command signal, the control means being provided with a mode of control maintaining a potential difference between the DC levels of the DC bias potentials in both command signals, the potential difference between the DC levels being similar to an amplitude of the pulses in the command signals.

7. An instrument according to claim 5, wherein:

the additional command signal includes pulses superimposed on a DC bias potential; and the control means is provided with a mode of control causing the means for selectively inverting the pulses to invert the pulses of the command signal in permanence, so that the pulses of the command signal are of opposite polarity with respect to the pulses of the additional command signal.

8. An instrument according to claim 1, wherein the potentiostat has a fourth instrument terminal, means for applying a predetermined voltage to the fourth instrument terminal and producing a signal indicative of a current flowing through the fourth instrument terminal, and means for subtracting the signals indicative of the currents flowing in the third and fourth instrument terminals, the predetermined voltage corresponding substantially to an amplitude of the pulses in the command signal.

9. An instrument according to claim 1, wherein the control means are provided with a mode of control causing the integrator means to integrate the output signal during predetermined discrete time periods between transitions of the pulses, while causing the means for selectively inverting the output signal to invert the output signal during predetermined ones of the time periods depending on the selected voltammetric mode of operation.

10. An instrument according to claim 9, wherein the time periods are two in number between successive transitions of the pulses.

11. An instrument according to claim 1, wherein the generator means comprise:

an active low pass filter including an amplifier combined with a resistor-capacitor feedback circuit to give the low pass filter a long time constant to filter noise and stabilize the command signal; and means for injecting a correcting charge in the capacitor of the low pass filter during pulse transitions in the command signal, to compensate an effect of the time constant of the low pass filter on rise and fall times of the pulses in the command signal.

12. An instrument according to claim 11, wherein:

the command signal is generated by means of a digital to analog converter driven by the control means, the digital to analog converter having an output for transmitting the command signal;

the capacitor, the resistor and the amplifier of the low pass filter are in parallel between input and output points; and the means for injecting comprise:

a resistor connected between the output of the digital to analog converter and the input point of the low pass filter;

an adjustable gain comparator having a first comparator input connected to the output point of the low pass filter, a second comparator input connected to the output of the digital to analog converter, and a comparator output for producing a signal proportional to a difference between absolute values of signals at the first and second comparator inputs; and a switch driven by the control means to close only for a predetermined time period during transitions of the pulses, the switch being connected between the comparator output and the input point of the low pass filter.

13. An instrument according to claim 11, wherein:

the command signal is generated by means of a digital to analog converter driven by the control means, the digital to analog converter having an output for transmitting the command signal;

the capacitor, the resistor and the amplifier of the low pass filter are in parallel between input and output points; and the means for injecting comprise:

a resistor connected between the output of the digital to analog converter and the input point of the low pass filter;

a capacitor having a first end connected to the output of the digital to analog converter, and a second end; and a two-way switch having a first terminal connected to the second end of the capacitor, a second terminal connected to the input point of the low pass filter, a third terminal connected to ground, the switch being driven by the control means to connect the first terminal with the second terminal for a predetermined time period during transitions of the pulses, and to connect the second terminal with the third terminal outside the time period.

14. An instrument according to claim 1, further comprising means for superimposing an impulse to a leading edge of each pulse in the command signal, the impulse having a predetermined amplitude and a predetermined duration.

15. An instrument according to claim 14, wherein the means for superimposing an impulse comprise:

a summing circuit having a first input for receiving the command signal, a second input for receiving the impulse, and an output for producing the command signal with the impulse;

an amplifier having an input connected to the input of the summing circuit, and an output;

an adjustable differentiator having an input connected to the output of the amplifier, and an output; and an adjustable attenuator having an input connected to the output of the differentiator, and an output for producing the impulse.

16. An instrument according to claim 15, wherein:

the adjustable differentiator comprises a set of capacitors in parallel, having different properties, and switches arranged to select the capacitors in circuit;

the adjustable attenuator comprises a pair of back to back diodes in parallel.

17. An instrument according to claim 16, wherein:

the properties of the capacitors are selected to permit adjustment of the duration of the impulses between 0.05 to 1 ms; and the amplitude of the impulse is less than approximately three times an amplitude of the pulses in the command signal.

18. An instrument according to claim 1, wherein the regulating means comprise:

a follower circuit in series with a first inverter circuit, the follower circuit having an input connected to the first instrument terminal, and an output, the first inverter circuit having an input connected to the output of the follower circuit, and an output;

a second inverter circuit having an input, and an output connected to the second terminal instrument; and a summing circuit having a first input connected to the input of the potentiostat, a second input connected to the output of the first inverter circuit, and an output connected to the input of the second inverter circuit.

19. An instrument according to claim 1, further comprising:

a feedback means for deriving, in response to a feedback control signal, a feedback signal from the output signal and adding the feedback signal to the potential difference applied between the first and second instrument terminals;

and wherein:

the control means are configured to produce the feedback control signal, the control means being provided with a mode of control where the feedback control signal is produced only for a predetermined time period at each transition of the pulses.

20. An instrument according to claim 1, wherein the means for grounding comprise a current to voltage converter including:

an amplifier having a first input connected to the third instrument terminal, a second input connected to ground, and an output for producing the output signal;

first and second variable resistance circuits to adjust a gain of the amplifier, the first resistance circuit being connected in parallel with the amplifier, the second resistance circuit being connected between the output of the amplifier and the ground; and a gain lowering circuit connected in parallel with the amplifier, the gain lowering circuit including a resistor having a lower resistance value than the first variable resistance circuit, and a switch circuit in resistor, to controllably open and close the gain lowering circuit in response to a gain lowering signal;

and wherein the control means are configured to produce the gain lowering signal the control means being provided with a mode of control causing the switch circuit to open for a predetermined time period during transitions of the pulses in the command signal, and to close outside the time period.

21. An instrument according to claim 20, wherein:

the switch circuit includes first and second switches in series, operated by the control means to both open and close identically, the first switch being connected to the output of the amplifier, the second switch being connected between the first switch and the resistor of the gain lowering circuit;

the means for grounding further comprise a resistor having a first end connected between the two switches and a second end connected to ground, the first end of the resistor being connected with the regulating means of the potentiostat by means of a summing circuit to add the output signal produced at the output of the amplifier with the command signal when the switches are closed.

22. An instrument according to claim 20, wherein the grounding means further comprise:

a low pass filter connected to the output of the amplifier of the current to voltage converter, the low pass filter having a switch responsive to a switch control signal provided by the control means, to temporarily maintain the output signal during transitions of the pulses.

23. An instrument according to claim 1, wherein:

the means for selectively inverting the output signal comprise an input for receiving the output signal, an output, a first switch responsive to a first switch control signal, and an inverter circuit in series with a second switch responsive to a second switch control signal, the first switch being connected between the input and the output of the means for selectively inverting, the inverter circuit and the second switch being connected in parallel with the first switch;

the integrator means comprise an integrator circuit having an input connected to the output of the means for selectively inverting the output signal, and an output for producing the integrated response signal; and the control means have outputs for producing the first and second switch control signals, to separately open and close the first and second switches according to a selected mode of integration.

24. An instrument according to claim 23, wherein:

the integrator circuit comprises: an amplifier having a first input for receiving the output signal, a second input connected to ground, and an output for producing the integrated response signal; a variable resistance circuit connected between the input of the integrator and the first input of the amplifier; and a variable capacitor circuit connected between the first input and the output of the amplifier;

the means for resetting comprise a switch responsive to a reset signal, the switch being connected between the first input and the output of the amplifier; and the control means have an output for producing the reset signal at predetermined times according to the selected voltammetric mode of operation.

25. An instrument according to claim 1, wherein the integrator means comprise:

voltage to frequency converter means for converting the output signal into a pulsed signal having a frequency indicative of a voltage value of the output signal;

UP/DOWN counter means for counting pulses in the pulsed signal to produce an output count signal, the counter means having an UP/DOWN input to receive an UP/DOWN control signal affecting a counting direction of the pulses in the pulsed signal, and a reset input to receive a reset signal causing the counter means to reset the output count signal;

comparator means for comparing the output signal with a reference signal selected to determine a polarity of the output signal, and producing a signal indicative of the polarity of the output signal; and logic circuit means for producing the UP/DOWN control signal depending on the polarity of the output signal as determined by the comparator means;

and wherein the control means have an output for producing the reset signal at predetermined times according to the selected voltammetric mode of operation.

26. An instrument according to claim 25, wherein:

the UP/DOWN counter means have a count enable input to receive a count enable signal enabling counting of the pulses;

the logic circuit means have control inputs for receiving control signals, and a set of built-in functions triggered by the control signals, to affect the UP/DOWN control signal and the count enable signal according to predetermined modes of integration; and the control means have outputs for producing the control signals for the logic circuit means according to the selected voltammetric mode of operation.

27. An instrument according to claim 25, wherein the integrator means further comprise:

a rectifier means for rectifying the output signal prior voltage to frequency conversion.

28. An accurate and low noise signal generator circuit for a potentiostat in a voltammetric instrument, the signal generator circuit comprising:

a pulse generator means for generating a command signal including pulses;

an active low pass filter connected to the pulse generator, the low pass filter including an amplifier combined with a resistor-capacitor feedback circuit to give the low pass filter a long time constant to filter noise and stabilize the command signal for transmission to the potentiostat; and means for injecting a correcting charge in the capacitor of the low pass filter during pulse transitions in the command signal, to compensate an effect of the time constant of the low pass filter on rise and fall times of the pulses in the command signal.

29. A circuit according to claim 28, wherein:

the pulse generator means have an output to produce the command signal;

the capacitor, the resistor and the amplifier of the low pass filter are in parallel between input and output points; and the means for injecting comprise:

a resistor connected between the output of the pulse generator means and the input point of the low pass filter;

an adjustable gain comparator having a first comparator input connected to the output point of the low pass filter, a second comparator input connected to the output of the pulse generator means, and a comparator output for producing a signal proportional to a difference between absolute values of signals at the first and second comparator inputs; and a switch having a control input to receive a switch signal causing the switch to close only for a predetermined time period during transitions of the pulses, the switch being connected between the comparator output and the input point of the low pass filter.

30. A circuit according to claim 28, wherein:

the pulse generator means have an output to produce the command signal;

the capacitor, the resistor and the amplifier of the low pass filter are in parallel between input and output points; and the means for injecting comprise:

a resistor connected between the output of the pulse generator means and the input point of the low pass filter;

a capacitor having a first end connected to the output of the pulse generator means, and a second end; and a two-way switch having a first terminal connected to the second end of the capacitor, a second terminal connected to the input point of the low pass filter, a third terminal connected to ground, the switch having an input to receive a switch signal causing the switch to connect the first terminal with the second terminal for a predetermined time period during transitions of the pulses, and to connect the second terminal with the third terminal outside the time period.

31. A circuit for reducing a double layer capacitive effect in an electrochemical cell having a pair of electrodes subjected to a potential difference produced by a potentiostat in response to a command signal including pulses corresponding to the potential difference to be produced, the circuit comprising:

a summing circuit having a first input for receiving the command signal, a second input for receiving impulses, and an output for superimposing the impulses onto the command signal;

an amplifier having an input connected to the input of the summing circuit, and an output;

an adjustable differentiator having an input connected to the output of the amplifier, and an output; and an adjustable attenuator having an input connected to the output of the differentiator, and an output to produce the impulses.

32. A potentiostat connected with an electrochemical cell having reference, working and counter electrodes, the potentiostat comprising:

an input for receiving a command signal corresponding to a potential difference to be applied between the working and reference electrodes, first, second and third instrument terminals connected with the reference, working and counter electrodes, respectively;

regulating means for applying the potential difference between the working and reference electrodes, the regulating means having a first input connected to the input of the potentiostat to receive the command signal, a second input connected to the first instrument terminal to receive a reference potential of the reference electrode, and an output connected to the second instrument terminal to apply an excitation potential on the working electrode, the excitation potential resulting from an addition of the reference potential with the command signal, thereby producing the potential difference between the working and reference electrodes; and means for grounding the third instrument terminal and producing an output signal indicative of a current flowing through the third instrument terminal.

33. A potentiostat according to claim 32, wherein the regulating means comprises:

a follower circuit in series with a first inverter circuit, the follower circuit having an input connected to the first instrument terminal, and an output, the first inverter circuit having an input connected to the output of the follower circuit, and an output;

a second inverter circuit having an input, and an output connected to the second instrument terminal; and a summing circuit having a first input connected to the input of the potentiostat, a second input connected to the output of the first inverter circuit, and an output connected to the input of the second inverter circuit.

34. A feedback circuit for compensating an ohmic drop in an electrochemical cell having a pair of electrodes subjected to a pulsed potential difference, and a grounded electrode in which current flows in response to the pulsed potential difference, the feedback circuit comprising:

a current to voltage converter having an input connected to the grounded electrode, and an output to produce a voltage signal as a function of the current;

a switch responsive to a switch signal, the switch having an input connected to the output of the current to voltage converter, and an output to transmit the voltage signal depending on the switch signal;

control means for producing the switch signal to close the switch for a predetermined time period during transitions of the pulsed potential difference, and to open the switch outside the time period;

a summing circuit for adding the voltage signal transmitted by the switch to the pulsed potential difference applied between the pair of electrodes.

35. A digital integrator arrangement for integrating a current signal produced by an electrochemical cell subjected to a pulsed potential difference, comprising:

a current to voltage converter having an input for receiving the current signal, and an output to produce a voltage signal indicative of the current signal;

a digital integrator having:
an input connected to the output of the current to voltage converter;
a voltage to frequency converter having an input connected to the input of the integrator, and an output to produce a pulsed signal having a frequency indicative of a voltage value of the voltage signal;
an UP/DOWN counter means for counting pulses in the pulsed signal to produce an output count signal, the counter means having an UP/DOWN input to receive an UP/DOWN control signal affecting a counting direction of the pulses in the pulsed signal, and a reset input to receive a reset signal causing the counter means to reset the output count signal;
comparator means for comparing the voltage signal with a reference signal selected to determine a polarity of the voltage signal, and producing a signal indicative of the polarity; and
logic circuit means for producing the UP/DOWN control signal depending on the polarity of the voltage signal as determined by the comparator means; and control means having an output to produce the reset signal at predetermined times according to a selected voltammetric mode of operation.

36. An arrangement according to claim 35, wherein:

the UP/DOWN counter means has a count enable input to receive a count enable signal enabling counting of the pulses;

the logic circuit means have control inputs to receive control signals, and a set of built-in functions triggered by the control signals, to affect the UP/DOWN control signal and the count enable signal according to predetermined modes of integration; and the control means have outputs to produce the control signals for the logic circuit means according to the selected voltammetric mode of operation.

* * * * *